US008975086B2

(12) United States Patent
Nakamura et al.

(10) Patent No.: US 8,975,086 B2
(45) Date of Patent: Mar. 10, 2015

(54) METHOD FOR TREATING OR PREVENTING BLADDER CANCER USING THE DEPDC1 POLYPEPTIDE

(75) Inventors: Yusuke Nakamura, Tokyo (JP); Toyomasa Katagiri, Tokyo (JP); Akira Togashi, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 1047 days.

(21) Appl. No.: 13/061,064

(22) PCT Filed: Aug. 21, 2009

(86) PCT No.: PCT/JP2009/004006
§ 371 (c)(1),
(2), (4) Date: May 26, 2011

(87) PCT Pub. No.: WO2010/023850
PCT Pub. Date: Mar. 4, 2010

(65) Prior Publication Data
US 2011/0237518 A1    Sep. 29, 2011

Related U.S. Application Data

(60) Provisional application No. 61/190,531, filed on Aug. 28, 2008.

(51) Int. Cl.
| | | |
|---|---|---|
| *G01N 33/53* | (2006.01) | |
| *A61K 38/00* | (2006.01) | |
| *C07K 7/00* | (2006.01) | |
| *C07K 14/00* | (2006.01) | |
| *C07K 14/82* | (2006.01) | |
| *C12N 15/113* | (2010.01) | |
| *G01N 33/50* | (2006.01) | |
| *A61K 48/00* | (2006.01) | |

(52) U.S. Cl.
CPC .............. *C07K 14/82* (2013.01); *C12N 15/113* (2013.01); *G01N 33/5011* (2013.01); *A61K 38/00* (2013.01); *A61K 48/00* (2013.01); *C07K 2319/10* (2013.01); *C12N 2310/14* (2013.01)
USPC ........... 436/501; 514/19.3; 530/324; 530/326

(58) Field of Classification Search
CPC ......... A61K 38/00; C07K 14/00; G01N 33/53
USPC ................... 514/19.3; 530/324, 326; 436/501
See application file for complete search history.

(56) References Cited

U.S. PATENT DOCUMENTS

| | | |
|---|---|---|
| 7,001,999 B1 | 2/2006 | Martelange et al. |
| 2003/0068675 A1 | 4/2003 | Liu |
| 2004/0241726 A1 | 12/2004 | Liew |
| 2009/0175844 A1 | 7/2009 | Nakamura et al. |
| 2009/0317392 A1 | 12/2009 | Nakamura et al. |
| 2010/0028373 A1 | 2/2010 | Fujioka et al. |

FOREIGN PATENT DOCUMENTS

| | | |
|---|---|---|
| JP | 2008-532477 A | 8/2008 |
| WO | WO 02/31111 A2 | 4/2002 |
| WO | WO 03/040165 A2 | 5/2003 |
| WO | WO 03/083074 A2 | 10/2003 |
| WO | WO 2004/112589 A2 | 12/2004 |
| WO | WO 2006/085684 A9 | 10/2006 |
| WO | WO 2007/013665 A2 | 2/2007 |
| WO | WO 2008/047473 A1 | 4/2008 |

OTHER PUBLICATIONS

Byers, T. (CA Cancer Journal, 1999, 49: 353-361).*
U.S. Appl. No. 13/536,327, filed Jun. 28, 2012, 204 pgs.
Ardavanis, et al., "Gemcitabine and docetaxel as first-line treatment for advanced urothelial carcinoma: a phase II study," *Br J Cancer*, vol. 92(4), pp. 645-650 (Feb. 28, 2005).
Ferries, et al., "Identification of p53 Peptides Recognized by CD8+ T Lymphocytes From Patients With Bladder Cancer," *Hum Immunol.*, vol. 62(8), pp. 791-798 (Aug. 2001).
Greenbaum, et al., "Interrelating Different Types of Genomic Data, from Proteome to Secretome: Oming in on Function," *Genome Res.*, vol. 11(9), pp. 1463-1468 (Sep. 2001).
Greenbaum, et al., "Comparing protein abundance and mRNA expression levels on a genomic scale," *Genome Biol.*, vol. 4(9): 117, 8 pages (Aug. 2003, Epub Aug. 29, 2003).
Harada, et al., "Investigation of a novel potential therapeutic modality targeting to DEPDC1 for bladder cancer," 68th *Annual Meeting of the Japanese Cancer Association Proceedings*, #O-338, p. 219 (2009).
Ito, et al., "Identification of Bladder Cancer Antigens Recognized by IgG Antibodies of a Patient with Metastatic Bladder Cancer," *Int J Cancer*, vol. 108(5), pp. 712-724 (Feb. 20, 2004).
Kanehira, et al., "Involvement of upregulation of *DEPDC1* (DEP domain containing 1) in bladder carcinogenesis," *Oncogene*, vol. 26(44), pp. 6448-6455 (Sep. 27, 2007, Epub Apr. 23, 2007).
Lehmann, et al., "Chemotherapy in the post-MVAC era: the case for adjuvant chemotherapy," *World J Urol.*, vol. 20(3), pp. 144-150 (Aug. 2002, Epub Feb. 27, 2002).

(Continued)

*Primary Examiner* — Mark Halvorson
*Assistant Examiner* — Yan Xiao
(74) *Attorney, Agent, or Firm* — Kilpatrick Townsend & Stockton LLP

(57) ABSTRACT

The present invention provides therapeutic agents and methods for treating cancer using the polypeptides composed of an amino acid sequence which includes a polypeptide fragment of DEPDC1. The polypeptides of the present invention can be introduced into cancer cells by modifying the polypeptides with transfection agents such as poly-arginine. Furthermore, the present invention provides methods of screening for therapeutic agents or compounds useful in inhibition of the DEPDC1/ZN-F224 complex formation or the treatment of cancer. The present invention also provides siRNAs targeting the ZNF224 gene, which are suggested to be useful in the treatment of bladder cancer.

2 Claims, 13 Drawing Sheets

(56) References Cited

OTHER PUBLICATIONS

Lu, et al., "siRNA-mediated antitumorigenesis for drug target validation and therapeutics," *Curr Opin Mol Ther.*, vol. 5(3), pp. 225-234 (Jun. 2003).

Ota, et al., "Complete sequencing and characterization of 21,243 full-length human cDNAs," *Nat Genet.*, vol. 36(1), pp. 40-45 (Jan. 2004, Epub Dec. 21, 2003).

Parkin, et al., "Global Cancer Statistics, 2002," *CA Cancer J Clin.*, vol. 55(2), pp. 74-108 (Mar.-Apr. 2005).

Rosenberg, et al., "Update on Chemotherapy for Advanced Bladder Cancer," *J Urol.*, vol.174(1), pp. 14-20 (Jul. 2005).

Saito-Hisaminato, et al., "Genome-Wide Profiling of Gene Expression in 29 Normal Human Tissues with a cDNA Microarray," *DNA Res.*, vol. 9(2), pp. 35-45 (Apr. 30, 2002).

Sanchez-Carbayo, "Recent advances in bladder cancer diagnostics," *Clin Biochem.*, vol. 37(7), pp. 562-571 (Jul. 2004).

Sternberg, "The treatment of advanced bladder cancer," *Ann Oncol.*, vol. 6(2), pp. 113-126 (Feb. 1995).

Takata, et al., "Predicting Response to Methotrexate, Vinblastine, Doxorubicin, and Cisplatin Neoadjuvant Chemotherapy for Bladder Cancers through Genome-Wide Gene Expression Profiling," *Clin Cancer Res.*, vol. 11(7), pp. 2625-2636 (Apr. 1, 2005).

Tang, et al., Database, ABP43909, 2 pages (Oct. 12, 2000).

Theodore, et al., "Multicentre EORTC study 16997: Feasibility and phase II trial of farnesyl transferase inhibitor & gemcitabine combination in salvage treatment of advanced urothelial tract cancers," *Eur J Cancer*, vol. 41(8), pp. 1150-1157 (May 2005).

Vaughn, "Review and Outlook for the Role of Paclitaxel in Urothelial Carcinoma," *Semin Oncol.*, vol. 26(1), Suppl. 2, pp. 117-122 (Feb. 1999).

U.S. Appl. No. 13/168,720, filed Jun. 24, 2011, 204 pages.

Harada, et al., "Cell-Permeable Peptide DEPDC1-ZNF224 Interferes with Transcriptional Repression and Oncogenicity in Bladder Cancer Cells," *Cancer Res.*, vol. 70(14), pp. 5829-5839 (Jul. 15, 2010, Epub Jun. 29, 2010).

Supplementary European Search Report for EP 09 80 9506, 1 page, search completed Mar. 12, 2012.

U.S. Appl. No. 13/535,297, 91 pages, filed Jun. 27, 2012.

U.S. Appl. No. 13/535,303, 91 pages, filed Jun. 27, 2012.

U.S. Appl. No. 13/562,250, 91 pages, filed Jul. 30, 2012.

\* cited by examiner

Fig. 3
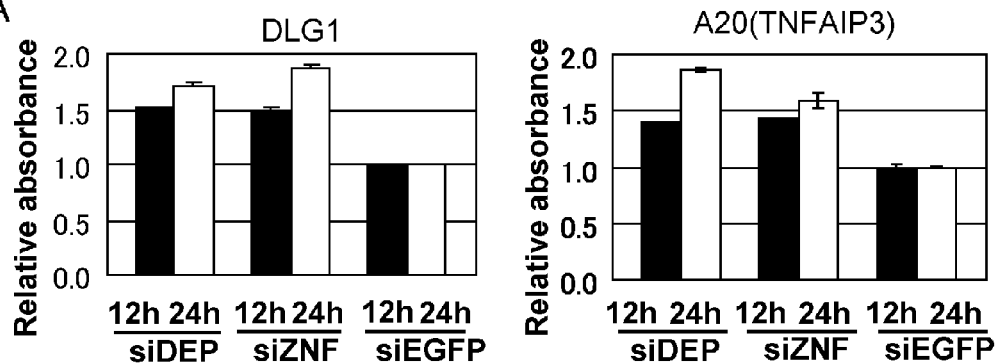
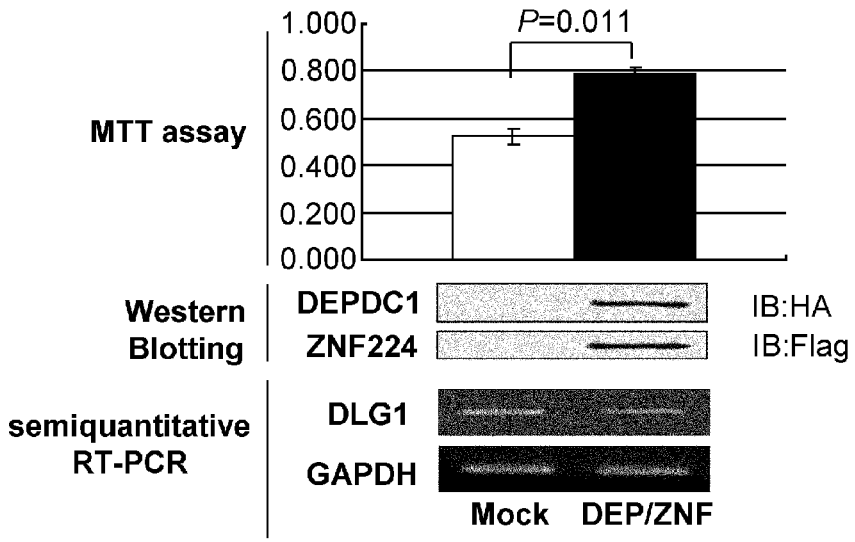
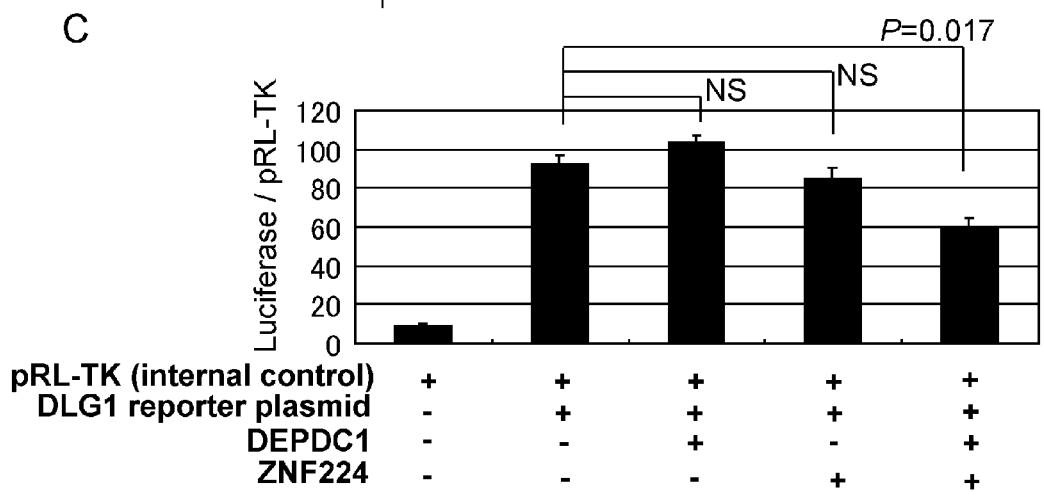

Fig. 4
A
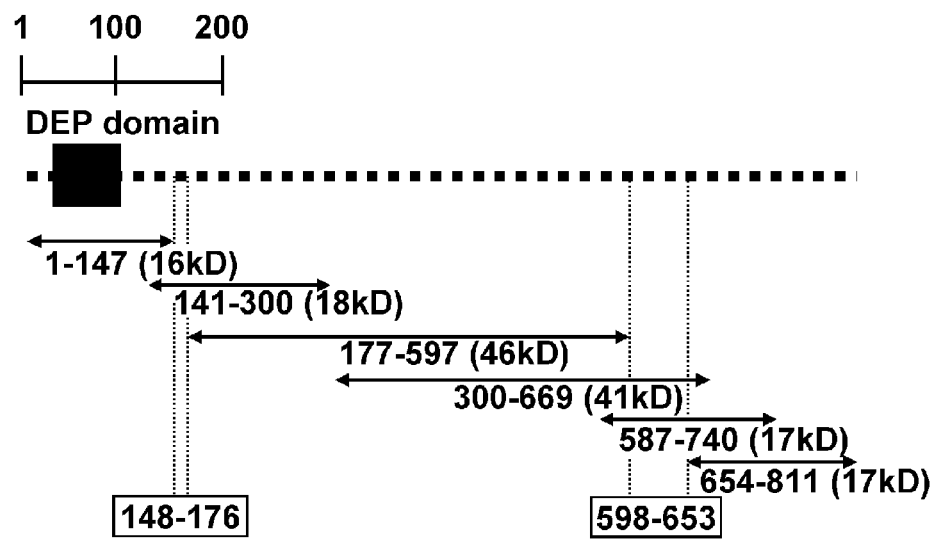
B
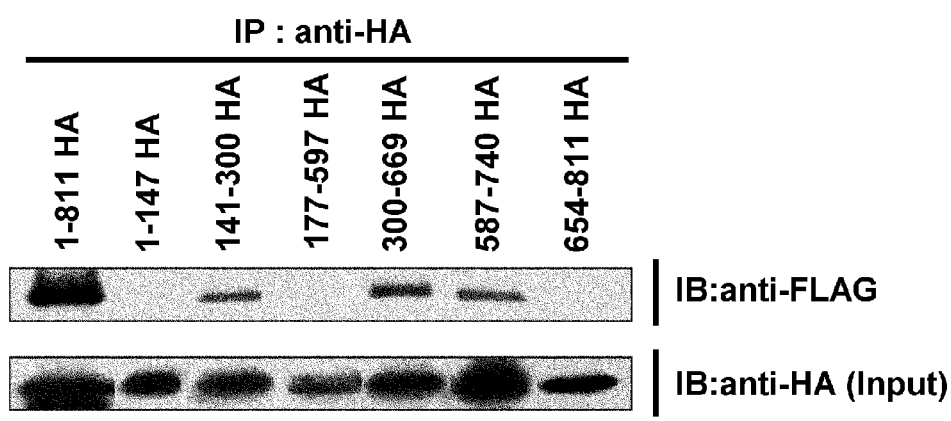

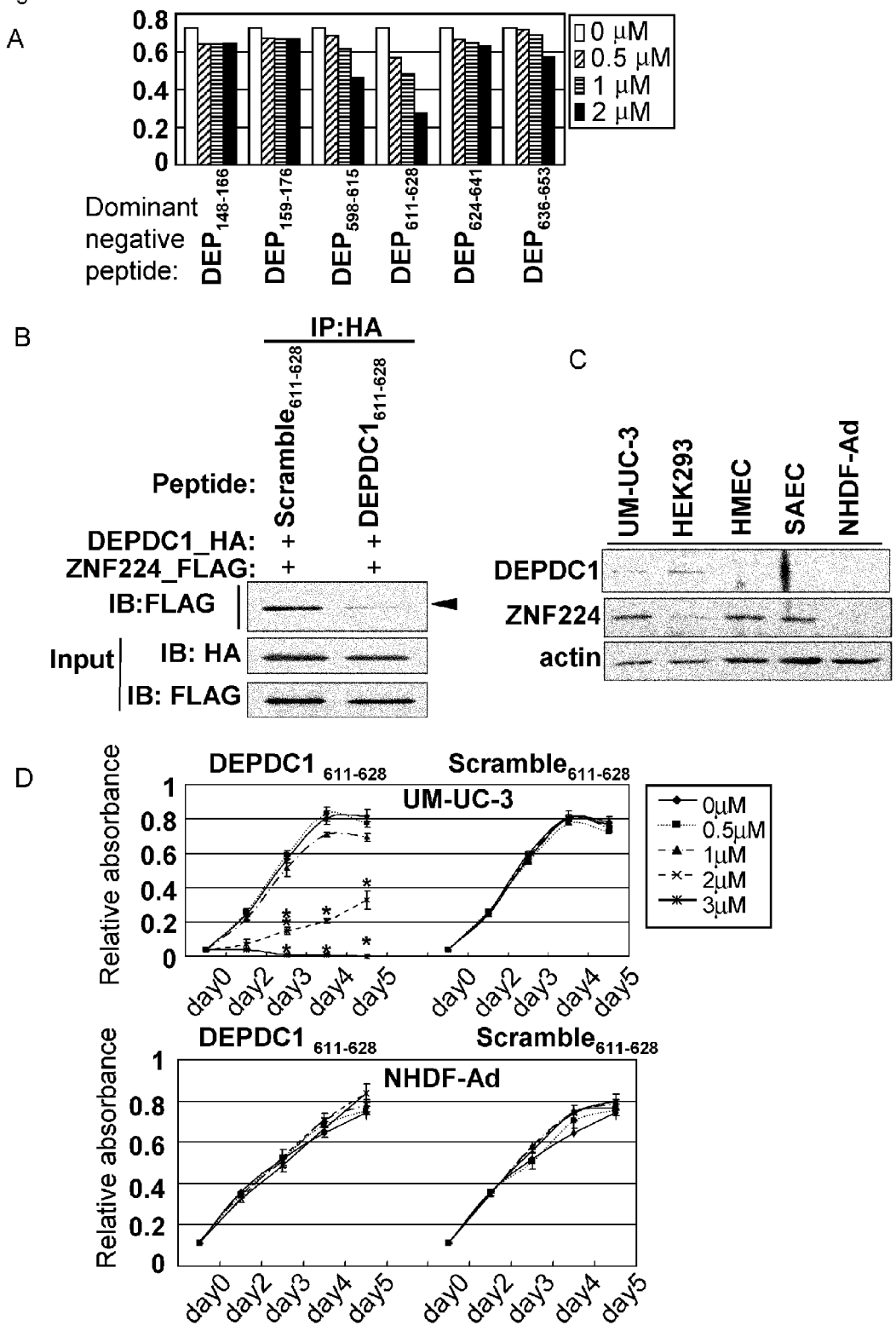
Fig. 5A-D

Fig. 5E-G
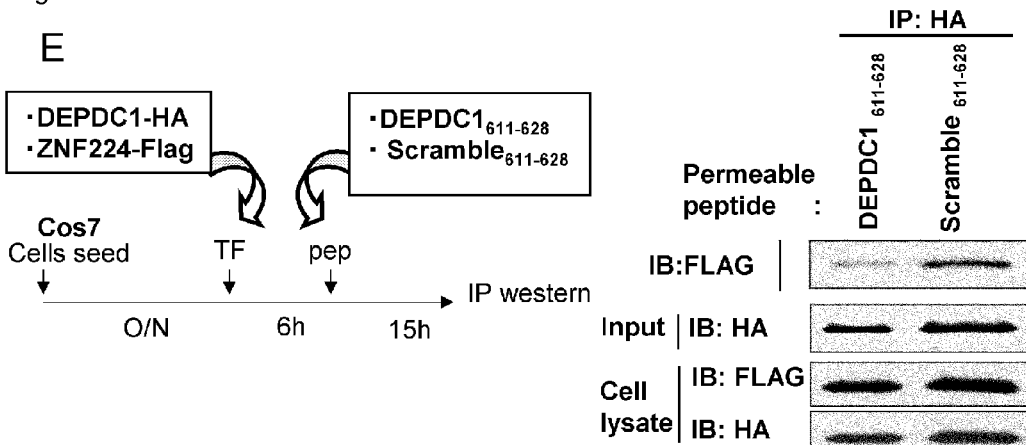
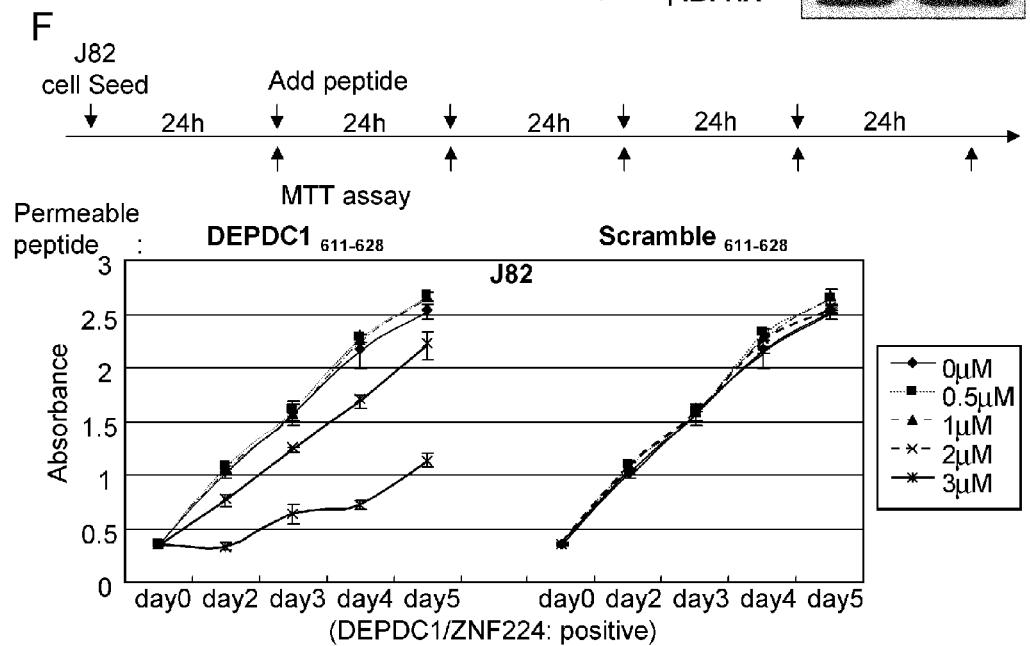
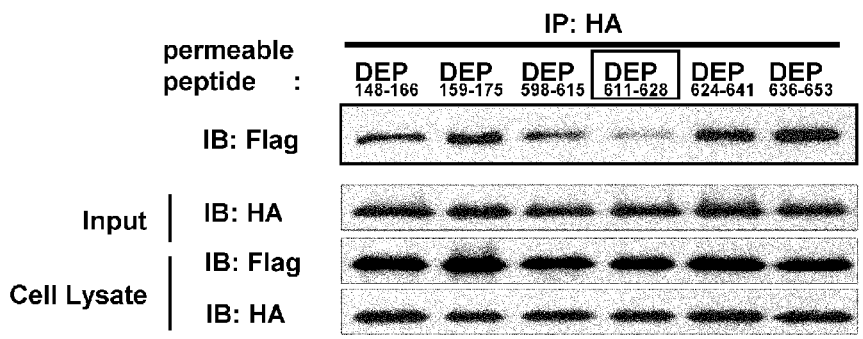

Fig. 6
A
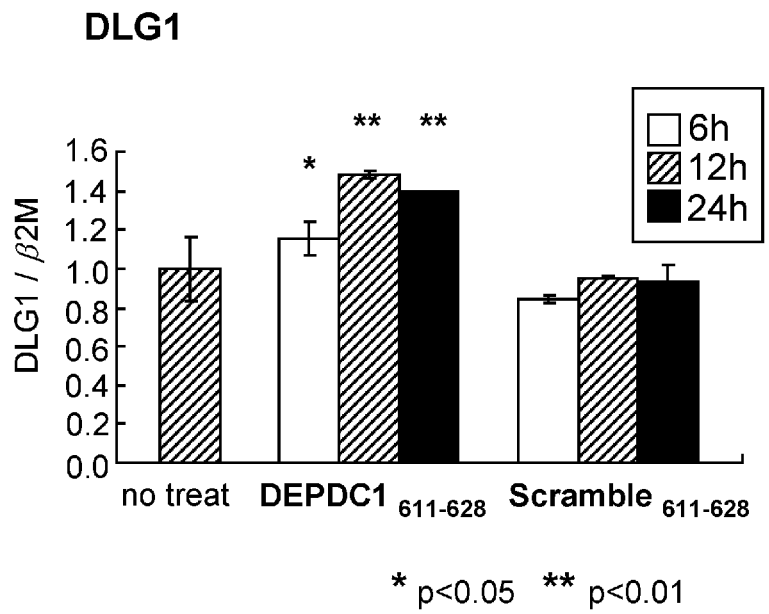
B
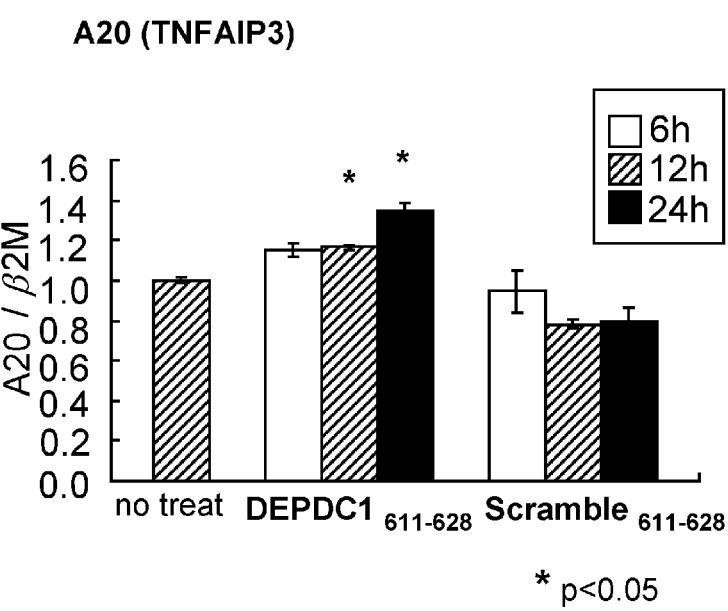

Fig. 7
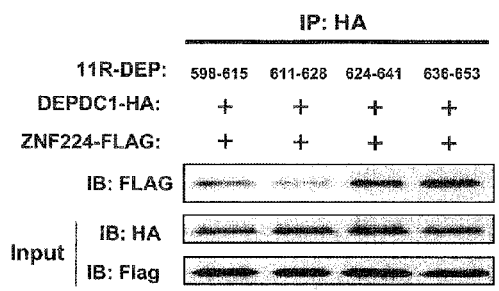
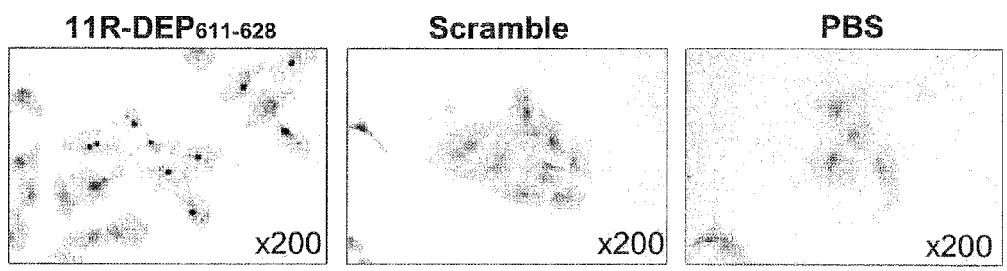
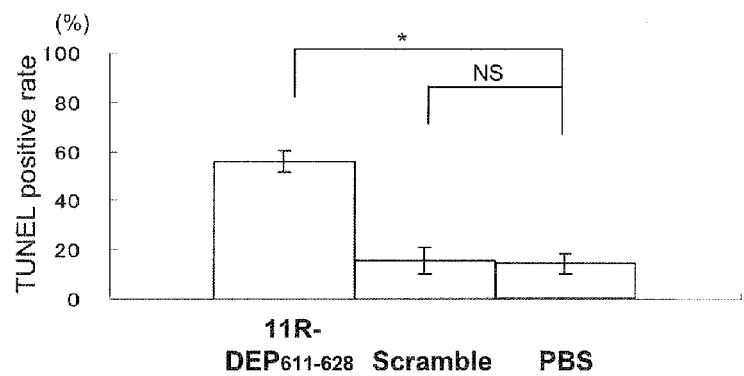
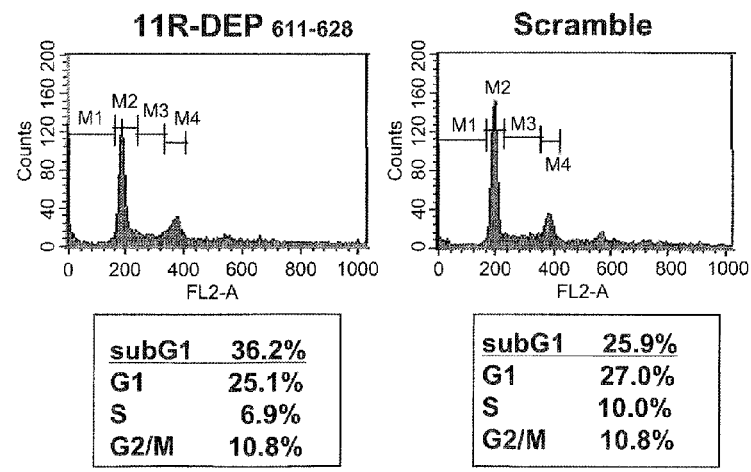

Fig. 9
A
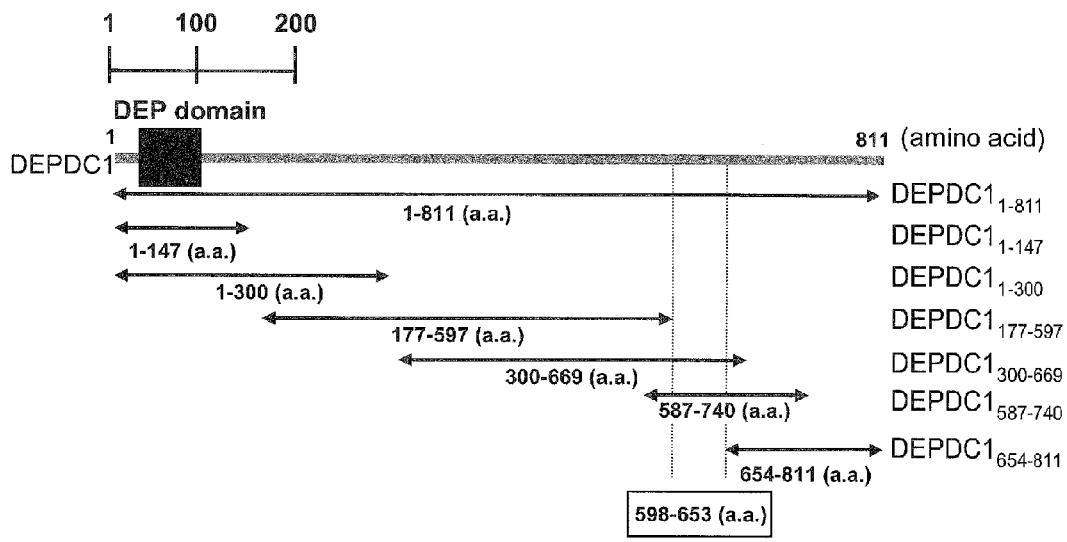
B
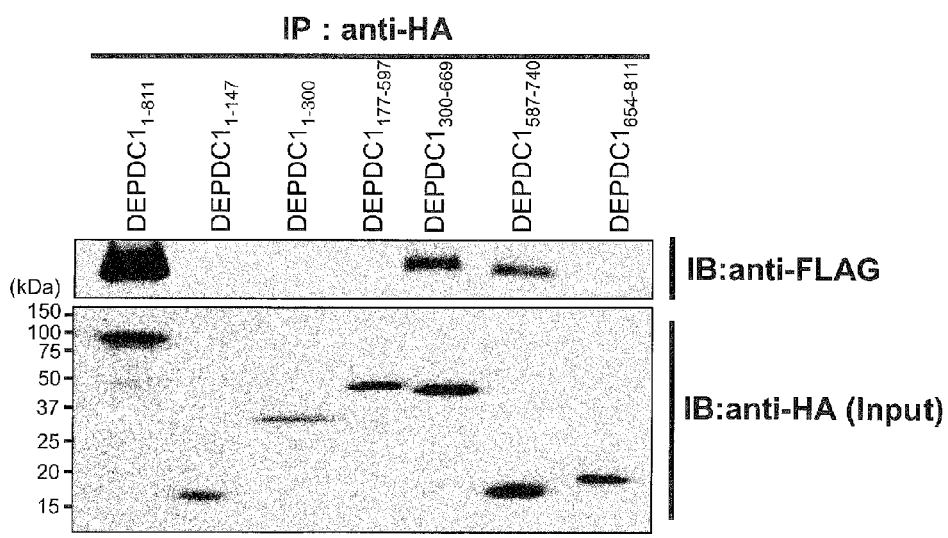

Fig. 10
A
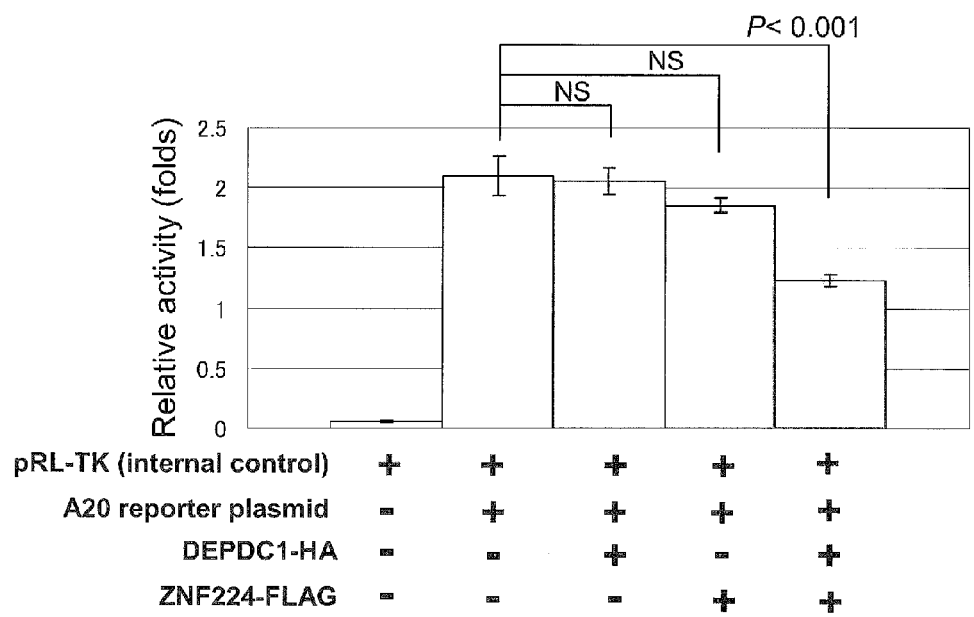
B
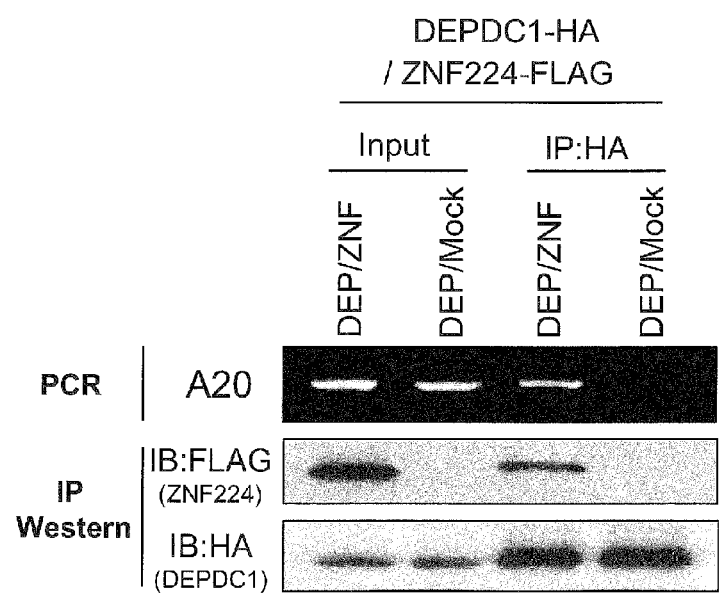

Fig. 11
A
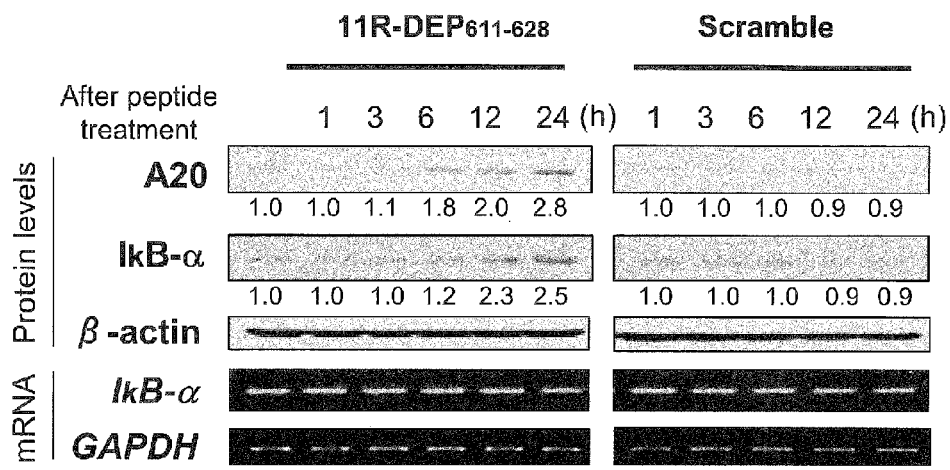
B
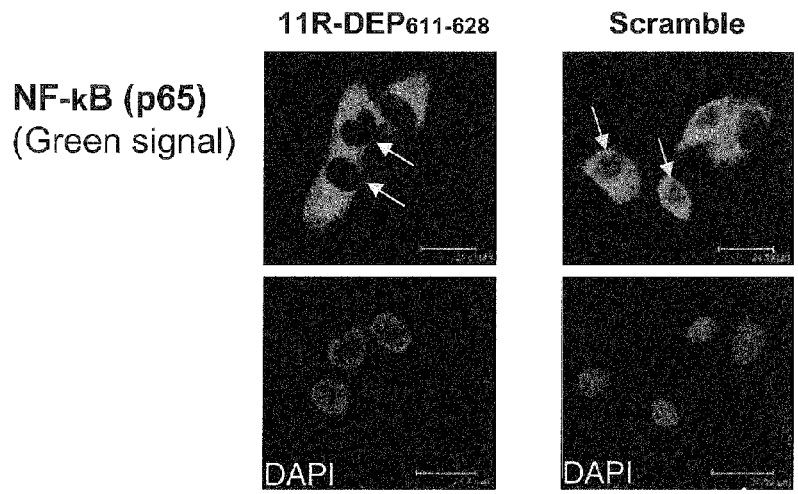
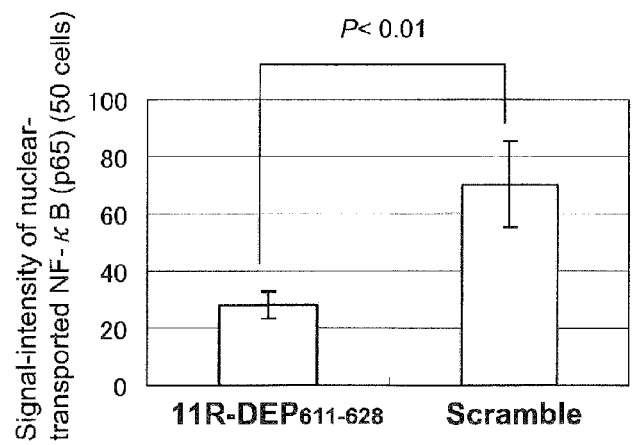

Fig. 12
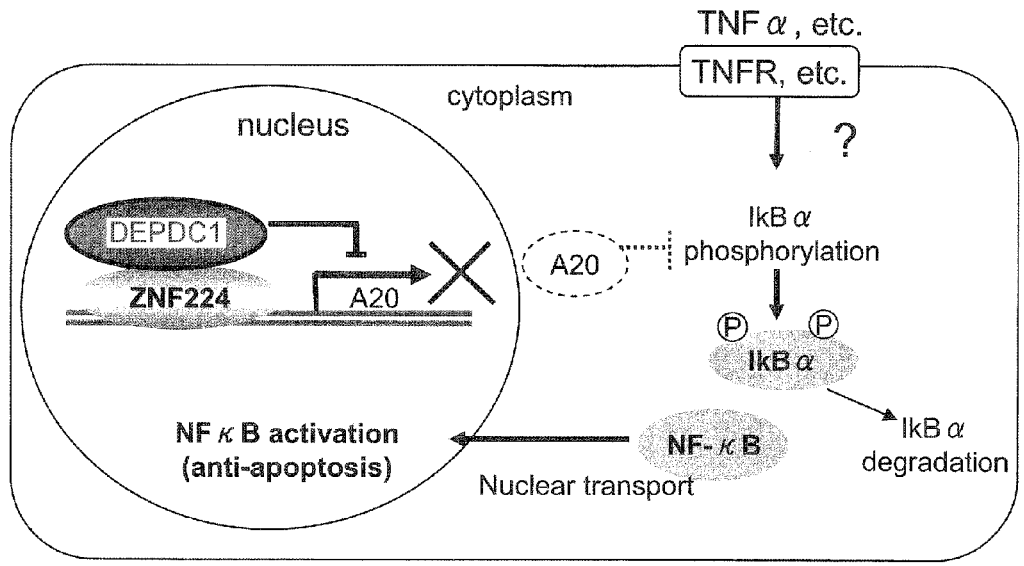
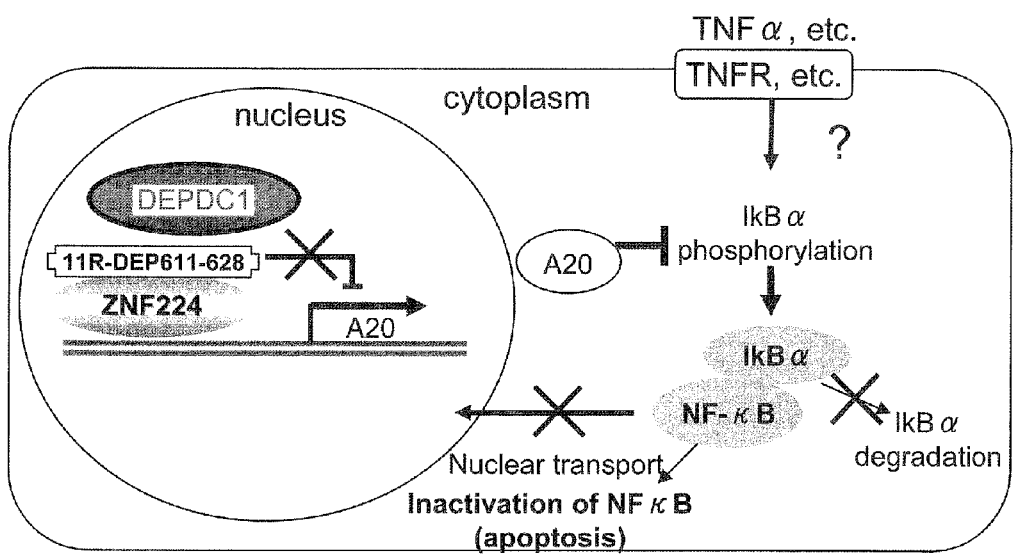

METHOD FOR TREATING OR PREVENTING BLADDER CANCER USING THE DEPDC1 POLYPEPTIDE

PRIORITY

The present application is a U.S. National Stage Application of PCT/JP2009/004006, filed Aug. 21, 2009, which claims the benefit of U.S. Provisional Application No. 61/190,531, filed on Aug. 28, 2008, the entire contents of which are incorporated by reference herein in their entirety.

TECHNICAL FIELD

The present invention relates to methods for treating or preventing bladder cancer as well as methods of screening for a compound for treating or preventing bladder cancer. In particular, the present invention relates to DEPDC1.

BACKGROUND ART

Bladder cancer is the second most common genitourinary tumor, having an incidence of approximately 357,000 new cases each year worldwide (Parkin D M, et al., Cancer J Clin 2005 55:74-108). Approximately one third of them are suspected to be invasive or metastatic disease at the time of diagnosis (NPL 1-3). Although radical cystectomy for invasive bladder cancer remains the standard of treatment in many parts of the world, nearly half of such patients develop metastases within two years after cystectomy and subsequently die of the disease. In the last two decades cisplatin-based combination chemotherapy regimens, such as CMV (cisplatin, methotrexate, and vinblastine) or M-VAC (methotrexate, vinblastine, doxorubicin, and cisplatin), have been prescribed for patients with advanced bladder cancers (NPL 3-6). However, the overall prognosis still remains very poor and adverse reactions caused by these combination chemotherapies are significantly severe (NPL 7). Therefore, development of a new molecular target drug(s) against bladder cancer is desired earnestly.

With that goal in mind, the present inventors previously analyzed the gene-expression profiles of 26 bladder cancers and 29 normal human tissues (NPL 8,9), and identified a gene and corresponding peptide designed DEP domain containing 1 (DEPDC1) that was highly up-regulated in the great majority of bladder cancer cells, but not expressed in normal human organs except testis, indicating this molecule to be a novel cancer/testis antigen (PTL 1). This data further suggested that DEPDC1 could serve as a valuable target for development of anti-cancer agents or cancer peptide-vaccines for bladder cancer (PTL 2). Further research demonstrated that suppression of DEPDC1 expression with small-interfering RNA (siRNA) significantly inhibited growth of bladder cancer cells. Although the data to date suggests that DEPDC1 plays a critical role in the growth and/or survival of bladder cancer, its molecular mechanism remains unknown.

CITATION LIST

Patent Literature

[PTL 1] WO2006/085684
[PTL 2] WO/2008/047473

Non Patent Literature

[NPL 1] Parkin D M, et al., Cancer J Clin 2005 55:74-108
[NPL 2] Sternberg C N, et al., Ann Oncol 1995 6:113-26
[NPL 3] Ardavanis A, et al., Br J Cancer 2005 92:645-50
[NPL 4] Lehmann J, et al., World J Urol 2002 20:144-50
[NPL 5] Rosenberg J E, et al., J Urology 2005 174:14-20
[NPL 6] Theodore C, et al., Eur J Cancer 2005 41:1150-7
[NPL 7] Vaughn D J, et al., Semin Oncol 1999 Suppl 2; 117-22
[NPL 8] Takata R, et al., Clin Cancer Res 2005 11:2625-36
[NPL 9] Saito-Hisaminato A, et al., DNA Res 2002 9:35-45

SUMMARY OF INVENTION

The present invention discloses that DEPDC1 plays a significant role in bladder carcinogenesis by suppressing multiple down-stream genes, including DIG1, through its interaction with zinc finger protein 224 (ZNF224), a transcriptional repressor. As demonstrated herein, inhibiting the interaction of DEPDC1 and ZNF224 with cell-permeable dominant-negative peptides resulted in growth suppression of bladder cancer cells. Moreover, the suppression of the ZNF224 gene by small interfering RNA (siRNA) resulted in growth inhibition and/or cell death of bladder cancer cells. These findings support the inventive premise—that the DEPDC1/ZNF224 complex plays a critical role in bladder carcinogenesis and that inhibition of DEPDC1/ZNF224 complex formation will lead to potential strategies for the treatment of bladder cancer.

Accordingly, it is an object of the present invention to provide methods for identifying compounds that inhibit the binding between the DEPDC1 protein and the ZNF224 protein, methods that involve the steps of contacting the DEPDC1 protein and ZNF224 protein with test compounds and determining the relative binding of these peptides. Measured inhibition of the binding theses peptides as compared to a control level observed in the absence of the test compound indicates that the test compound may be used to reduce symptoms of bladder cancer.

It is a further object of the present invention to provide methods for identifying compounds for treating or preventing cancer, such methods involving the steps of contacting a cell expressing DEPDC1 and ZNF224 with test compounds and determining the expression level of DLG1 or A20 (TNFAIP3). Measured reduction of the expression level as compared to a control level observed in the absence of the test compound indicates that the test compound may be used to reduce symptoms of bladder cancer.

It is a further object of the present invention to provide methods for identifying compounds for treating or preventing cancer, such methods involving the steps of contacting a cell expressing DEPDC1 and ZNF224 into which a vectorhousing the transcriptional regulatory region of DLG1 or A20 (TNFAIP3) and a reporter gene has been introduced with test compounds and determining the expression or activity of the reporter gene. Measured reduction of the expression or activity as compared to a control level observed in the absence of the test compound indicates that the test compound may be used to reduce symptoms of bladder cancer.

It is a further object of the present invention to provide methods for treating or preventing breast cancer in a subject that involve the step of administering siRNA composition to the subject. In the context of the present invention, the siRNA composition reduces the expression of the ZNF224 gene. In yet another method, the treatment or prevention of bladder cancer in a subject may be carried out by administering a nucleic acid composition to the subject. In the context of the present invention, the nucleic acid or amino acid-specific nucleic acid composition reduces the expression or activity of the ZNF224 gene.

The results presented herein confirm the inhibitory effects of siRNAs for the ZNF224 gene. For example, the inhibition of cell proliferation of cancer cells by the siRNAs are demonstrated in the Examples section, the data from which support the fact that the ZNF224 gene serves as a preferable therapeutic target for bladder cancer. Thus, it is yet another object of the present invention to provide double-stranded molecules which serve as siRNAs against the ZNF224 gene as well as vectors expressing the double-stranded molecules.

One advantage of the methods described herein is that the disease may be identified prior to detection of overt clinical symptoms of bladder cancer. By detecting disease at an earlier stage, the present invention can improve the patient's prognosis and increase the probability for recovery and/or extended survival. Other features and advantages of the invention will be apparent from the following detailed description, and from the claims.

BRIEF DESCRIPTION OF DRAWINGS

Various aspects and applications of the present invention will become apparent to the skilled artisan upon consideration of the brief description of the figures and the detailed description of the present invention and its preferred embodiments which follows:

FIG. 3 depicts the growth-promoting effects and repression of candidate downstream genes of DEPDC1/ZNF224. Part A depicts the results of real-time PCR analysis, which confirm the increase of expression of DLG1 and A20 in siRNA-DEPDC1, siRNA-ZNF224 or siRNA-EGFP (control) treated cells. Part B depicts the inhibition of transactivation of DLG1 by overexpression of DEPDC1 and ZNF224. Part C depicts the results of a reporter activity assay.

FIG. 4 depicts the identification of the ZNF224-binding region in DEPDC1 and inhibition of growth of bladder cancer cells by dominant-negative fragment of DEPDC1.

Figure 1:
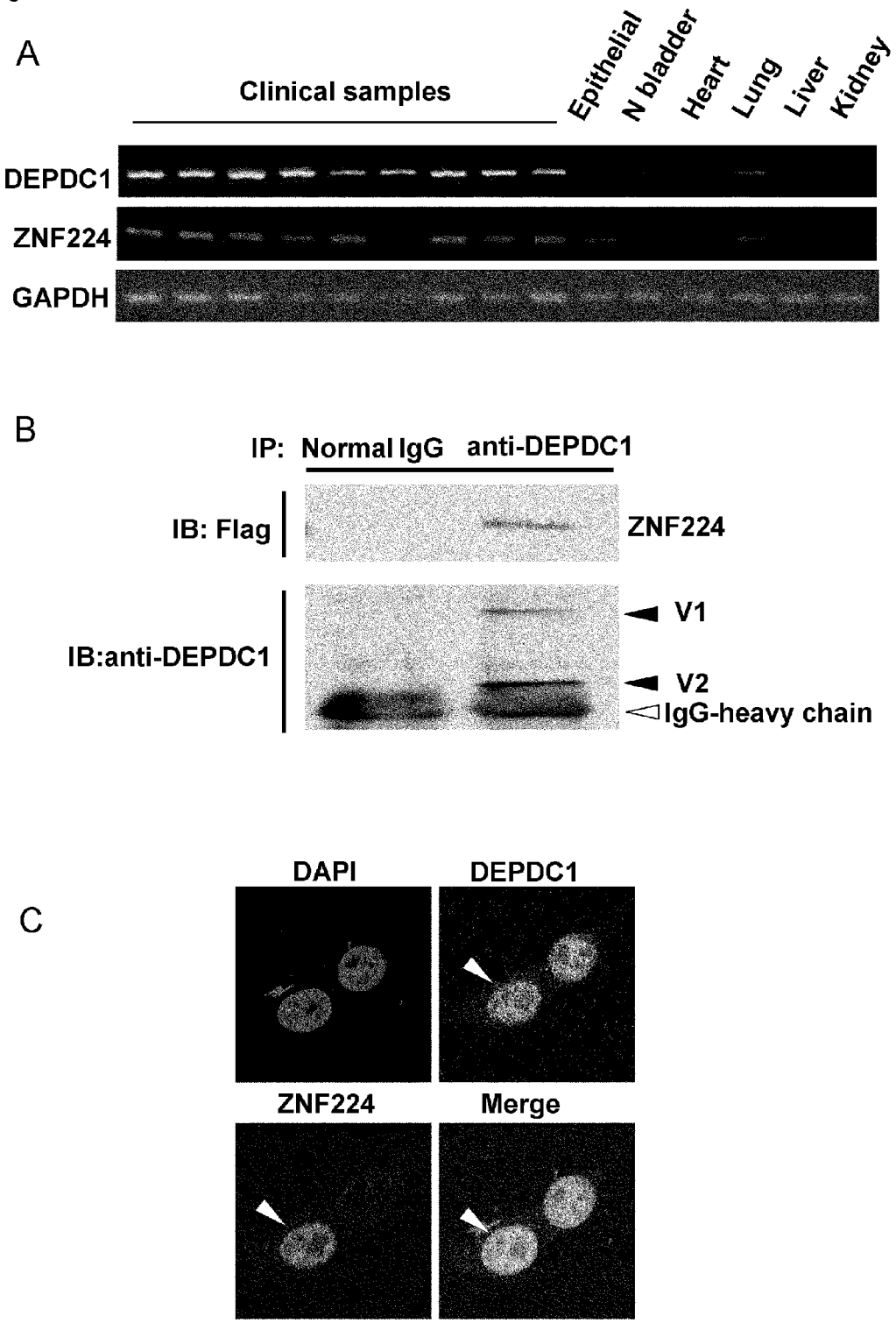
FIG. 1 depicts the interaction of DEPDC1 with ZNF224 in bladder cancer cells. Part A depicts the results of semiquantitative RT-PCR analysis, which, in turn confirm the up-regulation of DEPDC1 and ZNF224 in clinical bladder cancer samples. Appropriate dilutions of single-stranded cDNA were prepared from mRNAs of clinical bladder cancer samples, taking the level of GAPDH expression as a quantitative control. Epithelial; normal epithelial bladder, N bladder; normal bladder. Part B depicts the results of immunoprecipitation assays of endogenous DEPDC1 and exogenous ZNF224 from extracts of bladder cancer cell line UM-UC-3 transient expressed ZNF224-Flag plasmid. Part C depicts the co-localization of endogenous DEPDC1 (green) and exogenous ZNF224 (red) in UM-UC-3 cells.

Part A is a schematic drawing of six COOH-terminal HA-tagged DEPDC1 partial clones lacking either or both of the terminal regions. Molecular weights of each partial clones are described in the parenthesis. The top portion depicts the relative polypeptide size (1-200) of the constructs (amino acids).

Part B depicts the results of immunoprecipitation experiments, identifying the region in DEPDC1 that binds to ZNF224. The DEP1-147, DEP177-597 and DEP654-811 constructs, which lacked 148-176 or 598-653 amino-acid polypeptides in DEPDC1, did not retain any ability to interact with exogenous ZNF224 in Cos7 cells. This result suggests that the 29-amino-acid segment (codons 148-176) and 56-amino-acid segment (codons 598-653) were supposed to be important to interact with endogenous ZNF224.

FIG. 5 depicts the growth-inhibition of bladder cancer cells by dominant-negative peptides of DEPDC1. Part A presents the results of a growth-inhibition assay in UM-UC-3 wherein effective peptide from binding region of DEPDC1 were screened with ZNF224. A dominant-negative peptide was selected from six synthetic peptide herein. Part B depicts the results of immunoprecipitation assays between exogenous DEPDC1 and ZNF224 proteins in bladder cancer cells that were treated with the DEPDC1$_{611-628}$ peptides (black arrow) wherein a reduction of the complex formation was detected. Input fractions are shown at the bottom. Part C depicts the results of western blotting analysis using anti-DEPDC1 and ZNF224 antibody to detect the expression of endogenous DEPDC1 and ZNF224 proteins in four normal cell lines and bladder cancer cell lines assayed. No expressions of DEPDC1 and ZNF224 proteins in normal human dermal fibroblasts derived NHDF-Ad cells compared with bladder cancer cell line. Part D depicts the results of an MTT assay confirming the growth suppressive effect of DEPDC1$_{611-628}$ peptides that were introduced into DEPDC1-ZNF224 overexpressing UM-UC-3 cells and DEPDC1-ZNF224 not expressing NHDF-Ad cells. Bars, SD of triplicate assays. MTT assay shows no off-target effect of the DEPDC1$_{611-628}$ peptides on NHDF-Ad cells that scarcely expressed DEPDC1 and ZNF224 protein (bottom). Part E validates the reduction of complex formation detected by immunoprecipitation between exogenous DEPDC1 and exogenous ZNF224 proteins in COS7 cells that were treated with the 11R-DEP$_{611-628}$ peptides. COS7 cells were co-transfected with HA-tagged DEPDC1 and Flag tagged ZNF224 construct, followed by treatment of 11R-DEP$_{611-628}$ peptide or scramble$_{611-628}$ peptide at 6 h after transfection. Fifteen hours later, MTT assay was carried out. Part F depicts the inhibition of growth of J82, bladder cancer cell line by the 11R-DEP$_{611-628}$ peptides. MTT assays showed growth suppressive effect of the 11R-DEP$_{611-628}$ peptides that were introduced into DEPDC1-ZNF224 over-expressing J82 cells. Part G, Identification of the region in DEPDC1 that binds to ZNF224 by immunoprecipitation experiments. The 11R-DEP$_{611-628}$ peptides treatment did not retain analyzability to interact with exogenous Flag-tagged ZNF224, and the 11R-DEP$_{611-628}$ suggesting that Inhibition of complex fomationExpression of HA-tagged DEPDC1 and Flag-tagged ZNF224 construct.

FIG. 6 depicts the repression of DLG1 and A20 of DEPDC1-ZNF224 complex after treatment of 11R-DEP$_{611-628}$ peptide. Part A depicts the up-regulation of DLG1 expression and G1 arrest by dominant negative peptide in bladder cancer cells. Part B depicts the up-regulation of A20 expression and G1 arrest by dominant negative peptide in bladder cancer cells.

FIG. 7 depicts inhibition of cell growth of bladder cancer by dominant-negative peptides of DEPDC1. Part A depicts the effects of the complex formation detected by immunoprecipitation between exogenously-expressed DEPDC1 (DEPDC1-HA) and ZNF224 (ZNF224-FLAG) proteins in COS7 cells that were treated with each of four dominant-negative peptides (11R-DEP$_{598-615}$, 11R-DEP$_{611-628}$, 11R-DEP$_{624-641}$, and 11R-DEP$_{636-653}$). Part B, Apoptosis analysis of UM-UC-3 cells after treatment of 11R-DEP$_{611-628}$ or scramble peptides induced apoptotic cell-death. Cells were incubated with peptides (11R-DEP$_{611-628}$ peptide and scramble peptide; 3 micro M added) or PBS for 12 hours, respectively. Upper panels show representative images of TUNEL assays. Apoptotic cells were measured by counting of TUNEL staining (lower panels, see Materials and methods). Data are means +/−SE from triple experiments. (11R-DEP611-628 vs PBS; *, P<0.000001, unpaired, t-test, NS, not significant). Part C, Increase of apoptosis by treatment of 11R-DEP$_{611-628}$. Proportions of apoptotic cells were indicated as a percentage of the sub-G1 fraction in FACS analysis.

Figure 8:
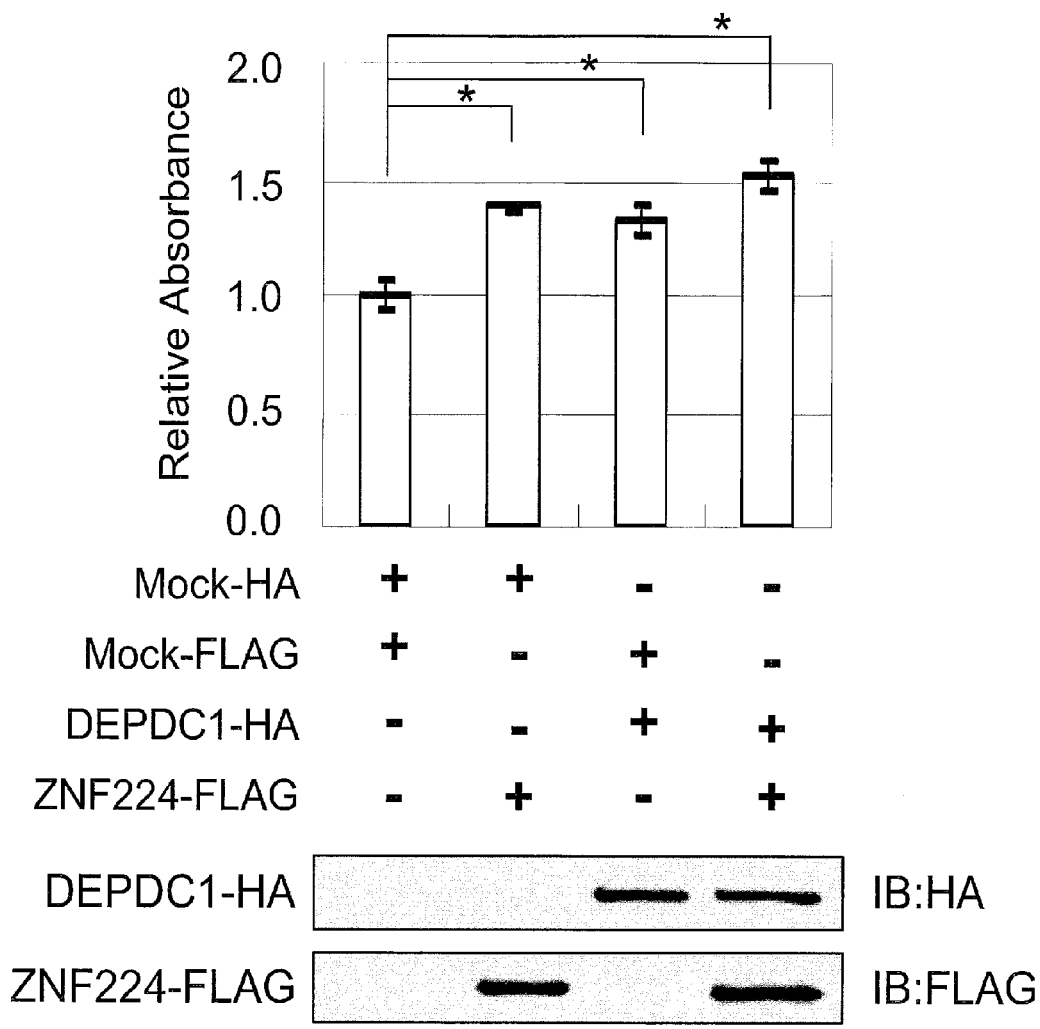

FIG. 8 depicts the enhancement of cell growth by co-expression of DEPDC1 and ZNF224. MTT assays were performed to evaluate cell viability and graphed after standardization by mock to 1.0. Western blot analysis showed the expression of DEPDC1-HA and ZNF224-FLAG proteins, respectively (lower panel). Expression of beta-actin is served as a loading control. Asterisks denote significant differences (P<0.05) determined by unpaired t-test.

FIG. 9 depicts the dentification of the ZNF224-binding region in DEPDC1. Part A depicts the schematic representation of six COOH-terminal HA-tagged DEPDC1 partial clones lacking either or both of the terminal regions. Top, relative polypeptide size (1-200) of the constructs (amino acids). Part B depicts the identification of the region in DEPDC1 that binds to ZNF224 by co-immunoprecipitation experiments. The 1-147HA, 1-300HA, 177-597HA and 654-811HA constructs, which lost 56-amino-acid polypeptides corresponding DEPDC1$_{598-653}$, were unable to interact with exogenous ZNF224 protein.

FIG. 10 depicts the identification of A20 as a candidate downstream gene of DEPDC1-ZNF224 complex. Part A depicts the effect of DEPDC1-ZNF224 complex on the luciferase activity of reporter plasmids containing the promoter region of A20 gene in NHDF cells. Luciferase activity is indicated relative to the activity of pRL-TK-promoter vector without A20 promoter region. Part B depicts the association of DEPDC1-ZNF224 complex with DNA fragment containing A20 promoter region, detected by ChIP assay. In the top panel, DNA from HEK293 cells was immunoprecipitated with indicated antibodies and served for PCR.

FIG. 11 depicts inhibition of NF-kappaB signaling pathway in bladder cancer cells by treatment of 11R-DEP$_{611-628}$ peptide. Part A depicts the upregulation of A20 expression and accumulation of I kappa B by treatment of 11R-DEP$_{611-628}$ peptide. UM-UC-3 cells were treated with 11R-DEP$_{611-628}$ peptide (3 micro M). Then, cell lysate were analyzed by western blot analysis with anti-A20 and anti-I kappa B antibodies at 0, 1, 3, 6, 12 and 24 hours after the treatment. GAPDH served as a quantitative control for RT-PCR. Beta-actin served as a loading control for western blot analysis. The relative expression level of A20 and I kappa B proteins was quantitated by densitometric analyses, and fold increase relative to untreated samples was calculated. Part B, Blocking of NF-kappaB (p65) nuclear transport in UM-UC-3 cells by treatment of 11R-DEP$_{611-628}$ peptide. After peptide treatment, NF-kappaB (p65) protein expression was analyzed by immunocytochemical staining (green) with an anti-NF-kappaB (p65) monoclonal antibody. For the image analysis, the nuclear signal intensities of NF-kappaB (p65) were measured by observing 50 nuclei in the 11R-DEP$_{611-628}$ peptide-treated cells (white arrows) as well as scramble peptide-treated cells (yellow arrows) for each experiment. Data are means +/−SE from triplicate experiments. *, P<0.01 for 11R-DEP$_{611-628}$ peptide treatment relative to scramble peptide. The yellow arrows indicate the nuclear-transported NF-kappaB (p65) protein.

FIG. 12 depicts schematic presentation of blocking of NF-kappaB-anti-apoptotic pathway via reactivation of A20 by 11R-DEP$_{611-628}$ peptide. In bladder cancer cells, transactivated DEPDC1 protein was repressed A20 transactivation through its interaction with ZNF224 as co-transcriptional repressor, resulting in activation of anti-apoptotic pathway through activation of NF-kappa B (upper panel). On the other hand, in the treatment of dominant negative peptide, 11R-DEP$_{611-628}$, transcriptional activity of A20 is up regulated by inhibition of DEPDC1-ZNF224 complex formation, resulting in intracellular accumulation of I kappa B, followed by inhibition of anti-apoptotic pathways through inactivation of NF-kappa B (lower panel).

DESCRIPTION OF EMBODIMENTS

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

In case of conflict, the present specification, including definitions, will control. In addition, the materials, methods, and examples are illustrative only and not intended to be limiting.

I. Definitions

The words "a", "an", and "the" as used herein mean "at least one" unless otherwise specifically indicated.

As used herein, the term "biological sample" refers to a whole organism or a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). "Biological sample" further refers to a homogenate, lysate, extract, cell culture or tissue culture prepared from a whole organism or a subset of its cells, tissues or component parts, or a fraction or portion thereof. Lastly, "biological sample" refers to a medium, such as a nutrient broth or gel in which an organism has been propagated, which contains cellular components, such as proteins or polynucleotides.

The terms "gene", "polynucleotide", "oligonucleotide" "nucleotide", "nucleic acid", and "nucleic acid molecule" are used interchangeably herein to refer to a polymer of nucleic acid residues and, unless otherwise specifically indicated are referred to by their commonly accepted single-letter codes. The terms apply to nucleic acid (nucleotide) polymers in which one or more nucleic acids are linked by ester bonding. The nucleic acid polymers may be composed of DNA, RNA or a combination thereof and encompass both naturally-occurring and non-naturally occurring nucleic acid polymers.

The terms "polypeptide", "peptide", and "protein" are used interchangeably herein to refer to a polymer of amino acid residues. The term refers to naturally occurring and synthetic amino acids, as well as amino acids analogs and amino acids mimetics, amino acid polymers in which one or more amino acid residue is a modified residue, or a non-naturally occurring residue, such as an artificial chemical mimetic of a corresponding naturally occurring amino acid. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids. Amino acids may be referred to herein by their commonly known three letter symbols or the one-letter symbols recommended by the IUPAC-IUB Biochemical Nomenclature Commission.

Unless otherwise defined, the terms "cancer" refers to cancers over-expressing the DEPDC1 gene. Examples of cancers over-expressing DEPDC1 include, but are not limited to, bladder cancer.

II. Genes And Proteins

The nucleic acid and polypeptide sequences of genes of interest to the present invention are shown in the following numbers, but not limited to those;

DEPDC1: SEQ ID NO: 44 and 45, or 46 and 47;
ZNF224: SEQ ID NO: 48 and 49;
DLG1: SEQ ID NO: 50 and 51; and
A20 (TNFAIP3): SEQ ID NO: 52 and 53.

Additional sequence data is available via following accession numbers;

DEPDC1: AB382287 or NM_017779.4;
ZNF224: NM_013398;
DLG1: NM_001098424; and
A20 (TNFAIP3): NM_006290.

According to an aspect of the present invention, functional equivalents are also considered to be above "polypeptides". Herein, a "functional equivalent" of a protein is a polypeptide that has a biological activity equivalent to the protein. Namely, any polypeptide that retains the biological ability of the original peptide may be used as such a functional equivalent in the present invention. Such functional equivalents include those wherein one or more amino acids are substituted, deleted, added, or inserted to the natural occurring amino acid sequence of the protein. Alternatively, the polypeptide may be composed an amino acid sequence having at least about 80% homology (also referred to as sequence identity) to the sequence of the respective protein, more preferably at least about 90% to 95% homology, even more preferably 96% to 99% homology. In other embodiments, the polypeptide can be encoded by a polynucleotide that hybridizes under stringent conditions to the naturally occurring nucleotide sequence of the gene.

A polypeptide of the present invention may have variations in amino acid sequence, molecular weight, isoelectric point, the presence or absence of sugar chains, or form, depending on the cell or host used to produce it or the purification method utilized. Nevertheless, so long as it has a function equivalent to that of the human protein of the present invention, it is within the scope of the present invention.

The phrase "stringent (hybridization) conditions" refers to conditions under which a nucleic acid molecule will hybridize to its target sequence, typically in a complex mixture of nucleic acids, but not detectably to other sequences. Stringent conditions are sequence-dependent and will vary in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10 degrees C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may also be achieved with the addition of destabilizing agents such as formamide. For selective or specific hybridization, a positive signal is at least two times of background, preferably 10 times of background hybridization. Exemplary stringent hybridization conditions include the following: 50% formamide, 5×SSC, and 1% SDS, incubating at 42 degrees C., or, 5×SSC, 1% SDS, incubating at 65 degrees C., with wash in 0.2×SSC, and 0.1% SDS at 50 degrees C.

In the context of the present invention, a condition of hybridization for isolating a DNA encoding a polypeptide functionally equivalent to the above human protein can be routinely selected by a person skilled in the art. For example, hybridization may be performed by conducting pre-hybridization at 68 degrees C. for 30 min or longer using "Rapid-hyb buffer" (Amersham LIFE SCIENCE), adding a labeled probe, and warming at 68 degrees C. for 1 hour or longer. The following washing step can be conducted, for example, in a low stringent condition. An exemplary low stringent condition may include 42 degrees C., 2×SSC, 0.1% SDS, preferably 50 degrees C., 2×SSC, 0.1% SDS. High stringency conditions are often preferably used. An exemplary high stringency condition may include washing 3 times in 2×SSC, 0.01% SDS at room temperature for 20 min, then washing 3 times in 1×SSC, 0.1% SDS at 37 degrees C. for 20 min, and washing twice in 1×SSC, 0.1% SDS at 50 degrees C. for 20 min. However, several factors, such as temperature and salt concentration, can influence the stringency of hybridization and one skilled in the art can suitably select the factors to achieve the requisite stringency.

In general, modification of one, two or more amino acid in a protein will not influence the function of the protein. In fact, mutated or modified proteins (i.e., peptides composed of an amino acid sequence in which one, two, or several amino acid residues have been modified through substitution, deletion, insertion and/or addition) have been known to retain the original biological activity (Mark et al., Proc Natl Acad Sci USA 81: 5662-6 (1984); Zoller and Smith, Nucleic Acids Res 10:6487-500 (1982); Dalbadie-McFarland et al., Proc Natl Acad Sci USA 79: 6409-13 (1982)). Thus, in one embodiment, the peptides of the present invention may have an amino acid sequence wherein one, two or even more amino acids are added, inserted, deleted, and/or substituted in a reference sequence.

Those of skill in the art will recognize that individual additions, deletions, insertions, or substitutions to an amino acid sequence which alter a single amino acid or a small percentage of amino acids or those considered to be a "conservative modifications", i.e., one wherein the alteration results in the conservation of properties of the original amino acid side chain(s), tend to result in the generation of a protein having functions similar to those of the original reference protein. As such are acceptable in the context of the instant invention.

So long as the activity the protein is maintained, the number of amino acid mutations is not particularly limited. However, it is generally preferred to alter 5% or less of the amino acid sequence. Accordingly, in a preferred embodiment, the number of amino acids to be mutated in such a mutant is generally 30 amino acids or less, preferably 20 amino acids or less, more preferably 10 amino acids or less, more preferably 5 or 6 amino acids or less, and even more preferably 3 or 4 amino acids or less.

An amino acid residue to be mutated is preferably mutated into a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Conservative substitution tables providing functionally similar amino acids are well known in the art. For example, the following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified polypeptides are included in the present protein. However, the present invention is not restricted thereto and includes non-conservative modifications, so long as at least one biological activity of the protein is retained. Furthermore, the modified proteins do not exclude polymorphic variants, interspecies homologues, and those encoded by alleles of these proteins.

Moreover, the gene of the present invention encompasses polynucleotides that encode such functional equivalents of the protein. In addition to hybridization, a gene amplification method, for example, the polymerase chain reaction (PCR) method, can be utilized to isolate a polynucleotide encoding a polypeptide functionally equivalent to the protein, using a primer synthesized based on the sequence above information. Polynucleotides and polypeptides that are functionally equivalent to the human gene and protein, respectively, normally have a high homology to the originating nucleotide or amino acid sequence of. "High homology" typically refers to a homology of 40% or higher, preferably 60% or higher, more preferably 80% or higher, even more preferably 90% to 95% or higher, even more preferably 96% to 99% or higher. The homology of a particular polynucleotide or polypeptide can be determined by following the algorithm in "Wilbur and Lipman, Proc Natl Acad Sci USA 80: 726-30 (1983)".

III. DEPDC1 Mutant Polypeptide:

Dominant negative mutants of the proteins disclosed here can be used to treat or prevent cancer wherein the cancer is bladder cancer. For example, the present invention provides methods for treating or preventing cancer in a subject by administering a DEPDC1 mutant having a dominant negative effect, or a polynucleotide encoding such a mutant. The DEPDC1 mutant may include an amino acid sequence that includes a ZNF224 binding region (see FIGS. 4 and 5). The DEPDC1 mutant may have the amino acid sequence of SEQ ID NO: 28 corresponding to positions 611-628 of SEQ ID NO: 45 or 327-344 of SEQ ID NO: 47.

The present invention also provides a polypeptide including the sequence PPNRRK-LQLLMRMISRMS (SEQ ID NO: 28); or an amino acid sequence of a polypeptide functionally equivalent to the polypeptide, wherein the polypeptide lacks the biological function of a peptide consisting of SEQ ID NO: 45 or 47. In a preferred embodiment, the biological function to be deleted is an activity to promote a cell proliferation of cancer cell. The length of the polypeptide of the present invention may be less than the full length DEPDC1 (SEQ ID NO: 45 or 47; 811 or 527 residues). Generally, polypeptides of the present invention may have less than 200 amino acid residues, preferably less than 100 amino acid residues, more preferably 10-50, alternatively 8-30 amino acid residues.

The polypeptides of the present invention encompass modified polypeptides. In the present invention, the term "modified" refers, for example, to binding with other substances. Accordingly, in the context of the present invention, a polypeptide may further include other substances such as a cell-membrane permeable substance. Examples of other substances include, but are not limited to, organic compounds such as peptides, lipids, saccharides, and various naturally-occurring or synthetic polymers. The polypeptides of the present invention may have any number of modifications so long as the resulting polypeptide retains the desired activity of inhibiting the binding of DEPDC1 to ZNF224. In some embodiments, the inhibitory polypeptides can directly compete with DEPDC1 binding to ZNF224. Modifications can also confer additive functions on the polypeptides of the invention. Examples of the additive functions include targetability, deliverability, and stabilization.

In some preferred embodiments, the DEPDC1 mutant may be linked to a membrane transducing agent. A number of peptide sequences have been characterized for their ability to translocate into live cells and can be used for this purpose in the present invention. Such membrane transducing agents (typically peptides) are defined by their ability to reach the cytoplasmic and/or nuclear compartments in live cells after internalization. Examples of proteins from which transducing agents may be derived include HIV Tat transactivator 1 and 2, and the *Drosophila melanogaster* transcription factor Antennapedia3. In addition, nonnatural peptides with transducing activity have been used. These peptides are typically small peptides known for their membrane-interacting properties which are tested for translocation. The hydrophobic region within the secretion signal sequence of K-fibroblast growth factor (FGF), the venom toxin mastoparan (transportan)13, and Buforin I14 (an amphibian antimicrobial peptide) have been shown to be useful as transducing agents. For a review of transducing agents useful in the context of the present invention, see Joliot et al. Nature Cell Biology 6:189-96 (2004).

The DEPDC1 mutant may have the general formula:

$$[R]-[D],$$

wherein [R] is a membrane transducing agent, and [D] is a polypeptide having the amino acid sequence of SEQ ID NO: 28. In the general formula, [R] may directly link with [D], or be indirectly linked with [D] through a linker. Peptides or compounds having plural functional groups may be used as the linker. Specifically, an amino acid sequence of -GGG- may be used as the linker. Alternatively, the membrane transducing agent and the polypeptide having the amino acid sequence of SEQ ID NO: 28 can bind to the surface of a micro-particle.

In the context of the present invention, [R] may link with arbitral region of [D]. For example, [R] may link with N-terminus or C-terminus of [D], or side chain of the amino acid residues constituting [D]. Furthermore, plural molecules of [R] may also link with one molecule of [D]. In some embodiments, plural molecules of [R]s may link with different site of [D]. In another embodiments, [D] may be modified with some [R]s linked together.

The membrane transducing agent can be selected from group listed below;

[poly-arginine]; Matsushita, M. et al, J Neurosci. 21, 6000-7 (2003).

[Tat/RKKRRQRRR] (SEQ ID NO: 29) Frankel, A. et al, Cell 55, 1189-93 (1988).

Green, M. & Loewenstein, P. M. Cell 55, 1179-88 (1988).
[Penetratin/RQIKIWFQNRRMKWKK] (SEQ ID NO: 30)
Derossi, D. et al, J. Biol. Chem. 269, 10444-50 (1994).
[Buforin II/TRSSRAGLQFPVGRVHRLLRK] (SEQ ID NO: 31)
Park, C. B. et al. Proc. Natl. Acad. Sci. USA 97, 8245-50 (2000).
[Transportan/GWTLNSAGYLLGKINLKALAALAK-KIL] (SEQ ID NO: 32)
Pooga, M. et al. FASEB J. 12, 67-77 (1998).
[MAP (model amphipathic peptide)/KLALKLALKAL-KAALKLA] (SEQ ID NO: 33)
Oehlke, J. et al. Biochim. Biophys. Acta. 1414, 127-39 (1998).
[K-FGF/AAVALLPAVLLALLAP] (SEQ ID NO: 34)
Lin, Y. Z. et al. J. Biol. Chem. 270, 14255-14258 (1995).
[Ku70/VPMLK] (SEQ ID NO: 35)
Sawada, M. et al. Nature Cell Biol. 5, 352-7 (2003).
[Ku70/PMLKE] (SEQ ID NO: 36)
Sawada, M. et al. Nature Cell Biol. 5, 352-7 (2003).
[Prion/MANLGYWLLALFVTMWTDVGLCKKRPKP] (SEQ ID NO: 37)
Lundberg, P. et al. Biochem. Biophys. Res. Commun. 299, 85-90 (2002).
[pVEC/LLIILRRRIRKQAHAHSK] (SEQ ID NO: 38)
Elmquist, A. et al. Exp. Cell Res. 269, 237-44 (2001).
[Pep-1/KETWWETWWTEWSQPKKKRKV] (SEQ ID NO: 39)
Morris, M. C. et al. Nature Biotechnol. 19, 1173-6 (2001).
[SynB1/RGGRLSYSRRRFSTSTGR] (SEQ ID NO: 40)
Rousselle, C. et al. Mol. Pharmacol. 57, 679-86 (2000).
[Pep-7/SDLWEMMMVSLACQY] (SEQ ID NO: 41)
Gao, C. et al. Bioorg. Med. Chem. 10, 4057-65 (2002).
[HN-1/TSPLNIHNGQKL] (SEQ ID NO: 42)
Hong, F. D. & Clayman, G. L. Cancer Res. 60, 6551-6 (2000).

In the context of the present invention, the number of arginine residues that constitute the poly-arginine is not limited, though in some preferred embodiments, 5 to 20 contiguous arginine residues may be exemplified. In a preferred embodiment, the number of arginine residues of the poly-arginine is 11 (SEQ ID NO: 43).

As used herein, the phrase "dominant negative fragment of DEPDC1" refers to a mutated form of DEPDC1 that is capable of complexing with ZNF224. Thus, a dominant negative fragment is one that is not functionally equivalent to the full length DEPDC1 polypeptide. Preferred dominant negative fragments are those that include a ZNF224 binding region.

In another embodiment, the present invention provides for the use of a polypeptide having the sequence PPNR-RKLQLLMRMISRMS (SEQ ID NO: 28); a polypeptide functionally equivalent to such a polypeptide; or polynucleotide encoding those polypeptides in manufacturing a pharmaceutical composition for treating or preventing cancer, wherein the polypeptide lacks the biological function of a peptide consisting of SEQ ID NO: 45 or 47. Moreover, in another embodiments, the present invention also provides an agent for either or both of treating and preventing cancer including as an active ingredient a polypeptide that includes the sequence PPNRRK-LQLLMRMISRMS (SEQ ID NO: 28); a polypeptide functionally equivalent to the polypeptide; or polynucleotide encoding those polypeptides, wherein the polypeptide lacks the biological function of a peptide of SEQ ID NO: 45 or 47. Alternatively, the present invention also provides a pharmaceutical composition for treating or preventing cancer, including a polypeptide composed of the sequence PPNRRK-LQLLMRMISRMS (SEQ ID NO: 28); or a polypeptide functionally equivalent to the polypeptide; and a pharmaceutically acceptable carrier, wherein the polypeptide lacks the biological function of a peptide of SEQ ID NO: 45 or 47.

When the polypeptides of the present invention are administered, for example as a prepared pharmaceutical, to human and other mammals, such as mouse, rat, guinea pig, rabbit, cat, dog, sheep, pig, cattle, monkey, baboon and chimpanzee, for treating cancer or inducing apoptosis in cells, isolated compounds can be administered directly, or formulated into an appropriate dosage form using known methods for preparing pharmaceuticals. For example, if necessary, the pharmaceuticals can be administered in an injectable form that is a sterilized solution or suspension with water or any other pharmaceutically acceptable liquid. For example, the compounds can be mixed with pharmacologically acceptable carriers or media, specifically sterilized water, physiological saline, plant oil, emulsifier, suspending agent, surfactant, stabilizer, corrigent, excipient, vehicle, preservative, and binder, in a unit dosage form necessary for producing a generally accepted pharmaceutical. Depending on the amount of active ingredient in these formulations, a suitable dose within the specified range can be determined.

One skilled in the art can readily determine an effective amount of polypeptide to be administered to a given subject, by taking into account factors such as body weight, age, sex, type of disease, symptoms and other conditions of the subject; the route of administration; and whether the administration is regional or systemic.

Although dosages may vary according to the symptoms, an exemplary dose of an polypeptide or an active fragment thereof for treating or preventing cancer is about 0.1 mg to about 100 mg per day, preferably about 1.0 mg to about 50 mg per day and more preferably about 1.0 mg to about 20 mg per day, when administered orally to a normal adult (weight 60 kg).

When the compound is parenterally administered to a normal adult (body weight 60 kg) in injectable form, it is convenient to intravenously inject a dose of about 0.01 mg to about 30 mg/day, preferably about 0.1 mg to about 20 mg/day, more preferably about 0.1 mg to about 10 mg/day, although it is slightly varied depending on patients, target organs, symptoms, and administration methods. Similarly, the compound can be administered to other animals in an amount converted from the dose for the body weight of 60 kg.

It is contemplated that greater or smaller amounts of the peptide can be administered. The precise dosage required for a particular circumstance may be readily and routinely determined by one of skill in the art.

The present invention further provides a method or process for manufacturing a pharmaceutical composition for treating a cancer over-expressing DEPDC1, such as bladder cancer, such a method or process including the step of admixing an active ingredient with a pharmaceutically or physiologically acceptable carrier, wherein the active ingredient is a polypeptide including the sequence PPNRRKLQLLMRMISRMS (SEQ ID NO: 28); or a polypeptide functionally equivalent to the polypeptide.

IV. Screening For An Anti-Cancer Compound:

In the context of the present invention, agents to be identified through the present screening methods include any compound or composition, including several compounds. Furthermore, the test agent or compound exposed to a cell or protein according to the screening methods of the present invention may be a single compound or a combination of compounds. When a combination of compounds is used in the methods, the compounds may be contacted sequentially or simultaneously.

Any test agent or compound, for example, cell extracts, cell culture supernatant, products of fermenting microorganism, extracts from marine organism, plant extracts, purified or crude proteins, peptides, non-peptide compounds, synthetic micromolecular compounds (including nucleic acid constructs, such as antisense RNA, siRNA, Ribozymes, and aptamer etc.) and natural compounds can be used in the screening methods of the present invention. The test agent or compound of the present invention can be also obtained using any of the numerous approaches in combinatorial library methods known in the art, including (1) biological libraries, (2) spatially addressable parallel solid phase or solution phase libraries, (3) synthetic library methods requiring deconvolution, (4) the "one-bead one-compound" library method and (5) synthetic library methods using affinity chromatography selection. The biological library methods using affinity chromatography selection is limited to peptide libraries, while the other four approaches are applicable to peptide, non-peptide oligomer or small molecule libraries of compounds (Lam, Anticancer Drug Des 1997, 12: 145-67). Examples of methods for the synthesis of molecular libraries can be found in the art (DeWitt et al., Proc Natl Acad Sci USA 1993, 90: 6909-13; Erb et al., Proc Natl Acad Sci USA 1994, 91: 11422-6; Zuckermann et al., J Med Chem 37: 2678-85, 1994; Cho et al., Science 1993, 261: 1303-5; Carell et al., Angew Chem Int Ed Engl 1994, 33: 2059; Carell et al., Angew Chem Int Ed Engl 1994, 33: 2061; Gallop et al., J Med Chem 1994, 37: 1233-51). Libraries of compounds may be presented in solution (see Houghten, Bio/Techniques 1992, 13: 412-21) or on beads (Lam, Nature 1991, 354: 82-4), chips (Fodor, Nature 1993, 364: 555-6), bacteria (U.S. Pat. No. 5,223,409), spores (U.S. Pat. Nos. 5,571,698; 5,403,484, and 5,223,409), plasmids (Cull et al., Proc Natl Acad Sci USA 1992, 89: 1865-9) or phage (Scott and Smith, Science 1990, 249: 386-90; Devlin, Science 1990, 249: 404-6; Cwirla et al., Proc Natl Acad Sci USA 1990, 87: 6378-82; Felici, J Mol Biol 1991, 222: 301-10; US Pat. Application 2002103360).

A compound in which a part of the structure of the compound screened by any of the present screening methods is converted by addition, deletion and/or replacement, is included in the agents obtained by the screening methods of the present invention.

Furthermore, when the screened test agent or compound is a protein, for obtaining a DNA encoding the protein, either the whole amino acid sequence of the protein may be determined to deduce the nucleic acid sequence coding for the protein, or partial amino acid sequence of the obtained protein may be analyzed to prepare an oligo DNA as a probe based on the sequence, and screen cDNA libraries with the probe to obtain a DNA encoding the protein. The obtained DNA is confirmed it's usefulness in preparing the test agent or compound which is a candidate for treating or preventing cancer.

Test agents or compounds useful in the screenings described herein can also be antibodies that specifically bind to DEPDC1 or ZNF224 protein or partial peptides thereof that lack the biological activity of the original proteins in vivo.

Although the construction of test agent/compound libraries is well known in the art, herein below, additional guidance in identifying test agents or compounds and construction libraries of such agents for the present screening methods are provided.

(i) Molecular Modeling:

Construction of test agent/compound libraries is facilitated by knowledge of the molecular structure of compounds known to have the properties sought, and/or the molecular structure of DEPDC1 or ZNF224. One approach to preliminary screening of test agents or compounds suitable for further evaluation utilizes computer modeling of the interaction between the test agent/compound and its target.

Computer modeling technology allows for the visualization of the three-dimensional atomic structure of a selected molecule and the rational design of new compounds that will interact with the molecule. The three-dimensional construct typically depends on data from x-ray crystallographic analysis or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

An example of the molecular modeling system described generally above includes the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles have been published on the subject of computer modeling of drugs interactive with specific proteins, examples of which include Rotivinen et al. Acta Pharmaceutica Fennica 1988, 97: 159-66; Ripka, New Scientist 1988, 54-8; McKinlay & Rossmann, Annu Rev Pharmacol Toxiciol 1989, 29: 111-22; Perry & Davies, Prog Clin Biol Res 1989, 291: 189-93; Lewis & Dean, Proc R Soc Lond 1989, 236: 125-40, 141-62; and, with respect to a model receptor for nucleic acid components, Askew et al., J Am Chem Soc 1989, 111: 1082-90.

Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. See, e.g., DesJarlais et al., Med Chem 1988, 31: 722-9; Meng et al., J Computer Chem 1992, 13: 505-24; Meng et al., Proteins 1993, 17: 266-78; Shoichet et al., Science 1993, 259: 1445-50.

Once a putative inhibitor has been identified, combinatorial chemistry techniques can be employed to construct any number of variants based on the chemical structure of the identified putative inhibitor, as detailed below. The resulting library of putative inhibitors, or "test agents or compounds" may be screened using the methods of the present invention to identify test agents or compounds the treatment and/or prophylaxis of cancer and/or the prevention of post-operative recurrence of cancer, particularly wherein the cancer is bladder cancer.

(ii) Combinatorial Chemical Synthesis:

Combinatorial libraries of test agents or compounds may be produced as part of a rational drug design program involving knowledge of core structures existing in known inhibitors. This approach allows the library to be maintained at a reasonable size, facilitating high throughput screening. Alternatively, simple, particularly short, polymeric molecular libraries may be constructed by simply synthesizing all permutations of the molecular family making up the library. An example of this latter approach would be a library of all peptides six amino acids in length. Such a peptide library could include every 6 amino acid sequence permutation. This type of library is termed a linear combinatorial chemical library.

Preparation of Combinatorial Chemical Libraries is Well Known to Those of Skill in the art, and may be generated by either chemical or biological synthesis. Combinatorial chemical libraries include, but are not limited to, peptide libraries (see, e.g., U.S. Pat. No. 5,010,175; Furka, Int J Pept Prot Res 1991, 37: 487-93; Houghten et al., Nature 1991, 354: 84-6). Other chemistries for generating chemical diversity libraries can also be used. Such chemistries include, but are not limited to: peptides (e.g., PCT Publication No. WO 91/19735), encoded peptides (e.g., WO 93/20242), random bio-oligomers (e.g., WO 92/00091), benzodiazepines (e.g., U.S. Pat. No. 5,288,514), diversomers such as hydantoins, benzodiazepines and dipeptides (DeWitt et al., Proc Natl Acad Sci USA 1993, 90:6909-13), vinylogous polypeptides (Hagihara et al., J Amer Chem Soc 1992, 114: 6568), non-peptidal peptidomimetics with glucose scaffolding (Hirschmann et al., J Amer Chem Soc 1992, 114: 9217-8), analogous organic syntheses of small compound libraries (Chen et al., J. Amer Chem Soc 1994, 116: 2661), oligocarbamates (Cho et al., Science 1993, 261: 1303), and/or peptidylphosphonates (Campbell et al., J Org Chem 1994, 59: 658), nucleic acid libraries (see Ausubel, Current Protocols in Molecular Biology 1995 supplement; Sambrook et al., Molecular Cloning: A Laboratory Manual, 1989, Cold Spring Harbor Laboratory, New York, USA), peptide nucleic acid libraries (see, e.g., U.S. Pat. No. 5,539,083), antibody libraries (see, e.g., Vaughan et al., Nature Biotechnology 1996, 14(3):309-14 and PCT/US96/10287), carbohydrate libraries (see, e.g., Liang et al., Science 1996, 274: 1520-22; U.S. Pat. No. 5,593,853), and small organic molecule libraries (see, e.g., benzodiazepines, Gordon E M. Curr Opin Biotechnol. 1995 Dec. 1; 6(6):624-31.; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

(iii) Other Candidates:

Another approach uses recombinant bacteriophage to produce libraries. Using the "phage method" (Scott & Smith, Science 1990, 249: 386-90; Cwirla et al., Proc Natl Acad Sci USA 1990, 87: 6378-82; Devlin et al., Science 1990, 249: 404-6), very large libraries can be constructed (e.g., 106-108 chemical entities). A second approach uses primarily chemical methods, of which the Geysen method (Geysen et al., Molecular Immunology 1986, 23: 709-15; Geysen et al., J Immunologic Method 1987, 102: 259-74); and the method of Fodor et al. (Science 1991, 251: 767-73) are examples. Furka et al. (14th International Congress of Biochemistry 1988, Volume #5, Abstract FR:013; Furka, Int J Peptide Protein Res 1991, 37: 487-93), Houghten (U.S. Pat. No. 4,631,211) and Rutter et al. (U.S. Pat. No. 5,010,175) describe methods to produce a mixture of peptides that can be tested as agonists or antagonists.

Aptamers are macromolecules composed of nucleic acid that bind tightly to a specific molecular target. Tuerk and Gold (Science. 249:505-510 (1990)) discloses SELEX (Systematic Evolution of Ligands by Exponential Enrichment) method for selection of aptamers. In the SELEX method, a large library of nucleic acid molecules {e.g., $10^{15}$ different molecules) can be used for screening.

V. Screening for a compound that decreases the binding between DEPDC1 AND ZNF224:

In the context of the present invention, the interaction between DEPDC1 and ZNF224 is confirmed by immunoprecipitation (FIG. 1B). Accordingly, the present invention provides a method of screening for a compound that inhibits the binding between DEPDC1 and ZNF224. A compound that inhibits the binding between DEPDC1 and ZNF224 is expected to suppress the proliferation of cancer cells expressing DEPDC1 is useful for treating or preventing cancer relating to DEPDC1. Therefore, the present invention also provides a method for screening a compound that inhibits the binding between DEPDC1 and ZNF224 and suppresses the proliferation of the cancer cells, and a method for screening a compound for treating or preventing the cancer, particularly wherein the cancer is bladder cancer.

More specifically, the method of the present invention includes the steps of:

(a) contacting DEPDC1 polypeptide, or functional equivalent thereof, with ZNF224 polypeptide, or functional equivalent thereof, in the presence of a test compound;

(b) detecting the binding between the polypeptides; and (c) selecting the test compound that inhibits the binding between the polypeptides.

According to the present invention, the therapeutic effect of the test agent or compound on inhibiting the cell growth or a candidate agent or compound for treating or preventing DEPDC1 associating disease may be evaluated. Therefore, the present invention also provides a method for screening a candidate agent or compound that suppresses the proliferation of cancer cells, and a method for screening a candidate agent or compound for treating or preventing cancer.

More specifically, the method includes the steps of:

(a) contacting a DEPDC1 polypeptide, or functional equivalent thereof, with a ZNF224 polypeptide, or functional equivalent thereof, in the presence of a test agent or compound;

(b) detecting the level of binding between the polypeptides; and (c) comparing the binding level of the DEPDC1 and ZNF224 proteins with that detected in the absence of the test agent or compound; and (d) correlating the binding level of c) with the therapeutic effect of the test agent or compound.

In the context of the present invention, the therapeutic effect may be correlated with the binding level of the DEPDC1 and ZNF224 proteins. For example, when the test agent or compound reduces the level of binding of DEPDC1 and ZNF224 proteins as compared to a level detected in the absence of the test agent or compound, the test agent or compound may identified or selected as the candidate agent or compound having the therapeutic effect. Alternatively, when the test agent or compound does not reduce the binding level of DEPDC1 and ZNF224 proteins as compared to a level detected in the absence of the test agent or compound, the test agent or compound may identified as the agent or compound having no significant therapeutic effect.

The phrase "functional equivalent of DEPDC1 polypeptide" as used herein refers to a polypeptide that includes amino acid sequence of ZNF224 binding domain. Preferably, the ZNF224 binding domain includes an amino acid sequence selected from the group of SEQ ID NO: 28, 54 and 55, including 141-300, 300-669 or 587-740 of SEQ ID NO: 45. Similarly, the term "functional equivalent of ZNF224 polypeptide" refers to a polypeptide that includes amino acid sequence of DEPDC1 binding domain.

The method of the present invention is described in further detail below.

As a method of screening for compounds that inhibit binding between DEPDC1 and ZNF224 many methods well known by one skilled in the art can be used. Such a screening can be carried out as an in vitro assay system. More specifically, first, a DEPDC1 polypeptide is bound to a support, and ZNF224 polypeptide is added thereto together with a test compound. Next, the mixture is incubated, washed and ZNF224 polypeptide bound to the support is detected and/or measured. Promising candidate compounds can reduce the amount of detecting ZNF224 polypeptide.

Alternatively, a ZNF224 polypeptide may be bound to a support and DEPDC1 polypeptide may be added. Herein, DEPDC1 and ZNF224 can be prepared not only as natural proteins but also as recombinant proteins prepared by the gene recombination technique. The natural proteins can be prepared, for example, by affinity chromatography. On the other hand, the recombinant proteins may be prepared by culturing cells transformed with DNA encoding DEPDC1 or ZNF224 to express the protein therein and then recovering it.

Examples of supports that may be used for binding proteins include insoluble polysaccharides, such as agarose, cellulose and dextran; and synthetic resins, such as polyacrylamide, polystyrene and silicon; preferably commercial available beads and plates (e.g., multi-well plates, biosensor chip, etc.) prepared from the above materials may be used. When using beads, they may be filled into a column. Alternatively, the use of magnetic beads of also known in the art, and enables to readily isolate proteins bound on the beads via magnetism.

The binding of a protein to a support may be conducted according to routine methods, such as chemical bonding and physical adsorption. Alternatively, a protein may be bound to a support via antibodies specifically recognizing the protein. Moreover, binding of a protein to a support can be also conducted by means of avidin and biotin. The binding between proteins is carried out in buffer, for example, but are not limited to, phosphate buffer and Tris buffer, as long as the buffer does not inhibit binding between the proteins.

In the context of the present invention, a biosensor using the surface plasmon resonance phenomenon may be used as a mean for detecting or quantifying the bound protein. When such a biosensor is used, the interaction between the proteins can be observed in real-time, as a surface plasmon resonance signal, using only a minute amount of polypeptide and without labeling (for example, BIAcore, Pharmacia). Therefore, it is possible to evaluate binding between DEPDC1 and ZNF224 using a biosensor such as BIAcore.

Alternatively, DEPDC1 or ZNF224 may be labeled, and the label of the polypeptide may be used to detect or measure the binding activity. Specifically, after pre-labeling one of the polypeptide, the labeled polypeptide is contacted with the other polypeptide in the presence of a test compound, and then bound polypeptide are detected or measured according to the label after washing. Labeling substances such as radioisotope (e.g., 3H, $^{14}$C, $^{32}$P, $^{33}$P, $^{35}$S, $^{125}$I, $^{131}$I), enzymes (e.g., alkaline phosphatase, horseradish peroxidase, beta-galactosidase, b-glucosidase), fluorescent substances (e.g., fluorescein isothiocyanate (FITC), rhodamine) and biotin/avidin, may be used for the labeling of a protein in the present method. When the protein is labeled with radioisotope, the detection or measurement can be carried out by liquid scintillation. Alternatively, proteins labeled with enzymes can be detected or measured by adding a substrate of the enzyme to detect the enzymatic change of the substrate, such as generation of color, with absorptiometer. Further, in case where a fluorescent substance is used as the label, the bound protein may be detected or measured using fluorophotometer.

Furthermore, binding between DEPDC1 and ZNF224 can be also detected or measured using antibodies to DEPDC1 or ZNF224. For example, after contacting a DEPDC1 polypeptide immobilized on a support with a test compound and a ZNF224 polypeptide mixture is incubated and washed, and detection or measurement can be conducted using an antibody against the ZNF224 polypeptide.

Alternatively, a ZNF224 polypeptide may be immobilized on a support, and an antibody against DEPDC1 may be used as the antibody. In case of using an antibody in the context of the present screening, the antibody is preferably labeled with one of the labeling substances mentioned above, and detected or measured based on the labeling substance. Alternatively, the antibody against the DEPDC1 or ZNF224 polypeptide may be used as a primary antibody to be detected with a secondary antibody that is labeled with a labeling substance. Furthermore, the antibody bound to the protein in the screening of the present invention may be detected or measured using protein G or protein A column.

Alternatively, in another embodiment of the screening method of the present invention, a two-hybrid system utilizing cells may be used ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); the references "Dalton and Treisman, Cell 68: 597-612 (1992)", "Fields and Sternglanz, Trends Genet. 10: 286-92 (1994)").

In the two-hybrid system, for example, a DEPDC1 polypeptide is fused to the SRF-binding region or GAL4-binding region and expressed in yeast cells. A ZNF224 polypeptide that binds to a DEPDC1 polypeptide that binds to a ZNF224 polypeptide is fused to the VP16 or GAL4 transcriptional activation region and also expressed in the yeast cells in the existence of a test compound. Alternatively, a DEPDC1 polypeptide may be fused to the SRF-binding region or GAL4-binding region, and a ZNF224 polypeptide to the VP16 or GAL4 transcriptional activation region. The binding of the two activates a reporter gene, making positive clones detectable. As a reporter gene, for example, Ade2 gene, lacZ gene, CAT gene, luciferase gene and such can be used besides HIS3 gene.

VI. Screening For A Compound Altering The Expression Of DLG1 OR A20 (TNFAIP3):

In the context of the present invention, the expression of DLG1 or A20 (TNFAIP3) was increased by siRNA of DEPDC1 or ZNF224 (FIG. 3A). Moreover, the increase of DLG1 or A20 (TNFAIP3) by dominantnegative protein of DEPDC1 related to cell cycle (FIG. 6). Therefore, the present invention provides a method of screening for a compound that suppresses the proliferation of cancer cells expressing DEPDC1 and ZNF224 or a compound that is useful for treating or preventing cancer relating to DEPDC1, particularly wherein the cancer is bladder cancer. In the context of the present invention, such screening may include, for example, the following steps: (a) contacting a candidate compound with a cell expressing DEPDC1 and ZNF224 and (b) selecting the candidate compound that increases the expression level of DLG1 or A20 (TNFAIP3) in comparison with the expression level detected in the absence of the test compound.

According to the present invention, the therapeutic effect of the test agent or compound on inhibiting the cell growth or a candidate agent or compound for treating or preventing DEPDC1 associating disease may be evaluated. Therefore, the present invention also provides a method for screening a candidate agent or compound that suppresses the proliferation of cancer cells, and a method for screening a candidate agent or compound for treating or preventing DEPDC1 associating disease.

In the context of the present invention, such screening may include, for example, the following steps:

a) contacting a test agent or compound with a cell expressing the DEPDC1 and ZNF224 genes;

b) detecting the expression level of the DLG1 or A20 (TNFAIP3) gene; and c) correlating the expression level of b) with the therapeutic effect of the test agent or compound.

In the context of the present invention, the therapeutic effect may be correlated with the expression level of the DLG1 or A20 (TNFAIP3) gene. For example, when the test agent or compound increases the expression level of the DLG1 or A20 (TNFAIP3) gene as compared to a level detected in the absence of the test agent or compound, the test agent or compound may identified or selected as the candidate agent or compound having the therapeutic effect. Alternatively, when the test agent or compound does not increase the expression level of the DLG1 or A20 (TNFAIP3) gene as compared to a level detected in the absence of the test agent or compound, the test agent or compound may identified as the agent or compound having no significant therapeutic effect.

The method of the present invention will be described in more detail below.

Cells expressing DEPDC1 and ZNF224 include, for example, cell lines established from bladder cancer or by transfection with DEPDC1 and ZNF224 expression vectors. The expression level can be estimated by methods well known to one skilled in the art, for example, RT-PCR, Northern bolt assay, Western bolt assay, immunostaining and flow cytometry analysis. "increase the expression level" as defined herein are preferably at least 110% reduction of expression level of DLG1 or A20 (TNFAIP3) in comparison to the expression level in absence of the compound, more preferably at least 125%, 150% or 175% reduced level and most preferably at 200% reduced level. The compound herein includes chemical compound, double-strand nucleotide of DEPDC1 or ZNF224, and so on. In the method of screening, a compound that increases the expression level of DLG1 or A20 (TNFAIP3) can be selected as candidate compounds to be used for the treatment or prevention of cancer.

Alternatively, the screening method of the present invention may include the following steps:

(a) contacting a candidate compound with a cell expressing DEPDC1 and ZNF224 into which a vector, housing the transcriptional regulatory region of DLG1 or A20 (TNFAIP3) and a reporter gene that is expressed under the control of the transcriptional regulatory region, has been introduced;

(b) measuring the expression or activity of the reporter gene; and (c) selecting a candidate compound that increases the expression or activity level of the reporter gene as compared to a control.

According to the present invention, the therapeutic effect of the test agent or compound on inhibiting the cell growth or a candidate agent or compound for treating or preventing DEPDC1 associating disease may be evaluated. Therefore, the present invention also provides a method for screening a candidate agent or compound that suppresses the proliferation of cancer cells, and a method for screening a candidate agent or compound for treating or preventing a DEPDC1 associated disease.

In the context of the present invention, such screening may include, for example, the following steps:

a) contacting a test agent or compound with a cell into which a vector, housing the transcriptional regulatory region of the DLG1 or A20 (TNFAIP3) gene and a reporter gene that is expressed under the control of the transcriptional regulatory region, has been introduced;

b) detecting the expression or activity of said reporter gene; and c) correlating the expression level of b) with the therapeutic effect of the test agent or compound.

In the context of the present invention, the therapeutic effect may be correlated with the expression or activity of said reporter gene. For example, when the test agent or compound increases the expression or activity of said reporter gene as compared to a level detected in the absence of the test agent or compound, the test agent or compound may identified or selected as the candidate agent or compound having the therapeutic effect. Alternatively, when the test agent or compound does not increase the expression or activity of said reporter gene as compared to a level detected in the absence of the test agent or compound, the test agent or compound may identified as the agent or compound having no significant therapeutic effect.

Suitable reporter genes and host cells are well known in the art. Illustrative reporter genes include, but are not limited to, luciferase, green florescence protein (GFP), *Discosoma* sp. Red Fluorescent Protein (DsRed), Chrolamphenicol Acetyltransferase (CAT), lacZ and beta-glucuronidase (GUS), and host cell is COS7, HEK293, HeLa and so on. The reporter construct required for the screening can be prepared by connecting reporter gene sequence to the transcriptional regulatory region of DLG1 or A20 (TNFAIP3). The transcriptional regulatory region of DLG1 herein includes the region from transcription start site to at least 500 bp upstream, preferably 1000 bp, more preferably 5000 or 10000 bp upstream. Suitable transcriptional regulatory region of DLG1 is position of −1211 to +19 from transcription start site of DLG1 (SEQ ID NO: 56). Alternatively, suitable transcriptional regulatory region of A20 (TNFAIP3) is position of −300 to −35 from transcription start site of A20 (TNFAIP3) (SEQ ID NO: 82). A nucleotide segment containing the transcriptional regulatory region can be isolated from a genome library or can be propagated by PCR. The reporter construct required for the screening can be prepared by connecting reporter gene sequence to the transcriptional regulatory region of any one of these genes. Methods for identifying a transcriptional regulatory region, and also assay protocol are well known (Molecular Cloning third edition chapter 17, 2001, Cold Springs Harbor Laboratory Press).

The vector containing the said reporter construct is infected to host cells and the expression or activity of the reporter gene is detected by method well known in the art (e.g., using luminometer, absorption spectrometer, flow cytometer and so on). "reduces the expression or activity" as defined herein are preferably at least 10% reduction of the expression or activity of the reporter gene in comparison with in absence of the compound, more preferably at least 25%, 50% or 75% reduction and most preferably at 95% reduction.

In the present invention, it is revealed that suppressing the binding between DEPDC1 and ZNF224 reduces cell growth. Thus, by screening for candidate compounds that inhibit the binding of DEPDC1 and ZNF224, candidate compounds that have the potential to treat or prevent cancers can be identified. The therapeutic potential of these candidate compounds may be evaluated by second and/or further screening to identify therapeutic agent for cancers.

VII. Double-Stranded Molecules:

As used herein, the term "isolated double-stranded molecule" refers to a nucleic acid molecule that inhibits expression of a target gene and includes, for example, short interfering RNA (siRNA; e.g., double-stranded ribonucleic acid (dsRNA) or small hairpin RNA (shRNA)) and short interfering DNA/RNA (siD/R-NA; e.g. double-stranded chimera of DNA and RNA (dsD/R-NA) or small hairpin chimera of DNA and RNA (shD/R-NA)).

As use herein, the term "siRNA" refers to a double-stranded RNA molecule which prevents translation of a target mRNA. Standard techniques of introducing siRNA into the cell are used, including those in which DNA is a template from which RNA is transcribed. The siRNA includes an ZNF224 sense nucleic acid sequence (also referred to as "sense strand"), an ZNF224 antisense nucleic acid sequence (also referred to as "antisense strand") or both. The siRNA may be constructed such that a single transcript has both the sense and complementary antisense nucleic acid sequences of the target gene, e.g., a hairpin. The siRNA may either be a dsRNA or shRNA.

As used herein, the term "dsRNA" refers to a construct of two RNA molecules composed of complementary sequences to one another and that have annealed together via the complementary sequences to form a double-stranded RNA molecule. The nucleotide sequence of two strands may include not only the "sense" or "antisense" RNAs selected from a protein coding sequence of target gene sequence, but also RNA molecule having a nucleotide sequence selected from non-coding region of the target gene.

The term "shRNA", as used herein, refers to an siRNA having a stem-loop structure, composed of first and second regions complementary to one another, i.e., sense and antisense strands. The degree of complementarity and orientation of the regions is sufficient such that base pairing occurs between the regions, the first and second regions are joined by a loop region, the loop results from a lack of base pairing between nucleotides (or nucleotide analogs) within the loop region. The loop region of an shRNA is a single-stranded region intervening between the sense and antisense strands and may also be referred to as "intervening single-strand".

As used herein, the term "siD/R-NA" refers to a double-stranded polynucleotide molecule which is composed of both RNA and DNA, and includes hybrids and chimeras of RNA and DNA and prevents translation of a target mRNA. Herein, a hybrid indicates a molecule wherein a polynucleotide composed of DNA and a polynucleotide composed of RNA hybridize to each other to form the double-stranded molecule; whereas a chimera indicates that one or both of the strands composing the double stranded molecule may contain RNA and DNA. Standard techniques of introducing siD/R-NA into the cell are used. The siD/R-NA includes a ZNF224 sense nucleic acid sequence (also referred to as "sense strand"), a ZNF224 antisense nucleic acid sequence (also referred to as "antisense strand") or both. The siD/R-NA may be constructed such that a single transcript has both the sense and complementary antisense nucleic acid sequences from the target gene, e.g., a hairpin. The siD/R-NA may either be a dsD/R-NA or shD/R-NA.

As used herein, the term "dsD/R-NA" refers to a construct of two molecules composed of complementary sequences to one another and that have annealed together via the complementary sequences to form a double-stranded polynucleotide molecule. The nucleotide sequence of two strands may include not only the "sense" or "antisense" polynucleotides sequence selected from a protein coding sequence of target gene sequence, but also polynucleotide having a nucleotide sequence selected from non-coding region of the target gene. One or both of the two molecules constructing the dsD/R-NA are composed of both RNA and DNA (chimeric molecule), or alternatively, one of the molecules is composed of RNA and the other is composed of DNA (hybrid double-strand).

The term "shD/R-NA", as used herein, refers to an siD/R-NA having a stem-loop structure, composed of a first and second regions complementary to one another, i.e., sense and antisense strands. The degree of complementarity and orientation of the regions is sufficient such that base pairing occurs between the regions, the first and second regions are joined by a loop region, the loop results from a lack of base pairing between nucleotides (or nucleotide analogs) within the loop region. The loop region of an shD/R-NA is a single-stranded region intervening between the sense and antisense strands and may also be referred to as "intervening single-strand".

As used herein, an "isolated nucleic acid" is a nucleic acid removed from its original environment (e.g., the natural environment if naturally occurring) and thus, synthetically altered from its natural state. In the context of the present invention, examples of isolated nucleic acid include DNA, RNA, and derivatives thereof.

Figure 2:
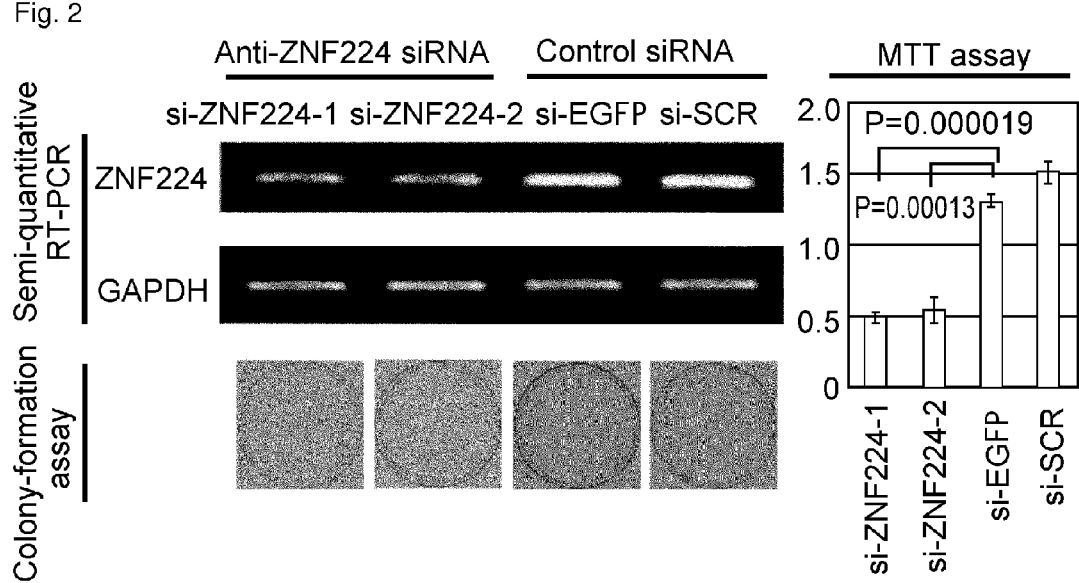
FIG. 2 depicts the growth suppression of bladder cancer cells by siRNAs against ZNF224. The top left portion depicts the results of semiquantitative RT-PCR analysis, demonstrating the knock-down effect in response to si-ZNF224-1, si-ZNF224-2 or control siRNAs (EGFP or SCR) in UM-UC-3 cells. The lower left and right portions depict the results of colony formation and MTT assays of UM-UC-3 cells transfected with specific siRNAs or control plasmids. Bars, SD of triplicate assays.

A double-stranded molecule against ZNF224 that hybridizes to target mRNA decreases or inhibits production of the protein encoded by ZNF224 gene by associating with the normally single-stranded mRNA transcript of the gene, thereby interfering with translation and thus, inhibiting expression of the protein. As demonstrated herein, the expression of ZNF224 in PDAC cell lines was inhibited by dsRNA (FIG. 2). Accordingly, the present invention provides isolated double-stranded molecules that are capable of inhibiting the expression of a ZNF224 gene when introduced into a cell expressing the gene. The target sequence of double-stranded molecule may be designed by an siRNA design algorithm such as that mentioned below.

A ZNF224 target sequence includes, for example, nucleotides

SEQ ID NO: 57 (at the position 494-510 nt of SEQ ID NO: 48); and

SEQ ID NO: 58 (at the position 576-592 nt of SEQ ID NO: 48), and sense strands of the double strand molecules include nucleotides of SEQ ID NO: 9 and 10.

Specifically, the present invention provides the following double-stranded molecules [1] to [20]:

[1] An isolated double-stranded molecule that, when introduced into a cell, inhibits in vivo expression of ZNF224 and cell proliferation, such molecules composed of a sense strand and an antisense strand complementary thereto, hybridized to each other to form the double-stranded molecule;

[2] The double-stranded molecule of [1], wherein said double-stranded molecule acts on mRNA, matching a target sequence selected from among SEQ ID NO: 57 (at the position 494-510 nt of SEQ ID NO: 48) and SEQ ID NO: 58 (at the position 576-592 nt of SEQ ID NO: 48);

[3] The double-stranded molecule of [2], wherein the sense strand contains a sequence corresponding to a target sequence selected from among SEQ ID NOs: 57 and 58;

[4] The double-stranded molecule of [3], having a length of less than about 100 nucleotides;

[5] The double-stranded molecule of [4], having a length of less than about 75 nucleotides;

[6] The double-stranded molecule of [5], having a length of less than about 50 nucleotides;

[7] The double-stranded molecule of [6], having a length of less than about 25 nucleotides;

[8] The double-stranded molecule of [7], having a length of between about 19 and about 25 nucleotides;

[9] The double-stranded molecule of [7], wherein the sense strand consist of a sequence corresponding to a selected from among SEQ ID NOs: 9 and 10;

[10] The double-stranded molecule of [1], composed of a single polynucleotide having both the sense and antisense strands linked by an intervening single-strand;

[11] The double-stranded molecule of [10], having the general formula 5'-[A]-[B]-[A']-3', wherein [A] is the sense strand containing a sequence corresponding to a target sequence selected from among SEQ ID NOs: 57 and 58, [B] is the intervening single-strand composed of 3 to 23 nucleotides, and [A'] is the antisense strand containing a sequence complementary to [A];

[12] The double-stranded molecule of [11], wherein the [A] consists of a sequence corresponding to a selected from among SEQ ID NOs: 9 and 10;

[13] The double-stranded molecule of [1], composed of RNA;

[14] The double-stranded molecule of [1], composed of both DNA and RNA;

[15] The double-stranded molecule of [14], wherein the molecule is a hybrid of a DNA polynucleotide and an RNA polynucleotide;

[16] The double-stranded molecule of [15] wherein the sense and the antisense strands are composed of DNA and RNA, respectively;

[17] The double-stranded molecule of [14], wherein the molecule is a chimera of DNA and RNA;

[18] The double-stranded molecule of [17], wherein a region flanking to the 3'-end of the antisense strand, or both of a region flanking to the 5'-end of sense strand and a region flanking to the 3'-end of antisense strand are RNA;

[19] The double-stranded molecule of [18], wherein the flanking region is composed of 9 to 13 nucleotides; and

[20] The double-stranded molecule of [1], wherein the molecule contains a 3' overhang.

The double-stranded molecule of the present invention will be described in more detail below.

Methods for designing double-stranded molecules having the ability to inhibit target gene expression in cells are known. (See, for example, U.S. Pat. No. 6,506,559, herein incorporated by reference in its entirety). For example, a computer program for designing siRNAs is available from the Ambion website (www.ambion.com/techlib/misc/siRNA_finder.html).

The computer program selects target nucleotide sequences for double-stranded molecules based on the following protocol.

Selection of Target Sites:

1. Beginning with the AUG start codon of the transcript, scan downstream for AA di-nucleotide sequences. Record the occurrence of each AA and the 3' adjacent 19 nucleotides as potential siRNA target sites. Tuschl et al. recommend to avoid designing siRNA to the 5' and 3' untranslated regions (UTRs) and regions near the start codon (within 75 bases) as these may be richer in regulatory protein binding sites, and UTR-binding proteins and/or translation initiation complexes may interfere with binding of the siRNA endonuclease complex.

2. Compare the potential target sites to the appropriate genome database (human, mouse, rat, etc.) and eliminate from consideration any target sequences with significant homology to other coding sequences. Basically, BLAST, which can be found on the NCBI server at: www.ncbi.nlm-.nih.gov/BLAST/, is used (Altschul S F et al., Nucleic Acids Res 1997 Sep. 1, 25(17): 3389-402).

3. Select qualifying target sequences for synthesis. Selecting several target sequences along the length of the gene to evaluate is typical.

Using the above protocol, the target sequence of the isolated double-stranded molecules of the present invention were designed as:

SEQ ID NOs: 57 and 58 for ZNF224 gene.

Double-stranded molecules targeting the above-mentioned target sequences were respectively examined for their ability to suppress the growth of cells expressing the target genes. Therefore, the present invention provides double-stranded molecules targeting any of the sequences selected from the group of:

SEQ ID NO: 57 (at the position 494-510 nt of SEQ ID NO: 48); and

SEQ ID NO: 58 (at the position 576-592 nt of SEQ ID NO: 48) for ZNF224 gene.

The double-stranded molecule of the present invention may be directed to a single target ZNF224 gene sequence or may be directed to a plurality of target ZNF224 gene sequences.

A double-stranded molecule of the present invention targeting the above-mentioned targeting sequence of ZNF224 gene include isolated polynucleotides that contain any of the nucleic acid sequences of target sequences and/or complementary sequences to the target sequences. Examples of polynucleotides targeting ZNF224 gene include those containing the sequence of SEQ ID NO: 57 or 58 and/or complementary sequences to these nucleotides; However, the present invention is not limited to these examples, and minor modifications in the aforementioned nucleic acid sequences are acceptable so long as the modified molecule retains the ability to suppress the expression of ZNF224 gene. Herein, the phrase "minor modification" as used in connection with a nucleic acid sequence indicates one, two or several substitution, deletion, addition or insertion of nucleic acids to the sequence.

In the context of the present invention, the term "several" as applies to nucleic acid substitutions, deletions, additions and/or insertions may mean 3-7, preferably 3-5, more preferably 3-4, even more preferably 3 nucleic acid residues.

In a preferred embodiment of the invention, the double strand molecule has the sense strand selected from the group of SEQ ID NO: 9 and 10.

According to the present invention, a double-stranded molecule of the present invention can be tested for its ability using the methods utilized in the Examples. In the Examples herein below, double-stranded molecules composed of sense strands of various portions of mRNA of ZNF224 genes or antisense strands complementary thereto were tested in vitro for their ability to decrease production of a ZNF224 gene product in cancer cell lines according to standard methods. Furthermore, for example, reduction in a ZNF224 gene product in cells contacted with the candidate double-stranded molecule compared to cells cultured in the absence of the candidate molecule can be detected by, e.g. RT-PCR using primers for ZNF224 mRNA mentioned under Example 1 item "Semi-quantitative reverse transcription-PCR". Sequences that decrease the production of a ZNF224 gene product in vitro cell-based assays can then be tested for there inhibitory effects on cell growth. Sequences that inhibit cell growth in vitro cell-based assay can then be tested for their in vivo ability using animals with cancer, e.g. nude mouse xenograft models, to confirm decreased production of a ZNF224 gene product and decreased cancer cell growth.

When the isolated polynucleotide is RNA or derivatives thereof, base "t" should be replaced with "u" in the nucleotide sequences. As used herein, the term "complementary" refers to Watson-Crick or Hoogsteen base pairing between nucleotides units of a polynucleotide, and the term "binding" means the physical or chemical interaction between two polynucleotides. When the polynucleotide includes modified nucleotides and/or non-phosphodiester linkages, these polynucleotides may also bind each other as same manner. Generally, complementary polynucleotide sequences hybridize under appropriate conditions to form stable duplexes containing few or no mismatches. Furthermore, the sense strand and antisense strand of the isolated polynucleotide of the present invention can form double-stranded molecule or hairpin loop structure by the hybridization. In a preferred embodiment, such duplexes contain no more than 1 mismatch for every 10 matches. In an especially preferred embodiment, where the strands of the duplex are fully complementary, such duplexes contain no mismatches.

The polynucleotide is preferably less than 2466 nucleotides in length for ZNF224. For example, the polynucleotide is less than 500, 200, 100, 75, 50, or 25 nucleotides in length for all of the genes. The isolated polynucleotides of the present invention are useful for forming double-stranded molecules against NM_013398 gene or preparing template DNAs encoding the double-stranded molecules. When the polynucleotides are used for forming double-stranded molecules, the polynucleotide may be longer than 19 nucleotides, preferably longer than 21 nucleotides, and more preferably has a length of between about 19 and 25 nucleotides.

Accordingly, the present invention provides the double-stranded molecules comprising a sense strand and an antisense strand, wherein the sense strand comprises a nucleotide sequence corresponding to a target sequence. In preferable embodiments, the sense strand hybridizes with antisense strand at the target sequence to form the double-stranded molecule having between 19 and 25 nucleotide pair in length.

The double-stranded molecules of the invention may contain one or more modified nucleotides and/or non-phosphodiester linkages. Chemical modifications well known in the art are capable of increasing stability, availability, and/or cell uptake of the double-stranded molecule. The skilled person will be aware of other types of chemical modification which may be incorporated into the present molecules (WO03/070744; WO2005/045037). In one embodiment, modifications can be used to provide improved resistance to degradation or improved uptake. Examples of such modifications include, but are not limited to, phosphorothioate linkages, 2'-O-methyl ribonucleotides (especially on the sense strand of a double-stranded molecule), 2'-deoxy-fluoro ribonucleotides, 2'-deoxy ribonucleotides, "universal base" nucleotides, 5'-C-methyl nucleotides, and inverted deoxybasic residue incorporation (US20060122137).

In another embodiment, modifications can be used to enhance the stability or to increase targeting efficiency of the double-stranded molecule. Examples of such modifications include, but are not limited to, chemical cross linking between the two complementary strands of a double-stranded molecule, chemical modification of a 3' or 5' terminus of a strand of a double-stranded molecule, sugar modifications, nucleobase modifications and/or backbone modifications, 2-fluoro modified ribonucleotides and 2'-deoxy ribonucleotides (WO2004/029212). In another embodiment, modifications can be used to increased or decreased affinity for the complementary nucleotides in the target mRNA and/or in the complementary double-stranded molecule strand (WO2005/044976). For example, an unmodified pyrimidine nucleotide can be substituted for a 2-thio, 5-alkynyl, 5-methyl, or 5-propynyl pyrimidine. Additionally, an unmodified purine can be substituted with a 7-deza, 7-alkyl, or 7-alkenyl purine. In another embodiment, when the double-stranded molecule is a double-stranded molecule with a 3' overhang, the 3'-terminal nucleotide overhanging nucleotides may be replaced by deoxyribonucleotides (Elbashir S M et al., Genes Dev 2001 Jan. 15, 15(2): 188-200). For further details, published documents such as US20060234970 are available. The present invention is not limited to these examples and any known chemical modifications may be employed for the double-stranded molecules of the present invention so long as the resulting molecule retains the ability to inhibit the expression of the target gene.

Furthermore, the double-stranded molecules of the invention may include both DNA and RNA, e.g., dsD/R-NA or shD/R-NA. Specifically, a hybrid polynucleotide of a DNA strand and an RNA strand or a DNA-RNA chimera polynucleotide shows increased stability. Mixing of DNA and RNA, i.e., a hybrid type double-stranded molecule composed of a DNA strand (polynucleotide) and an RNA strand (polynucleotide), a chimera type double-stranded molecule containing both DNA and RNA on any or both of the single strands (polynucleotides), or the like may be formed for enhancing stability of the double-stranded molecule.

The hybrid of a DNA strand and an RNA strand may be either where the sense strand is DNA and the antisense strand is RNA, or vice versa, so long as it can inhibit expression of the target gene when introduced into a cell expressing the gene. Preferably, the sense strand polynucleotide is DNA and the antisense strand polynucleotide is RNA. Also, the chimera type double-stranded molecule may be either where both of the sense and antisense strands are composed of DNA and RNA, or where any one of the sense and antisense strands is composed of DNA and RNA so long as it has an activity to inhibit expression of the target gene when introduced into a cell expressing the gene. In order to enhance stability of the double-stranded molecule, the molecule preferably contains as much DNA as possible, whereas to induce inhibition of the target gene expression, the molecule is required to be RNA within a range to induce sufficient inhibition of the expression.

As a preferred example of the chimera type double-stranded molecule, an upstream partial region (i.e., a region flanking to the target sequence or complementary sequence thereof within the sense or antisense strands) of the double-stranded molecule is RNA. Preferably, the upstream partial region indicates the 5' side (5'-end) of the sense strand and the 3' side (3'-end) of the antisense strand. Alternatively, regions flanking to 5'-end of sense strand and/or 3'-end of antisense strand are referred to upstream partial region. That is, in preferable embodiments, a region flanking to the 3'-end of the antisense strand, or both of a region flanking to the 5'-end of sense strand and a region flanking to the 3'-end of antisense strand are composed of RNA. For instance, the chimera or hybrid type double-stranded molecule of the present invention include following combinations.
sense strand:

```
5'-[---DNA---]-3'
3'-(RNA)-[DNA]-5':
``` antisense strand,
sense strand:

```
5'-(RNA)-[DNA]-3'
3'-(RNA)-[DNA]-5':
``` antisense strand, and
sense strand:

```
5'-(RNA)-[DNA]-3'
3'-(---RNA---)-5':
``` antisense strand.

The upstream partial region preferably is a domain composed of 9 to 13 nucleotides counted from the terminus of the target sequence or complementary sequence thereto within the sense or antisense strands of the double-stranded molecules. Moreover, preferred examples of such chimera type double-stranded molecules include those having a strand length of 19 to 21 nucleotides in which at least the upstream half region (5' side region for the sense strand and 3' side region for the antisense strand) of the polynucleotide is RNA and the other half is DNA. In such a chimera type double-stranded molecule, the effect to inhibit expression of the target gene is much higher when the entire antisense strand is RNA (US20050004064).

In the context of the present invention, the double-stranded molecule may form a hairpin, such as a short hairpin RNA (shRNA) and short hairpin consisting of DNA and RNA (shD/R-NA). The shRNA or shD/R-NA is a sequence of RNA or mixture of RNA and DNA making a tight hairpin turn that can be used to silence gene expression via RNA interference. The shRNA or shD/R-NA includes the sense target sequence and the antisense target sequence on a single strand wherein the sequences are separated by a loop sequence. Generally, the hairpin structure is cleaved by the cellular machinery into dsRNA or dsD/R-NA, which is then bound to the RNA-induced silencing complex (RISC). This complex binds to and cleaves mRNAs which match the target sequence of the dsRNA or dsD/R-NA.

A loop sequence composed of an arbitrary nucleotide sequence can be located between the sense and antisense sequence in order to form the hairpin loop structure. Thus, the present invention also provides a double-stranded molecule having the general formula 5'-[A]-[B]-[A']-3', wherein [A] is the sense strand containing a sequence corresponding to a target sequence, [B] is an intervening single-strand and [A'] is the antisense strand containing a complementary sequence to [A]. The target sequence may be selected from among, for example, nucleotides of SEQ ID NO: 57 or 58 for ZNF224.

The present invention is not limited to these examples, and the target sequence in [A] may be modified sequences from these examples so long as the double-stranded molecule retains the ability to suppress the expression of the targeted ZNF224 gene. In the present invention, the region [A] is preferably selected from the sequence of SEQ ID NO: 9 or 10. The region [A] hybridizes to [A'] to form a loop composed of the region [B]. The intervening single-stranded portion [B], i.e., loop sequence may be preferably 3 to 23 nucleotides in length. The loop sequence, for example, can be selected from among the following sequences (www.ambion.com/techlib/tb/tb_506.html). Furthermore, loop sequence consisting of 23 nucleotides also provides active siRNA (Jacque J M et al., Nature 2002 Jul. 25, 418(6896): 435-8, Epub 2002 Jun. 26):

CCC, CCACC, or CCACACC: Jacque J M et al., Nature 2002 Jul. 25, 418(6896): 435-8, Epub 2002 Jun. 26;

UUCG: Lee N S et al., Nat Biotechnol 2002 May, 20(5): 500-5; Fruscoloni P et al., Proc Natl Acad Sci USA 2003 Feb. 18, 100(4): 1639-44, Epub 2003 Feb. 10; and UUCAAGAGA: Dykxhoorn D M et al., Nat Rev Mol Cell Biol 2003 June, 4(6): 457-67.

Examples of preferred double-stranded molecules of the present invention having hairpin loop structure are shown below. In the following structure, the loop sequence can be selected from among AUG, CCC, UUCG, CCACC, CTCGAG, AAGCUU, CCACACC, and UUCAAGAGA; however, the present invention is not limited thereto:

```
                    (for target sequence SEQ ID NO: 57)
GAUUUGGAUGAUGAAGA-[B]-UCUUCAUCAUCCAAAUC;

(for target sequence SEQ ID NO: 58)
GCAGGAACACAUCAAGA-[B]-UCUUGAUGUGUUCCUGC;

(for SEQ ID NO: 9)
CCGAUUUGGAUGAUGAAGA-[B]-UCUUCAUCAUCCAAAUCGG;

(for SEQ ID NO: 10)
CCGCAGGAACACAUCAAGA-[B]-UCUUGAUGUGUUCCUGCGG.
```

Furthermore, in order to enhance the inhibition activity of the double-stranded molecules, nucleotide "u" can be added to 3' end of the antisense strand of the target sequence, as 3' overhangs. The number of "u"s to be added is at least 2, generally 2 to 10, preferably 2 to 5. The added "u"s form single strand at the 3' end of the antisense strand of the double-stranded molecule.

The method for preparing the double-stranded molecule is not particularly limited though it is preferable to use a chemical synthetic method known in the art. According to the chemical synthesis method, sense and antisense single-stranded polynucleotides are separately synthesized and then annealed together via an appropriate method to obtain a double-stranded molecule. Specific example for the annealing includes wherein the synthesized single-stranded polynucleotides are mixed in a molar ratio of preferably at least about 3:7, more preferably about 4:6, and most preferably substantially equimolar amount (i.e., a molar ratio of about 5:5). Next, the mixture is heated to a temperature at which double-stranded molecules dissociate and then is gradually cooled down. The annealed double-stranded polynucleotide can be purified by usually employed methods known in the art. Example of purification methods include methods utilizing agarose gel electrophoresis or wherein remaining single-stranded polynucleotides are optionally removed by, e.g., degradation with appropriate enzyme.

The regulatory sequences flanking ZNF224 sequences may be identical or different, such that their expression can be modulated independently, or in a temporal or spatial manner. The double-stranded molecules can be transcribed intracellularly by cloning ZNF224 gene templates into a vector containing, e.g., a RNA pol III transcription unit from the small nuclear RNA (snRNA) U6 or the human H1 RNA promoter.

VIII. Vectors Containing A Double-Stranded Molecule Of The Present Invention:

Also included in the present invention are vectors containing one or more of the double-stranded molecules described herein, and a cell containing such a vector.

Specifically, the present invention provides the following vector of [1] to [12].

[1] A vector, encoding a double-stranded molecule that, when introduced into a cell, inhibits in vivo expression of ZNF224 and cell proliferation, such molecules composed of a sense strand and an antisense strand complementary thereto, hybridized to each other to form the double-stranded molecule.

[2] The vector of [1], encoding the double-stranded molecule acts on mRNA, matching a target sequence selected from among SEQ ID NO: 57 (at the position 494-510 nt of SEQ ID NO: 48); and SEQ ID NO: 58 (at the position 576-592 nt of SEQ ID NO: 48);

[3] The vector of [1], wherein the sense strand contains a sequence corresponding to a target sequence selected from among SEQ ID NOs: 57 and 58;

[4] The vector of [3], encoding the double-stranded molecule, having a length of less than about 100 nucleotides;

[5] The vector of [4], encoding the double-stranded molecule, having a length of less than about 75 nucleotides;

[6] The vector of [5], encoding the double-stranded molecule, having a length of less than about 50 nucleotides;

[7] The vector of [6], encoding the double-stranded molecule, having a length of less than about 25 nucleotides;

[8] The vector of [7], encoding the double-stranded molecule, having a length of between about 19 and about 25 nucleotides;

[9] The vector of [1], wherein the sense strand consists of a sequence corresponding to a sequence selected from among SEQ ID NOs: 9 and 10;

[10] The vector of [1], wherein the double-stranded molecule is composed of a single polynucleotide having both the sense and antisense strands linked by an intervening single-strand;

[11] The vector of [10], encoding the double-stranded molecule having the general formula 5'-[A]-[B]-[A']-3', wherein [A] is the sense strand containing a sequence corresponding to a target sequence selected from among SEQ ID NOs: 57 and 58, [B] is the intervening single-strand composed of 3 to 23 nucleotides, and [A'] is the antisense strand containing a sequence complementary to [A];

[12] The vector of [11], wherein the [A] consists of a sequence corresponding to a sequence selected from among SEQ ID NOs: 9 and 10.

A vector of the present invention preferably encodes a double-stranded molecule of the present invention in an expressible form. Herein, the phrase "in an expressible form" indicates that the vector, when introduced into a cell, will express the molecule. In a preferred embodiment, the vector includes regulatory elements necessary for expression of the double-stranded molecule. Such vectors of the present invention may be used for producing the present double-stranded molecules, or directly as an active ingredient for treating cancer.

Vectors of the present invention can be produced, for example, by cloning ZNF224 sequence into an expression vector so that regulatory sequences are operatively-linked to ZNF224 sequence in a manner to allow expression (by transcription of the DNA molecule) of both strands (Lee N S et al., Nat Biotechnol 2002 May, 20(5): 500-5). For example, RNA molecule that is the antisense to mRNA is transcribed by a first promoter (e.g., a promoter sequence flanking to the 3' end of the cloned DNA) and RNA molecule that is the sense strand to the mRNA is transcribed by a second promoter (e.g., a promoter sequence flanking to the 5' end of the cloned DNA). The sense and antisense strands hybridize in vivo to generate a double-stranded molecule constructs for silencing of the gene. Alternatively, two vectors constructs respectively encoding the sense and antisense strands of the double-stranded molecule are utilized to respectively express the sense and anti-sense strands and then forming a double-stranded molecule construct. Furthermore, the cloned sequence may encode a construct having a secondary structure (e.g., hairpin); namely, a single transcript of a vector contains both the sense and complementary antisense sequences of the target gene.

The vectors of the present invention may also be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The vectors of the present invention include, for example, viral or bacterial vectors. Examples of expression vectors include attenuated viral hosts, such as vaccinia or fowlpox (see, e.g., U.S. Pat. No. 4,722,848). This approach involves the use of vaccinia virus, e.g., as a vector to express nucleotide sequences that encode the double-stranded molecule. Upon introduction into a cell expressing the target gene, the recombinant vaccinia virus expresses the molecule and thereby suppresses the proliferation of the cell. Another example of useable vector includes Bacille Calmette Guerin (BCG). BCG vectors are described in Stover et al., Nature 1991, 351: 456-60. A wide variety of other vectors are useful for therapeutic administration and production of the double-stranded molecules; examples include adeno and adeno-associated virus vectors, retroviral vectors, *Salmonella typhi* vectors, detoxified anthrax toxin vectors, and the like. See, e.g., Shata et al., Mol Med Today 2000, 6: 66-71; Shedlock et al., J Leukoc Biol 2000, 68: 793-806; and Hipp et al., In Vivo 2000, 14: 571-85.

IX. Methods of inhibiting or reducing growth of a cancer cell and treating cancer Using a double-stranded molecule of the present invention:

The ability of certain siRNA to inhibit cancer has been previously described in WO2006/085684, incorporated by reference herein. In present invention, two different dsRNA for ZNF224 were tested for their ability to inhibit cell growth.

The two dsRNA for ZNF224 that effectively knocked down the expression of the gene in cancer cell lines coincided with suppression of cell proliferation (FIG. 2).

Accordingly, the present invention provides methods for inhibiting cell growth, i.e., bladder cancer cell growth, by inducing dysfunction of the ZNF224 gene via inhibiting the expression of ZNF224. ZNF224 gene expression can be inhibited by any of the aforementioned double-stranded molecules of the present invention which specifically target of ZNF224 gene or the vectors of the present invention that can express any of the double-stranded molecules.

Such ability of the present double-stranded molecules and vectors to inhibit cell growth of cancerous cell indicates that they can be used for methods for treating cancer. Thus, the present invention provides methods to treat patients with cancer by administering a double-stranded molecule against a ZNF224 gene or a vector expressing the molecule without adverse effect because that genes were hardly detected in normal organs (FIG. 1).

Specifically, the present invention provides the following methods [1] to [38]:

[1] A method for inhibiting growth of a cancer cell and treating a cancer, wherein the cancer cell or the cancer expresses a ZNF224 gene, such method including the step of administering at least one isolated double-stranded molecule inhibiting the expression of ZNF224 in a cell over-expressing the gene and the cell proliferation, wherein the double-stranded molecule is composed of a sense strand and an antisense strand complementary thereto, hybridized to each other to form the double-stranded molecule.

[2] The method of [1], wherein the double-stranded molecule acts at mRNA which matches a target sequence selected from among SEQ ID NO: 57 (at the position of 494-510 nt of SEQ ID NO: 48) and SEQ ID NO: 58 (at the position of 576-592 nt of SEQ ID NO: 48).;

[3] The method of [2], wherein the sense strand contains the sequence corresponding to a target sequence selected from among SEQ ID NOs: 57 and 58.

[4] The method of [1], wherein the cancer to be treated is bladder cancer;

[5] The method of [1], wherein plural kinds of the double-stranded molecules are administered;

[6] The method of [3], wherein the double-stranded molecule has a length of less than about 100 nucleotides;

[7] The method of [6], wherein the double-stranded molecule has a length of less than about 75 nucleotides;

[8] The method of [7], wherein the double-stranded molecule has a length of less than about 50 nucleotides;

[9] The method of [8], wherein the double-stranded molecule has a length of less than about 25 nucleotides;

[10] The method of [9], wherein the double-stranded molecule has a length of between about 19 and about 25 nucleotides in length;

[11] The method of [10], wherein the sense strand consist of the sequence corresponding to a selected from among SEQ ID NOs: 9 and 10.

[12] The method of [10], wherein the double-stranded molecule is composed of a single polynucleotide containing both the sense strand and the antisense strand linked by an intervening single-strand;

[13] The method of [12], wherein the double-stranded molecule has the general formula 5'-[A]-[B]-[A']-3', wherein [A] is the sense strand containing a sequence corresponding to a target sequence selected from among SEQ ID NOs: 9 and 10, [B] is the intervening single strand composed of 3 to 23 nucleotides, and [A'] is the antisense strand containing a sequence complementary to [A];

[14] The method of [13], wherein the [A] consist of the sequence corresponding to a selected from among SEQ ID NOs: 9 and 10.

[15] The method of [1], wherein the double-stranded molecule is an RNA;

[16] The method of [1], wherein the double-stranded molecule contains both DNA and RNA;

[17] The method of [16], wherein the double-stranded molecule is a hybrid of a DNA polynucleotide and an RNA polynucleotide;

[18] The method of [17] wherein the sense and antisense strand polynucleotides are composed of DNA and RNA, respectively;

[19] The method of [16], wherein the double-stranded molecule is a chimera of DNA and RNA;

[20] The method of [19], wherein a region flanking to the 3'-end of the antisense strand, or both of a region flanking to the 5'-end of sense strand and a region flanking to the 3'-end of antisense strand are composed of RNA;

[21] The method of [20], wherein the flanking region is composed of 9 to 13 nucleotides;

[22] The method of [1], wherein the double-stranded molecule contains 3' overhangs;

[23] The method of [1], wherein the double-stranded molecule is contained in a composition which includes, in addition to the molecule, a transfection-enhancing agent and pharmaceutically acceptable carrier;

[24] The method of [1], wherein the double-stranded molecule is encoded by a vector;

[25] The method of [24], wherein the double-stranded molecule encoded by the vector acts at mRNA which matches a target sequence selected from among SEQ ID NO: 57 (at the position of 455-485 nt of SEQ ID NO: 48) and SEQ ID NO: 58 (at the position of 576-592 nt of SEQ ID NO: 48);

[26] The method of [25], wherein the sense strand of the double-stranded molecule encoded by the vector contains the sequence corresponding to a target sequence selected from among SEQ ID NOs: 57 and 58.

[27] The method of [24], wherein the cancer to be treated is bladder cancer;

[28] The method of [24], wherein plural kinds of the double-stranded molecules are administered;

[29] The method of [26], wherein the double-stranded molecule encoded by the vector has a length of less than about 100 nucleotides;

[30] The method of [29], wherein the double-stranded molecule encoded by the vector has a length of less than about 75 nucleotides;

[31] The method of [30], wherein the double-stranded molecule encoded by the vector has a length of less than about 50 nucleotides;

[32] The method of [31], wherein the double-stranded molecule encoded by the vector has a length of less than about 25 nucleotides;

[33] The method of [32], wherein the double-stranded molecule encoded by the vector has a length of between about 19 and about 25 nucleotides in length;

[34] The method of [33], wherein the sense strand consist of the sequence corresponding to a selected from among SEQ ID NOs: 9 and 10.

[35] The method of [24], wherein the double-stranded molecule encoded by the vector is composed of a single polynucleotide containing both the sense strand and the antisense strand linked by an interventing single-strand;

[36] The method of [35], wherein the double-stranded molecule encoded by the vector has the general formula 5'-[A]-[B]-[A']-3', wherein [A] is the sense strand containing a sequence corresponding to a target sequence selected from among SEQ ID NOs: 9 and 10, [B] is a intervening single-strand is composed of 3 to 23 nucleotides, and [A'] is the antisense strand containing a sequence complementary to [A];

[37] The method of [36], wherein the [A] consist of the sequence corresponding to a selected from among SEQ ID NOs: 9 and 10; and

[38] The method of [24], wherein the double-stranded molecule encoded by the vector is contained in a composition which includes, in addition to the molecule, a transfection-enhancing agent and pharmaceutically acceptable carrier.

The method of the present invention will be described in more detail below.

The growth of cells expressing a ZNF224 gene may be inhibited by contacting the cells with a double-stranded molecule against a ZNF224 gene, a vector expressing the molecule or a composition containing the same. The cell may be further contacted with a transfection agent. Suitable transfection agents are known in the art. The phrase "inhibition of cell growth" indicates that the cell proliferates at a lower rate or has decreased viability as compared to a cell not exposed to the molecule. Cell growth may be measured by methods known in the art, e.g., using the MTT cell proliferation assay.

The growth of any kind of cell may be suppressed according to the present method so long as the cell expresses or over-expresses the target gene of the double-stranded molecule of the present invention. Exemplary cells include cancer cells, particularly bladder cell lines.

Thus, patients suffering from or at risk of developing a disease related to ZNF224 may be treated with the administration of at least one of the present double-stranded molecules, at least one vector expressing at least one of the molecules or at least one composition containing at least one of the molecules. For example, patients suffering from bladder cancer may be treated according to the present methods. The type of cancer may be identified by standard methods according to the particular type of tumor to be diagnosed. Preferably, patients treated by the methods of the present invention are selected by detecting the expression of ZNF224 in a biopsy from the patient by RT-PCR or immunoassay. More preferably, before the treatment of the present invention, the biopsy specimen from the subject is confirmed for a ZNF224 gene over-expression by methods known in the art, for example, immunohistochemical analysis or RT-PCR.

According to the present method, to inhibit cell growth and thereby treat cancer through the administration of plural kinds of the double-stranded molecules (or vectors expressing or compositions containing the same), each of the molecules may have different structures but act on an mRNA that matches the same target sequence of ZNF224. Alternatively, plural kinds of double-stranded molecules may act on an mRNA that matches a different target sequence of same gene. For example, the method may utilize double-stranded molecules directed to one, two or more target sequences selected from ZNF224.

For inhibiting cell growth, a double-stranded molecule of present invention may be directly introduced into the cells in a form to achieve binding of the molecule with corresponding mRNA transcripts. Alternatively, as described above, a DNA encoding the double-stranded molecule may be introduced into cells as a vector. For introducing the double-stranded molecules and vectors into the cells, transfection-enhancing agent, such as FuGENE (Roche diagnostics), Lipofectamine 2000 (Invitrogen), Oligofectamine (Invitrogen), and Nucleofector (Wako pure Chemical), may be employed.

A treatment is deemed "efficacious" if it leads to clinical benefit such as, reduction in expression of ZNF224 gene, or a decrease in size, prevalence, or metastatic potential of the cancer in the subject. When the treatment is applied prophylactically, "efficacious" means that it retards or prevents cancers from forming or prevents or alleviates a clinical symptom of cancer. Efficaciousness is determined in association with any known method for diagnosing or treating the particular tumor type.

To the extent that the methods and compositions of the present invention find utility in the context of "prevention" and "prophylaxis", such terms are interchangeably used herein to refer to any activity that reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis can include a wide range of prophylactic therapies aimed at alleviating the severity of the particular disorder, e.g. reducing the proliferation and metastasis of tumors.

The treatment and/or prophylaxis of cancer and/or the prevention of postoperative recurrence thereof include any of the following steps, such as the surgical removal of cancer cells, the inhibition of the growth of cancerous cells, the involution or regression of a tumor, the induction of remission and suppression of occurrence of cancer, the tumor regression, and the reduction or inhibition of metastasis. Effectively treating and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

It is understood that a double-stranded molecule of the invention degrades ZNF224 mRNA in substoichiometric amounts. Without wishing to be bound by any theory, it is believed that the double-stranded molecule of the invention causes degradation of the target mRNA in a catalytic manner. Thus, as compared to standard cancer therapies, the present invention requires the delivery of significantly less double-stranded molecule at or near the site of cancer in order to exert therapeutic effect.

One skilled in the art can readily determine an effective amount of the double-stranded molecule of the invention to be administered to a given subject, by taking into account factors such as body weight, age, sex, type of disease, symptoms and other conditions of the subject; the route of administration; and whether the administration is regional or systemic. Generally, an effective amount of the double-stranded molecule of the invention is an intercellular concentration at or near the cancer site of from about 1 nanomolar (nM) to about 100 nM, preferably from about 2 nM to about 50 nM, more preferably from about 2.5 nM to about 10 nM. It is contemplated that greater or smaller amounts of the double-stranded molecule can be administered. The precise dosage required for a particular circumstance may be readily and routinely determined by one of skill in the art.

The present methods can be used to inhibit the growth or metastasis of cancer expressing at least one ZNF224; for example, bladder cancer. In particular, a double-stranded molecule containing a target sequence of ZNF224 (i.e., SEQ ID NOs: 57 or 58) is particularly preferred for the treatment of cancer.

For treating cancer, the double-stranded molecule of the invention can also be administered to a subject in combination with a pharmaceutical agent different from the double-stranded molecule. Alternatively, the double-stranded molecule of the invention can be administered to a subject in combination with another therapeutic method designed to treat cancer. For example, the double-stranded molecule of the invention can be administered in combination with therapeutic methods currently employed for treating cancer or preventing cancer metastasis (e.g., radiation therapy, surgery and treatment using chemotherapeutic agents, such as cisplatin, carboplatin, cyclophosphamide, 5-fluorouracil, adriamycin, daunorubicin or tamoxifen).

In the present methods, the double-stranded molecule can be administered to the subject either as a naked double-stranded molecule, in conjunction with a delivery reagent, or as a recombinant plasmid or viral vector which expresses the double-stranded molecule.

Suitable delivery reagents for administration in conjunction with the present a double-stranded molecule include the Mirus Transit TKO lipophilic reagent; lipofectin; lipofectamine; cellfectin; or polycations (e.g., polylysine), or liposomes. A preferred delivery reagent is a liposome.

Liposomes can aid in the delivery of the double-stranded molecule to a particular tissue, such as bladder tissue, and can also increase the blood half-life of the double-stranded molecule. Liposomes suitable for use in the context of the present invention may be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al., Ann Rev Biophys Bioeng 1980, 9: 467; and U.S. Pat. Nos. 4,235,871; 4,501,728; 4,837,028; and 5,019,369, the entire disclosures of which are herein incorporated by reference.

Preferably, the liposomes encapsulating the present double-stranded molecule includes a ligand molecule that can deliver the liposome to the cancer site. Ligands which bind to receptors prevalent in tumor or vascular endothelial cells, such as monoclonal antibodies that bind to tumor antigens or endothelial cell surface antigens, are preferred.

Particularly preferably, the liposomes encapsulating the present double-stranded molecule are modified so as to avoid clearance by the mononuclear macrophage and reticuloendothelial systems, for example, by having opsonization-inhibition moieties bound to the surface of the structure. In one embodiment, a liposome of the invention can include both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016, the entire disclosure of which is herein incorporated by reference. Liposomes modified with opsonization-inhibition moieties thus remain in the circulation much longer than unmodified liposomes. For this reason, such liposomes are sometimes called "stealth" liposomes.

Stealth liposomes are known to accumulate in tissues fed by porous or "leaky" microvasculature. Thus, target tissue characterized by such microvasculature defects, for example, solid tumors, will efficiently accumulate these liposomes; see Gabizon et al., Proc Natl Acad Sci USA 1988, 18: 6949-53. In addition, the reduced uptake by the RES lowers the toxicity of stealth liposomes by preventing significant accumulation in liver and spleen. Thus, liposomes of the invention that are modified with opsonization-inhibition moieties can deliver the present double-stranded molecule to tumor cells.

Opsonization inhibiting moieties suitable for modifying liposomes are preferably water-soluble polymers with a molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as poly-acrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM.sub.1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups.

Preferably, the opsonization-inhibiting moiety is a PEG, PPG, or derivatives thereof. Liposomes modified with PEG or PEG-derivatives are sometimes called "PEGylated liposomes".

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using Na(CN)BH.sub.3 and a solvent mixture such as tetrahydrofuran and water in a 30:12 ratio at 60 degrees C.

Vectors expressing a double-stranded molecule of the present invention are discussed above. Such vectors expressing at least one double-stranded molecule of the invention can also be administered directly or in conjunction with a suitable delivery reagent, including the Mirus Transit LT1 lipophilic reagent; lipofectin; lipofectamine; cellfectin; polycations (e.g., polylysine) or liposomes. Methods for delivering recombinant viral vectors, which express a double-stranded molecule of the invention, to an area of cancer in a patient are within the skill of the art.

The double-stranded molecule of the invention can be administered to the subject by any means suitable for delivering the double-stranded molecule into cancer sites. For example, the double-stranded molecule can be administered by gene gun, electroporation, or by other suitable parenteral or enteral administration routes.

Suitable enteral administration routes include oral, rectal, intranasal or intravesical-delivery.

Suitable parenteral administration routes include intravesical or intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection); subcutaneous injection or deposition including subcutaneous infusion (such as by osmotic pumps); direct application to the area at or near the site of cancer, for example by a catheter or other placement device (e.g., a suppository or an implant including a porous, non-porous, or gelatinous material); and inhalation. It is preferred that injections or infusions of the double-stranded molecule or vector be given at or near the site of the cancer.

The double-stranded molecule of the invention can be administered in a single dose or in multiple doses. Where the administration of the double-stranded molecule of the invention is by infusion, the infusion can be a single sustained dose or can be delivered by multiple infusions. Injection of the agent directly into the tissue is at or near the site of cancer preferred. Multiple injections of the agent into the tissue at or near the site of cancer are particularly preferred.

One skilled in the art can also readily determine an appropriate dosage regimen for administering the double-stranded molecule of the invention to a given subject. For example, the double-stranded molecule can be administered to the subject once, for example, as a single injection or deposition at or near the cancer site. Alternatively, the double-stranded molecule can be administered once or twice daily to a subject for a period of from about three to about twenty-eight days, more preferably from about seven to about ten days. In a preferred dosage regimen, the double-stranded molecule is injected at or near the site of cancer once a day for seven days. Where a dosage regimen includes multiple administrations, it is understood that the effective amount of a double-stranded molecule administered to the subject can include the total amount of a double-stranded molecule administered over the entire dosage regimen.

X. Compositions containing a double-stranded molecule of the present invention:

In addition to the above, the present invention also provides pharmaceutical compositions that include at least one of the present double-stranded molecules or the vectors coding for the molecules. Specifically, the present invention provides the following compositions [1] to [38]:

[1] A composition for inhibiting a growth of a cancer cell and treating a cancer, wherein the cancer and the cancer cell express a ZNF224 gene, including at least one isolated double-stranded molecule that inhibits the expression of the ZNF224 gene and the cell proliferation, further wherein the molecule is composed of a sense strand and an antisense strand complementary thereto, hybridized to each other to form the double-stranded molecule.

[2] The composition of [1], wherein the double-stranded molecule acts at mRNA which matches a target sequence selected from among SEQ ID NO: 57 (at the position of 494-510 nt of SEQ ID NO: 48) and SEQ ID NO: 58 (at the position of 576-592 nt of SEQ ID NO: 48);

[3] The composition of [2], wherein the double-stranded molecule, wherein the sense strand contains a sequence corresponding to a target sequence selected from among SEQ ID NOs: 57 and 58.

[4] The composition of [1], wherein the cancer to be treated is bladder cancer;

[5] The composition of [1], wherein the composition contains plural kinds of the double-stranded molecules;

[6] The composition of [3], wherein the double-stranded molecule has a length of less than about 100 nucleotides;

[7] The composition of [6], wherein the double-stranded molecule has a length of less than about 75 nucleotides;

[8] The composition of [7], wherein the double-stranded molecule has a length of less than about 50 nucleotides;

[9] The composition of [8], wherein the double-stranded molecule has a length of less than about 25 nucleotides;

[10] The composition of [9], wherein the double-stranded molecule has a length of between about 19 and about 25 nucleotides;

[11] The composition of [1], wherein the double-stranded molecule is composed of a single polynucleotide containing the sense strand and the antisense strand linked by an intervening single-strand;

[12] The method of [11], wherein the sense strand consist of the sequence corresponding to a selected from among SEQ ID NOs: 9 and 10.

[13] The composition of [12], wherein the double-stranded molecule has the general formula 5'-[A]-[B]-[A']-3', wherein [A] is the sense strand sequence contains a sequence corresponding to a target sequence selected from among SEQ ID NOs: 9 and 10, [B] is the intervening single-strand consisting of 3 to 23 nucleotides, and [A'] is the antisense strand contains a sequence complementary to [A];

[14] The method of [13], wherein the [A] consist of the sequence corresponding to a selected from among SEQ ID NOs: 9 and 10.

[15] The composition of [1], wherein the double-stranded molecule is an RNA;

[16] The composition of [1], wherein the double-stranded molecule is DNA and/or RNA;

[17] The composition of [16], wherein the double-stranded molecule is a hybrid of a DNA polynucleotide and an RNA polynucleotide;

[18] The composition of [17], wherein the sense and antisense strand polynucleotides are composed of DNA and RNA, respectively;

[19] The composition of [16], wherein the double-stranded molecule is a chimera of DNA and RNA;

[20] The composition of [19], wherein a region flanking to the 3'-end of the antisense strand, or both of a region flanking to the 5'-end of sense strand and a region flanking to the 3'-end of antisense strand are composed of RNA;

[21] The composition of [20], wherein the flanking region is composed of 9 to 13 nucleotides;

[22] The composition of [1], wherein the double-stranded molecule contains 3' overhangs;

[23] The composition of [1], wherein the composition includes a transfection-enhancing agent and pharmaceutically acceptable carrier.

[24] The composition of [1], wherein the double-stranded molecule is encoded by a vector and contained in the composition;

[25] The composition of [24], wherein the double-stranded molecule encoded by the vector acts at mRNA which matches a target sequence selected from among SEQ ID NO: 57 (at the position of 494-510 nt of SEQ ID NO: 48) and SEQ ID NO: 58 (at the position of 576-592 nt of SEQ ID NO: 48).

[26] The composition of [25], wherein the sense strand of the double-stranded molecule encoded by the vector contains the sequence corresponding to a target sequence selected from among SEQ ID NOs: 57 and 58.

[27] The composition of [24], wherein the cancer to be treated is bladder cancer;

[28] The composition of [24], wherein plural kinds of the double-stranded molecules are administered;

[29] The composition of [26], wherein the double-stranded molecule encoded by the vector has a length of less than about 100 nucleotides;

[30] The composition of [29], wherein the double-stranded molecule encoded by the vector has a length of less than about 75 nucleotides;

[31] The composition of [30], wherein the double-stranded molecule encoded by the vector has a length of less than about 50 nucleotides;

[32] The composition of [31], wherein the double-stranded molecule encoded by the vector has a length of less than about 25 nucleotides;

[33] The composition of [32], wherein the double-stranded molecule encoded by the vector has a length of between about 19 and about 25 nucleotides in length;

[34] The method of [33], wherein the sense strand consist of the sequence corresponding to a selected from among SEQ ID NOs: 9 and 10.

[35] The composition of [24], wherein the double-stranded molecule encoded by the vector is composed of a single polynucleotide containing both the sense strand and the antisense strand linked by an intervening single-strand;

[36] The composition of [24], wherein the double-stranded molecule has the general formula 5'-[A]-[B]-[A']-3', wherein [A] is the sense strand containing a sequence corresponding to a target sequence selected from among SEQ ID NOs: 9 and 10, [B] is a intervening single-strand composed of 3 to 23 nucleotides, and [A'] is the antisense strand containing a sequence complementary to [A];

[37] The method of [36], wherein the [A] consist of the sequence corresponding to a selected from among SEQ ID NOs: 9 and 10; and

[38] The composition of [24], wherein the composition includes a transfection-enhancing agent and pharmaceutically acceptable carrier.

Suitable compositions of the present invention are described in additional detail below.

The double-stranded molecules of the invention are preferably formulated as pharmaceutical compositions prior to administering to a subject, according to techniques known in the art. Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in Remington's Pharmaceutical Science, 17th ed., Mack Publishing Company, Easton, Pa. (1985), the entire disclosure of which is herein incorporated by reference.

The present pharmaceutical formulations contain at least one of the double-stranded molecules or vectors encoding them of the present invention (e.g., 0.1 to 90% by weight), or a physiologically acceptable salt of the molecule, mixed with a physiologically acceptable carrier medium. Preferred physiologically acceptable carrier media are water, buffered water, normal saline, 0.4% saline, 0.3% glycine, hyaluronic acid and the like.

According to the present invention, the composition may contain plural kinds of the double-stranded molecules, each of the molecules may be directed to the same target sequence, or different target sequences of ZNF224. For example, the composition may contain double-stranded molecules directed to ZNF224. Alternatively, for example, the composition may contain double-stranded molecules directed to one, two or more target sequences of ZNF224.

Furthermore, the present composition may contain a vector coding for one or plural double-stranded molecules. For example, the vector may encode one, two or several kinds of the present double-stranded molecules. Alternatively, the present composition may contain plural kinds of vectors, each of the vectors coding for a different double-stranded molecule.

Moreover, the present double-stranded molecules may be contained as liposomes in the present composition. See under the item of "Methods of inhibiting or reducing growth of a cancer cell and treating cancer using a double-stranded molecule of the present invention" for details of liposomes.

Pharmaceutical compositions of the invention can also include conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can include any of the carriers and excipients listed above and 10-95%, preferably 25-75%, of one or more double-stranded molecule of the invention. A pharmaceutical composition for aerosol (inhalational) administration can include 0.01-20% by weight, preferably 1-10% by weight, of one or more double-stranded molecule of the invention encapsulated in a liposome as described above, and propellant. A carrier can also be included as desired; e.g., lecithin for intranasal delivery.

In addition to the above, the present composition may contain other pharmaceutically active ingredients, so long as they do not inhibit the in vivo function of the double-stranded molecules of the present invention. For example, the composition may contain chemotherapeutic agents conventionally used for treating cancers.

In another embodiment, the present invention provides for the use of the double-stranded nucleic acid molecules of the present invention in manufacturing a pharmaceutical composition for treating a cancer characterized by the expression of ZNF224. For example, the present invention relates to a use of double-stranded nucleic acid molecule inhibiting the expression of a ZNF224 gene in a cell, which molecule includes a sense strand and an antisense strand complementary thereto, hybridized to each other to form the double-stranded nucleic acid molecule and targets to a sequence selected from among SEQ ID NOs: 57 and 58, for manufacturing a pharmaceutical composition for treating cancer expressing ZNF224.

The present invention further provides a method or process for manufacturing a pharmaceutical composition for treating a cancer characterized by the ZNF224 expression, wherein the method or process includes a step for formulating a pharmaceutically or physiologically acceptable carrier with a double-stranded nucleic acid molecule inhibiting the ZNF224 expression in a cell, which over-expresses the gene, which molecule includes a sense strand and an antisense strand complementary thereto, hybridized to each other to form the double-stranded nucleic acid molecule and targets to a sequence selected from among SEQ ID NOs: 57 and 58 as active ingredients.

In another embodiment, the present invention provides a method or process for manufacturing a pharmaceutical composition for treating a cancer characterized by the ZNF224 expression, wherein the method or process includes a step for admixing an active ingredient with a pharmaceutically or physiologically acceptable carrier, wherein the active ingredient is a double-stranded nucleic acid molecule inhibiting the ZNF224 expression in a cell, which over-expresses the gene, which molecule includes a sense strand and an antisense strand complementary thereto, hybridized to each other to form the double-stranded nucleic acid molecule and targets to a sequence selected from among SEQ ID NOs: 57 and 58.

Aspects of the present invention are described in the following examples, which are not intended to limit the scope of the invention described in the claims.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

The invention will be further described in the following examples, which do not limit the scope of the invention described in the claims.

EXAMPLES

I. Materials and Methods

1. Bladder Cancer Cell Lines and Tissue Samples.

Human bladder cancer cell-lines, UM-UC-3 and J82 were purchased from American Type Culture Collection (ATCC; Rockville, Md.). All of bladder cancer cell-lines as well as COS-7 cells were grown in monolayer in appropriate medium as described previously (Takata R, et al., Semin Oncol 1999 Suppl 2:117-22). Tissue samples from surgically-resected invasive or superficial bladder cancers, and their corresponding clinical information were obtained from five hospitals, Kochi Medical School, Kyoto Prefectural University of Medicine, Nagoya City University Graduate School of Medical Sciences, Kanazawa University Graduate School of Medical Sciences, and Iwate Medical University, with written informed consent.

2. Identification of DEPDC1-Interacting Proteins.

Cell extracts from bladder cancer cell line UM-UC-3 were precleared by incubation at 4 degrees C. for 1 h with 100 micro L of protein G-agarose beads in a final volume of 1 mL of immunoprecipitation buffer (0.5% NP-40, 50 mM Tris-HCl, 150 mM NaCl) in the presence of proteinase inhibitor. After centrifugation at 80 g for 5 min at 4 degrees C., the supernatant was incubated at 4 degrees C. with anti-DEPDC1 polyclonal antibody or normal rabbit IgG for 2 h. The beads were then collected by centrifugation at 2000 g for 2 min and washed five times with 1 mL of each immunoprecipitation buffer. The washed beads were resuspended in 50 micro L of Laemmli sample buffer and boiled for 5 min, and the proteins were separated in 5-20% SDS polyacrylamide gel electrophoresis (PAGE) gels (Bio-Rad, Hercules, Calif.). After electrophoresis, the gels were stained with silver. Protein bands specifically found in extracts immunoprecipitated with anti-DEPDC1 polyclonal antibody were excised and served for matrix-assisted laser desorption/ionization-time of flight mass spectrometry (MALDI-TOF-MS) analysis (AXIMA-CFR plus, SHIMADZU BIOTECH).

3. Semi-Quantitative Reverse Transcription-PCR.

Microdissection of bladder cancer cells was performed as described previously (Takata R, et al., Semin Oncol 1999 Suppl 2:117-22). The present inventors prepared total RNA extracted from cultured cells and each of microdissected bladder clinical samples and normal human bladder epithelial cells using RNeasy Micro Kits (Qiagen, Valencia, Calif.), and polyA (+) RNAs isolated from heart, lung, liver, kidney and bladder (Takara Clontech, Kyoto, Japan). Subsequently, T7-based amplification and reverse transcription was performed as described previously (Takata R, et al., Semin Oncol 1999 Suppl 2:117-22). Appropriate dilutions of each single-stranded cDNA were prepared for subsequent PCR by monitoring an amount of glyceraldehyde-3-phosphate dehydrogenase (GAPDH) as a quantitative control. The sequences of each set of primer were as follows;

```
ZNF224:
                                     (SEQ ID NO: 1)
5'-GAGCAGCAT GGGAAGAACAT-3'
and (SEQ ID NO: 2)
5'-TGAGGCCTGACTAAAGCACA-3';

GAPDH:
                                     (SEQ ID NO: 3)
5'-CGACCACTTTGTCAAGCTCA-3'
and (SEQ ID NO: 4)
5'-GGTTGAGCACAGGGTACTTTATT-3';

DEPDC1:
                                     (SEQ ID NO: 59)
5'-GCTACAAGTAAAGAGGGGATGG-3'
and (SEQ ID NO: 60)
5'-GGACAGAAAGGTAAGTCAGTGGG-3';

IkB-alpha;
                                     (SEQ ID NO: 61)
5'-TATATCCACACTGCACACTGC-3'
and (SEQ ID NO: 62)
5'-CCATTTACAGGAGGGTAACAC-3'.
```

4. Construction of the Expression Vectors.

The cDNAs corresponding to open reading frame sequences of ZNF224 and a part of coding sequences of DEPDC1 were obtained by PCR using KOD-Plus DNA polymerase (TOYOBO, Osaka, Japan) with primers as follows. ZNF224-forward:

```
                                     (SEQ ID NO: 5)
5'-GGAAAGCGGCCGCATGACCACGTTCAA-3',

ZNF224-reverse:
                                     (SEQ ID NO: 6)
5'-GCCGCTCGAGAGGTTTTTCTCCAACATGAA-3', DEPDC1_{1-147}-forward:
                                     (SEQ ID NO: 63)
5'-ATTCGCGGCCGCGGATGGAGAGTCAGGGTGTG-3', DEPDC1_{1-147}-reverse:
                                     (SEQ ID NO: 64)
5'-CCCGCTCGAGAGTTCTACGAGATAAGTTTCG-3', DEPDC1_{1-300}-forward:
```

-continued

DEPDC1₁₋₃₀₀-forward:
(SEQ ID NO: 65)
5'-ATTCGCGGCCGCGGATGGAGAGTCAGGGTGTG-3',

DEPDC1₁₋₃₀₀-reverse:
(SEQ ID NO: 66)
5'-CCCGCTCGAGTACAAATAATTCGTAATATTC-3',

DEPDC1₁₇₇₋₅₉₇-forward:
(SEQ ID NO: 67)
5'-ATTCGCGGCCGC TTGATAATAGAGAACTAAGCCA-3', DEPDC1₁₇₇₋₅₉₇-reverse:
(SEQ ID NO: 68)
5'-CCCGCTCGAGAACCCTCTCTAAATGAGGTTG-3', DEPDC1₃₀₀₋₆₆₉-forward:
(SEQ ID NO: 69)
5'-ATTCGCGGCCGC ACCATGGTAAACATTTTG-GTTGTTTGTG-3', DEPDC1₃₀₀₋₆₆₉-reverse:
(SEQ ID NO: 70)
5'-CCCGCTCGAGTCCAGCAAGAAGCTCATC-3', DEPDC1₅₈₇₋₇₄₀-forward:
(SEQ ID NO: 71)
5'-ATTCGCGGCCGC ACCATGCAAAGCTTGCTG-CAACCTCA-3', DEPDC1₅₈₇₋₇₄₀-reverse:
(SEQ ID NO: 72)
5'-CCCGCTCGAGAGCTTGAGAGGTAGAAAC-3', DEPDC1₆₅₄₋₈₁₁-forward:
(SEQ ID NO: 73)
5'-ATTCGCGGCCGC ACCATGTCTTACTTACA-GACTGCAGTG-3', DEPDC1₆₅₄₋₈₁₁-reverse:
(SEQ ID NO: 74)
5'-CCCGCTCGAGTCTTAGACTACGGAACTTTG-3'.

The underlines of forward primers indicate NotI site and the underlines of reverse primers indicate XhoI site.

The PCR products were inserted into the NotI-XhoI sites of pCAGGScFLAG and pCAGGScHA expression vector in frame with C-terminal FLAG-tag for ZNF224 (pCAGGSc-ZNF224-FLAG), or HA-tag for partial peptide of DEPDC1 (pCAGGSc-DEPDC1-HA; DEPDC1₁₋₁₄₇, DEPDC1₁₋₃₀₀, DEPDC1₁₇₇₋₅₉₇, DEPDC1₃₀₀₋₆₆₉, DEPDC1₅₈₇₋₇₄₀, and DEPDC1₆₅₄₋₈₁₁). All of the constructs were confirmed by DNA sequencing with ABI 3700 DNA sequencer (Applied Biosystems, Forster City, Calif.). The entire coding region of DEPDC1 construct (pCAGGS-DEPDC1-V1-HA) was generated as described previously (Kanehira M, Harada Y, Takata R, et al. Oncogene 2007; 26:6448-55.).

5. Immunocytochemical Staining Analysis

UM-UC-3 cells were seeded at 1×10⁵ cells per well (Labtek II chamber slide, Nalgen Nunc, International, Naperville, Ill.). At 24 hours later, cells were transiently transfected with Flag-tagged ZNF224. Forty eight hours after the transfection, cells were fixed with PBS (−) containing 4% paraformaldehyde, and then rendered permeable with PBS (−) containing 0.1% Triton X-100 for 2 min at room temperature. Subsequently, the cells were covered with 3% BSA in PBS (−) for 12 hours at 4 degrees C. to block nonspecific hybridization. Then, cells were incubated with affinity-purified anti-DEPDC1 or anti-ZNF224 polyclonal antibodies diluted 1:100 in the blocking solution. After washing with PBS (−), the cells were stained by an Alexa488-conjugated and Alexa597-conjugated anti-rabbit secondary antibody (Molecular Probe, Eugene, Oreg.) at 1:1000 dilutions. Nuclei were counter-stained with 4',6'-diamidino-2'-phenylindole dihydrochloride (DAPI). Fluorescent images were obtained under a TCS SP2 AOBS microscope (Leica, Tokyo, Japan).

For detection of NF-kappaB expression in the nucleus after treatment with dominant-negative peptide (see "Dominant-negative peptide section"), UM-UC-3 cells (1×10⁵) were seeded and then treated with each peptide for 12 hours. Subsequently, immunocytochemical staining was performed using anti-NF-kappaB (p65) monoclonal antibody (diluted at 1:200) (Santa Cruz, Calif., USA). Fluorescent images and nuclear intensity of NF-kappaB (p65) protein were obtained under a TCS SP2 AOBS microscope (Leica, Tokyo, Japan). For the image analysis, the nuclear signal intensities of NF-kappaB (p65) were measured by observing nuclei of 50 cells treated with the 11R-DEP₆₁₁₋₆₂₈ peptide or scramble peptide (see "Dominant-negative peptide section"). Assays were performed in triplicate independently.

6. RNA Interference Assay.

It has been previously established a vector-based RNA interference (RNAi) system, psiU6BX3.0 that was designed to express small interfering RNAs (siRNA) in mammalian cells (Shimokawa T, et al., Cancer Res 2003 63:6116-20). Plasmids designed to express siRNA to ZNF224 were prepared by cloning of double-stranded oligonucleotides into the BbsI site of psiU6BX vectors. The target sequences of the synthetic oligonucleotides for RNAi were as follows:

EGFP (enhanced green fluorescent protein gene, a mutant of Aequorea Victoria green fluorescent protein): 5'-GAAG-CAGCACGACTTCTTC-3' (SEQ ID NO: 7);

SCR (chloroplast Euglena gracilis gene coding for 5S and 16S rRNAs): 5'-GCGCGCTTTGTAGGATTCG-3' (SEQ ID NO: 8), as a control;

si-ZNF224#1: 5'-CCGATTTGGATGATGAAGA-3' (SEQ ID NO: 9);

si-ZNF224#2: 5'-CCGCAGGAACACATCAAGA-3' (SEQ ID NO: 10) for the ZNF224-specific sequence. DNA sequences of all constructs were confirmed by DNA sequencing. Eight-micrograms each of siRNA-expression vector were transfected into UM-UC-3 cells (1×10⁶ cells per 10 cm-dish), respectively, using FuGENE6 transfection reagent (Roche) according to the supplier's recommendations. To evaluate the knockdown effect of siRNAs by semi-quantitative RT-PCR with specific primers (see below), total RNAs were extracted from the transfected cells after 4-day incubation with neomycin (Geneticin, Invitrogen). The specific primer sets for RT-PCR are as follows; 5'-GAGCAGCATGG-GAAGAACAT-3' (SEQ ID NO: 11) and 5'-TGAGGCCT-GACTAAAGCACA-3' (SEQ ID NO: 12) for ZNF224;

5'-CGACCACTTTGTCAAGCTCA-3' (SEQ ID NO: 13) and 5'-GGTTGAGCACAGGGTACTTTATT-3' (SEQ ID NO: 14) for GAPDH as a quantitative control. The transfected UM-UC-3 cells were cultured for 21 or 14 days in the presence of 1.0 mg/ml of neomycin, and the number of colonies were counted by Giemsa staining. Viability of UM-UC-3 cells was evaluated by 3-(4,5-dimethylthiazol-2-yl)-2,5-diphenyltetrazolium bromide (MTT) assay at 14 days after the treatment of neomycin with cell counting kit-8 according to manufacturer's recommendation (Wako, Osaka, Japan). Absorbance at 570 nm wavelength was measured with a Microplate Reader 550 (Bio-Rad, Hercules, Calif.). These experiments were performed in triplicate.

7. Identification of Downstream Genes of DEPDC1/ZNF224 by cDNA Microarray.

UM-UC-3 cells were transfected with siRNA against DEPDC1 (si-DEPDC1), ZNF224 (si-ZNF224-2) or EGFP (control siRNA). The target sequences of the synthetic oligoduplex for siRNA against DEPDC1 (Sigma Aldrich) were as follows: si-DEPDC1,5'-CCAAAGUUCCGUAGUCUAA-3' (SEQ ID NO: 75), ZNF224 (si-ZNF224-2) or EGFP as described in "RNA interference assay" section.

Total RNAs were extracted from each sample at 12 hours and 24 hours after the transfection, labeled with Cy5 (for si-DEPDC1- and si-ZNF224-2-transfected cells) or Cy3 (for si-EGFP-transfected cells), and subjected to cohybridization onto cDNA microarrayslides containing 36468 cDNA or ESTs as described previously (Takata R, et al., Clin Cancer Res 2005 11:2625-36). After normalization of the data, it was excluded genes from further analysis when Cy5 and Cy3 dyes yielded signals intensities lower than the cut-off value. For other genes, the Cy5/Cy3 ratio was calculated using the raw data of each samples. Genes whose intensity was significantly increased in accordance with the reduction of both DEPDC1 and ZNF224 expression were initially selected. Validation of candidate downstream genes of both DEPDC1 and ZNF224 was carried out with quantitative RT-PCR analysis using the SYBR green dye (Rhoche) and the same amplified RNAs from UM-UC-3 cells used for cDNA microarray experiments, with each gene-specific primer as follows;

```
DLG1,
                              (SEQ ID NO: 15)
5'-ATGGTGAGAGCGATGAGGTC-3'
and (SEQ ID NO: 16)
5'-AATCGGGCTCGTTCTTTCTT-3';

A20,
                              (SEQ ID NO: 76)
5'-TGCACACTGTGTTTCATCGAG-3'
and (SEQ ID NO: 77)
5'-ACGCTGTGGGACTGACTTTC-3;

beta 2-MG (control),
                              (SEQ ID NO: 17)
5'-TCTCTCTTTCTGGCCTGGAG-3'
and (SEQ ID NO: 18)
5'-AATGTCGGATGGATGAAACC-3'.
```

All experiments were performed in duplicate. The calculated quantity of the target gene for each sample was then divided by the average calculated quantity of beta 2-microglobulin (beta 2-MG) corresponding to each sample to give a relative expression of the target gene for each sample 8. Luciferase Reporter Assay for DLG1

The fragment of the DLG1 promoter (position −1211 to +19) was amplified by PCR using the following primers:
5'-GATCACGCGTCACCGTTTGACCCTTCTATC-3' (SEQ ID NO: 19) (underline indicates MluI site) and
5'-GATCCTCGAGCAGCAGTGCCGTTTCCAACT-3' (SEQ ID NO: 20) (underline indicates XhoI site), and cloned into the pGL3-enhancer luciferase reporter vector (Promega, Madison, Wis.). Cos7 cells were co-transfected with either 1.6 micro g of pGL3-enhancer-DLG1 or mock vector in combination with 1.6 micro g of the pRL-TK-promoter vector using FuGENE6 regent (Roche). At 48 h after transfection, cells were rinsed with PBS(−) and lysed with a passive lysis buffer (Promega). Lysates were used directly in the Dual Luciferase assay system (Promega), which depends on sequential measurements of firefly ad Renilla luciferase activities in specific substrates. Quantification of luciferase activities and calculations of relative ratios were performed manually with the Dual-Light kit (Tropix, Bedford, Mass.).

9. Luciferase Reporter Assay for A20

The fragment of the A20 promoter (position −330 to −35) was amplified by PCR using the following primers: 5'-GATC ACGCGT AGCCCGACCCAGA-GAGTCACGT-3' (SEQ ID NO: 78)(underline indicates MluI site) and 5'-GATC CTCGAGCTTTCGCAAAGTCCCAAGTC-3' (SEQ ID NO: 79) (underline indicates XhoI site), and cloned into the pGL3-enhancer luciferase reporter vector (Promega, Madison, Wis.). NHDF cells were co-transfected with either 1 micro g of pGL3-enhancer-A20 promoter or mock vector in combination with 0.5 micro g of the pRL-TK-promoter vector using Human Dermal Fibroblast Nucleofector kit (Lonza, N.J., USA). After 24 hours, luciferase activity was measured using Dual-Luciferase Reporter Assay Kit (Toyo Ink, Tokyo, Japan). A renilla-expressing plasmid was used to normalize for transfection efficiency. Quantification of luciferase activities and calculations of relative ratios were performed automatically with the Luminometer (EG&G Berthold, Bad Wildbad, Germany). These experiments were performed in triplicate.

10. Identification of the ZNF224-Binding Regions in DEPDC1.

To confirm the interaction between DEPDC1 and ZNF224 in bladder cancer cells and identify the ZNF224-binding region in DEPDC1, the immunoprecipitation experiment was carried out as follows. First, it was confirmed interaction between endogenous DEPDC1 and exogenous ZNF224 by immunoprecipitation experiments using anti-DEPDC1 polyclonal antibody for immunoprecipitation and anti-FLAGM2 antibody (Amersham) for immunoblotting. To further determine the ZNF224-binding region in DEPDC1, it was cloned six partial constructs of DEPDC1 ($DEPDC1_{1-147}$, $DEPDC1_{141-300}$, $DEPDC1_{177-597}$, $DEPDC1_{300-669}$, $DEPDC1_{587-740}$ and $DEPDC1_{654-811}$) into appropriate sites of COOH-terminal HA-tagged pCAGGS vector. The nucleotide sequence of each clones were determined with an ABI Prism 3700 DNA sequencer (Applied Biosystems, Foster City, Calif.), using each primer. Cell extracts from Cos7 cell line, transfected with each of plasmids expressing one of these six partial segments of DEPDC1, were precleared by incubation at 4 degrees C. for 1 hour with 100 micro l of protein G-agarose beads in final volumes of 2 mL of immunoprecipitation buffer (0.5% NP40, 50 mmol/L Tris-HCl, 150 mmol/L NaCl) in the presence of proteinase inhibitor. After centrifugation at 1,000 rpm for 5 minutes at 4 degrees C., the supernatants were incubated at 4 degrees C. with anti-HA rat for 1 hours. After the beads were collected from each sample by centrifugation at 5,000 rpm for 2 minutes and washed six times with 1 mL of immunoprecipitation buffer, the washed beads were re-suspended in 50 uL of Laemmli sample buffer and boiled for 3 minutes before the proteins were separated on 10% SDS-PAGE gels. Immunoblot was done using anti-HA rat antibody and anti-FLAGM2 monoclonal antibody, respectively (Sigma-Aldrich Co., St. Louis, Mo.).

11. Synthesized Dominant-Negative Peptide.

Eighteen-amino-acid sequence derived from two minimized ZNF224-binding domain in DEPDC1 (codons 148-176 ($1^{st}$ region) and codons 598-653 ($2^{nd}$ region); see FIG. 4A) was covalently linked at its $NH_2$ terminus to a membrane transducing 11 poly-arginine sequence (11R). Four dominant-negative peptides were synthesized covering the codons 148-176 region ($1^{st}$ region):

```
$DEPDC1_{148-166}$,
                              (SEQ ID NO: 21)
RRRRRRRRRRR-GGG-PKRHGLHLSQENGEKIKHE;

$DEPDC1_{159-176}$,
                              (SEQ ID NO: 22)
RRRRRRRRRRR-GGG-NGEKIKHEIINEDQENAI,
and the codons 598-653 region ($2^{nd}$ region):
```

-continued

DEPDC1_598-615,
RRRRRRRRRRR-GGG-AIDALQLCCLLLPPPNRR; (SEQ ID NO: 23)

DEPDC1_611-628
RRRRRRRRRRR-GGG-PPNRRKLQLLMRMISRMS; (SEQ ID NO: 24)

DEPDC1_624-641
RRRRRRRRRRR-GGG-ISRMSQNVDMPKLHDAMG; (SEQ ID NO: 25)

DEPDC1_636-653
RRRRRRRRRRR-GGG-LHDAMGTRSLMIHTFSRC. (SEQ ID NO: 26)

Scramble peptides derived from the most effective DEPDC1_611-639 peptides were synthesized as a control:

Scramble_611-628, RRRRRRRRRRR-GGG-LRMSRLSPNMIMQRPKRL (SEQ ID NO: 27). Peptides were purified by preparative reverse-phase high-performance liquid chromatography and were >90% purity.

To examine the effect of these polyarginine (11R)-linked peptides on inhibition of the DEPDC1-ZNF224 complex formation, they were co-transfected with DEPDC1 and ZNF224 constructs into COS7 cells. Six hours after the transfection, cells were incubated in the media containing each of the four peptides at the concentration of 3 micro M for 24 hours. Immunoprecipitation were performed according to methods as described in "Identification of the ZNF224-binding regions in DEPDC1 protein" section.

UM-UC-3 and normal human dermal fibroblast-derived NHDF-Ad cell lines were incubated with the 11R peptides at the concentration of 0, 1, 2, or 3 micromol/L for 5 days. Each peptide was added at every 24 hours at the appropriate concentrations and the viability of cells was evaluated by MTT assay at every day after the treatment.

12. Western Blot Analysis.

To detect the expression of endogenous DEPDC1 and ZNF224 proteins in a bladder cancer (UM-UC-3) and normal human cell-lines (HEK293, HMEC, SAEC and NHDF-Ad), each of these cells was incubated in lysis buffer (50 mM Tris-HCL (pH 8.0)/150 mM NaCL/0.5% NP-40) including 0.1% protease inhibitor cocktail III (Calbiochem, San Diego, Calif.). The amount of total protein was estimated by protein assay kit (Bio-Rad, Hercules, Calif.), and then proteins were mixed with SDS-sample buffer and boiled for 3 min before loading at 10% SDS-PAGE gel. After electrophoresis, the proteins were blotted onto nitrocellulose membrane (GE Healthcare, Buckinghamshire, United Kingdom). After blocking with 4% BlockAce (Dainippon Pharmaceutical. Co., Ltd, Osaka, Japan), membranes were incubated with anti-DEP11DC1 polyclonal antibody or anti-ZNF224 polyclonal antibody (Abcam) for detection of the endogenous DEPDC1 or ZEF224 proteins, respectively. Finally the membrane was incubated with HRP conjugated-secondary antibody, and bands were visualized by ECL detection reagents (GE Healthcare). beta-actin (ACTB) served as a loading control. To detect the expression of endogenous A20 and IkB-alpha proteins after treatment of cell-permeable peptides (see below), experiments were performed using anti-A20 (TN-FAIP3) monoclonal antibody (diluted at 1:50) (59A426; Abcam) and anti-IkB-alpha monoclonal antibody (diluted at 1:100) (C-15; BD Biosciences, San Jose, Calif., USA).

13. Cell Cycle Analysis.

Cells were analyzed after that 6 hr exposure to nocodazole and 16 hrs treatment with dominant-negative peptide DEPDC1_611-628. Cells were harvested by trypsinization, washed with PBS, fixed and stored at 4 degrees C. before DNA analysis. After removal of ethanol by centrifugation, cells were incubated with RNase at 37 degrees C. for 30 min. After centrifugation, cells were then stained with a propidium iodide (PI) solution for 1 hr. Stained nuclei were analyzed for DNA-PI fluorescence using a Becton Dickinson FACScan flow cytometer. Resulting DNA distributions were analyzed by Modfit (Verity Software House, Topsham, Me.) for the proportion of cells in sub-G0, G1, S and G2-M phases of the cell cycle.

14. Cell Proliferation Assay.

To examine the effect of DEPDC1 and ZNF224 on cell growth, UM-UC-3 cells ($1\times10^6$ cells/10 cm-dish) were transfected with 8-microgram each of pCAGGSn-DEPDC1-HA or pCAGGSn-ZNF224-FLAG or both using FuGENE6 transfection reagent (Roche). After 24 hours later, cells were reseeded in 10 cm-dish plates at a density of $1\times10^6$ cells/dish, and cultured with EMEM containing 1 mg/mL neomycin (Geneticin, Invitrogen, Carlsbad, Calif., USA) for 5 more days. Viability of UM-UC-3 cells evaluated by MTT assays at 7 days after the treatment of neomycin with cell counting kit-8 according to the manufacturer's recommendation (Wako). Absorbance at 570 nm wavelength was measured with a Microplate Reader 550 (Bio-Rad). These experiments were performed in duplicate.

15. Inhibition of Bladder Cancer Cell Growth.

To examine the effect of DEPDC1_611-628 peptide on cell growth of UM-UC-3 and NHDF cells, the cells were incubated with the DEPDC1_611-628 or scramble peptides at the concentration of 0, 1, 2, or 3 micro M for 5 days, respectively. Each peptide was added at every 24 hours at the appropriate concentrations and the viability of cells was evaluated by MTT assay every day. Absorbance at 570 nm wavelength was measured with a Microplate Reader 550 (Bio-Rad). These experiments were performed in triplicate.

16. Analysis of Apoptosis.

UM-UC-3 cells were incubated for 12 hours after treatment with DEPDC1_611-628 or scramble peptides. For TUNEL assay, the cells were evaluated using an Apoptosis in situ Detection kit according to the supplier's recommendation (Wako, Osaka, Japan). The apoptotic cells were observed with a TCS SP2 AOBS microscopy. The TUNEL positivity was determined by observing 200 cells at random for each experiment. Assays were performed in triplicate independently.

17. Chromatin immunoprecipitation (ChIP) assay.

HEK293 cells were seeded at $4\times10^6$ cells per 15 cm-dish (Becton Dickinson, N.J., USA). At 24 hours later, cells were transiently co-transfected with HA-tagged DEPDC1 and FLAG-tagged ZNF224 constructs using FuGENE6 transfection reagent (Roche). Twenty-four hours later, cells were crosslinked with 1% formaldehyde for 10 min at 37 degrees C. The fixed chromatin samples were subjected to immunoprecipitation using chromatin immunoprecipitation (ChIP) assay kit (Upstate, Charlottsvile, Va.), as recommended by the manufacturer, except that anti-HA-tag antibody was used herein. The recovered DNA was analyzed using the following primers: 5'-AGCCCGACCCAGAGAGTCACGT-3' (SEQ ID NO: 80) and 5'-CTTTCGCAAAGTCCCAAGTC-3'(SEQ ID NO: 81) that covered the A20 promoter region (position −330 to −35).

18. Statistical Analysis.

Statistical significance was determined by Student's t test, using Statview 5.0 software (SAS Institute, Cary, N.C.). A difference of $P<0.05$ was considered to be statistically significant.

II. Results

1. Identification of a Molecule Interacting with DEPDC1.

It was previously demonstrated that DEPDC1 was involved in bladder cancer cell survival or growth by siRNA experiments (Kanehira M, et al., Oncogene 2007 26:6448-55). However, its precise molecular mechanism was still unknown. To elucidate its biological functions in bladder cancer cells, proteins interacting with DEPDC1 were searched by immunoprecipitation and mass spectrometry analyses. Cell extracts from UM-UC-3 cells were immunoprecipitated with anti-DEPDC1 antibody or rabbit IgG (negative control). Protein complexes were silver-stained on SDS-PAGE gels. An approximately 93-kDa protein, which was seen in immunoprecipitates by anti-DEPDC1 antibody, but not in those by rabbit IgG, was extracted and its peptide sequences were determined by MALDI-TOF analysis (data not shown). This approach defined this protein to be zinc finger protein 224 (ZNF224), a Kuruppel-associated box-containing zinc-finger protein (Medugno L, et al., FEBS Lett. 2003 534: 93-100), as a candidate interacting with DEPDC1. The expression levels of ZNF224 in clinical bladder cancer cases was first investigated by semiquantitative RT-PCR analysis; coupregulation of ZNF224 and DEPDC1 was observed in 9 of 10 bladder cancer cases (FIG. 1A). To validate this interaction, a plasmid designed to express FLAG-tagged ZNF224 (ZNF224-FLAG) was constructed and coimmunoprecipitation experiments was performed (see Materials and Methods). This construct plasmid was transfected into UM-UC-3 bladder cancer cells, and the proteins were immunoprecipitated with anti-FLAG antibody. Immunoblotting of the precipitates with rabbit anti-DEPDC1 antibody revealed that endogenous DEPDC1 was coprecipitated with ZNF224-FLAG protein (FIG. 1B). Furthermore, subcellular-localization of DEPDC1 and ZNF224 when the ZNF224-FLAG construct was transfected into UM-UC-3 cells was examined. FIG. 1C revealed that endogenous DEPDC1 co-localized with exogenous ZNF224 at nucleus of cells, implying their interaction in nucleus of bladder cancer cells.

2. Growth Inhibitory Effects of ZNF224-Specific siRNA in Bladder Cancer Cells

To further investigate the biological significance of ZNF224 as a DEPDC1-interacting partner in bladder carcinogenesis, ZNF224-specific siRNA expression vectors was constructed, and the knockdown effect of each construct in UM-UC-3 bladder cancer cells was examined; overexpression of ZNF224 was observed. Semiquantitative RT-PCR analysis showed that the ZNF224-specific siRNAs (si-ZNF224-1 and si-ZNF224-2) significantly suppressed the amount of ZNF224 transcript, as compared with si-EGFP as a control (FIG. 2 upper left). MTT and colony-formation assays (FIG. 2 bottom left) were then performed. It was discovered that introduction of si-ZNF224-1 and si-ZNF224-2 resulted in marked suppression growth of UM-UC-3 cell (si-ZNF224-1, P=0.000019 or si-ZNF224-2, P=0.00013, student t test), in concordance with the results of the knockdown effect (FIG. 2 right panel). Such results clearly indicate that ZNF224 is likely to have crucial roles on growth of bladder cancer cells.

3. Identification of Common Downstream Genes for DEPDC1 and ZNF224.

ZNF224 is reported to belong to the regulatory Kruppel-like zinc finger protein family, a family whose members are known to function as transcriptional repressors (Medugno L, et al., FEBS Lett 2003 534:93-100). It has further been reported that ZNF224 inhibits Wilms tumor suppressor (WT1) protein-mediated transcriptional activation though its interaction with WT1 (Lee T H, et al., J Biol Chem 2002 277:44826-37), indicating that ZNF224 is considered to be a transcriptional repressor. Therefore, the identification of downstream genes regulated by DEPDC1/ZNF224 complexes in bladder cancer cells was sought. siRNA-DEPDC1, siRNA-ZNF224 or siRNA-EGFP (control siRNA) was transfected into UM-UC-3 bladder cancer cells, in which DEPDC1 and ZNF224 were highly expressed, and alterations in gene expression at various time points were monitored using cDNA microarray analysis consisting of 36468 genes. Moreover, genes whose expression was significantly down-regulated in clinical bladder cancer specimens were selected through the cDNA microarray data (Takata R, et al., Clin Cancer Res 2005 11:2625-36). DLG1 and A20 (also known as TNFAIP3) were identified as candidate downstream genes in the DEPDC1/ZNF224 complex. Quantitative RT-PCR analysis confirmed the time-dependent increase of both transcripts in UM-UC-3 cells transfected with si-DEPDC1 and si-ZNF224, respectively, compared with the cells transfected with siEGFP (FIG. 3A). Particularly, repression of DLG1 expression was detected by co-transfection of DEPDC1 and ZNF224 in UM-UC-3 (FIG. 3B). Moreover, the inhibition of transactivation of DLG1 promoter by only DEPDC1/ZNF224 co-transfection using Luciferase assay system was recognized (FIG. 3C). These results suggest that DEPDC1/ZNF224 complex can represses transcription of tumor suppressive genes.

4. Identification of the ZNF224-Binding Region in DEPDC1.

The biological importance of the association of these two proteins and their potential as therapeutic targets for bladder cancer was subsequently investigated. First, to determine the domain in DEPDC1 that is required for interaction with ZNF224, one of six partial constructs of DEPDC1 with HA-tag sequence at its COOH-terminal (DEPDC1$_{1-147}$, DEPDC1$_{141-300}$, DEPDC1$_{177-597}$, DEPDC1$_{300-669}$, DEPDC1$_{587-740}$, and DEPDC1$_{654-811}$; FIG. 4A, FIG. 9A) and Flag-tagged ZNF224 (ZNF224-Flag) were co-transfected into Cos7 cells. Immunoprecipitation with monoclonal anti-HA rat antibody indicated that DEPDC1$_{141-300}$, DEPDC1$_{300-669}$, and DEPDC1$_{587-740}$ were able to interact with ZNF224, but DEPDC1$_{1-147}$, DEPDC1$_{177-597}$ and DEPDC1$_{654-811}$ were unable to ZNF224 (FIG. 4B, FIG. 9B). These findings suggest that the NH$_2$-terminal 29-amino-acid polypeptides (codons 148-176) and COOH-terminal 56-amino-acid polypeptides (codons 598-653) in DEPDC1 plays an important role in the interaction with ZNF224.

5. Growth Inhibition of Bladder Cancer Cells by Dominant-Negative Peptides of DEPDC1.

As shown above, the NH$_2$-terminal portion 29-amino-acid peptides of DEPDC1$_{148-176}$ and COOH-terminal portion 56-amino-acid peptides of DEPDC1$_{598-653}$ were presumed to contain the region to interact with ZNF224. Therefore, in order to develop the bioactive cell-permeable peptides that can inhibit the functional association of DEPDC1 with ZNF224, six different kinds of 18-amino-acid polypeptides covering the ZNF224-binding domains in DEPDC1$_{148-176}$ and DEPDC1$_{598-653}$ that was added a membrane-permeable 11 residues of arginine (11R) at its NH$_2$ terminus were synthesized. To test the inhibitory effects of these polyarginine peptides on bladder cancer cell growth or survival, a UM-UC-3 cell line was treated with each of the six peptides. Various concentrations of the six peptides were treated into the culture media, and it was discovered that 11R-DEP$_{611-628}$ peptide resulted in significant decreases in cell viability in dose-dependent manner, as measured by MTT assay (FIG. 5A; P<0.001 for 1.0 microM, 2.0 microM and 3.0 microM peptide treatment by unpaired t test), and 11R-DEP$_{598-615}$ peptide caused in moderate suppress in cell viability in dose-dependent manner.

To examine whether 11R-DEP$_{611-628}$ peptide inhibit the complex formation between exogenously expressed DEPDC1-HA and ZNF224-Flag in COS7 cells, COS7 cells were treated with each of the six peptides at 6 hours after transfection. Fifteen hours later, the immunoprecipitated was performed with anti-HA-tag antibody, and then western blot analysis was performed with anti-Flag antibody. FIG. 5B showed that 11R-DEP$_{611-628}$ peptide could inhibit the complex formation between exogenously expressed DEPDC1-HA and ZNF224-Flag in COS7 cells (FIG. 5B), but not inhibit by treatment of scramble$_{611-628}$ peptide (FIG. 5E). Suppression of cell viability of J82 cells was further demonstrated (FIG. 5F). It was further confirmed that treatment with the other peptides such as 11R-DEP$_{148-166}$, 11R-DEP$_{159-176}$, 11R-DEP$_{611-628}$, 11R-DEP$_{624-641}$ and 11R-DEP$_{636-653}$ within the two binding regions resulted in no inhibition (FIG. 5G), although treatment of 11R-DEP$_{598-615}$ peptide led to the slight inhibition of their interaction in accordance with MTT-assay results as shown in FIG. 5A. 11R-DEP$_{611-628}$ peptide revealed no effect on cell viability of Normal Human Dermal Fibroblasts Cells (Adult) derived NHDF-Ad cells that expressed a hardly detectable level of DEPDC1 and ZNF224 (FIGS. 5C and D bottom panel). Furthermore, no alterations in cell growth or cellular morphology were observed in cells treated with scramble$_{611-628}$ peptide (FIG. 5D). These inventions suggest that transducible 11R-DEP$_{611-628}$ peptide could inhibit a functional complex formation of DEPDC1 and ZNF224 and have no toxic effect on normal human cells that do not express these proteins.

6. Repression of Candidate Downstream Genes of DEPDC1-ZNF224 Complex after treatment of 11R-DEP$_{611-628}$ peptide.

To clarify the mechanism of tumor suppression by 11R-DEP$_{611-628}$ peptides, expression of candidate downstream genes of DEPDC1-ZNF224 complex was examined by quantitative RT-PCR analysis. Expression of DLG1 and A20 was shown to be enhanced by treatment of peptide, but not by treatment of scramble$_{611-628}$ peptide (FIG. 6A, B). Furthermore, flow cytometric analysis of the tumor cells treated with these peptides was performed, and it was discovered that the cells caused the G1-S arrest and G1 fraction at 24 hours after the treatment was significantly increased (FIG. 6B).

7. Oncogenic Activity of the DEPDC1-ZNF224 Complex.

To further examine the growth-promoting effect of the DEPDC1-ZNF224 complex, HA-tagged DEPDC1, FLAG-tagged ZNF224 or both was transfected into UM-UC-3 cells, and then investigated cell viability by MTT assay. It was confirmed the expression of exogenous DEPDC1-HA and ZNF224-FLAG proteins by western blot analysis using anti-HA and anti-FLAG antibodies (FIG. 8, lower panels). Double-transfected UM-UC-3 cells showed much higher cell proliferation than those transfected with DEPDC1 alone or ZNF224 alone, in comparison with those transfected with mock plasmid (P<0.05, unpaired t test; FIG. 8, upper panel). Taken together, our results imply that the DEPDC1-ZNF224 complex is likely to play crucial roles on bladder carcinogenesis.

8. Growth Inhibitory Effects of R11-DEP611-628 Peptide.

To examine a possibility of the dominant-negative effect of the cell-permeable peptides on inhibition of the interaction between DEPDC1 and ZNF224, the present inventors synthesized four 18-amino-acid polypeptides, that could cover the DEPDC1$_{598-653}$, the ZNF224-binding domain, with a membrane-permeable 11 residues of arginine (11R) at its NH$_2$ terminus. The present inventors investigated the effect of these peptides on the protein-protein interaction as well as bladder cancer cell growth. First, the DEPDC1-HA and ZNF224-FLAG constructs into COS7 cells were co-transfected, and then treated cells with each of the four peptides at 6 hours after the transfection. Twenty-four hours later, we performed the immunoprecipitation experiments with anti-HA-tag antibody and the subsequent western blot analysis with anti-FLAG antibody. It was demonstrated that treatment of 11R-DEP$_{611-628}$ clearly inhibited the complex formation of DEPDC1-HA and ZNF224-FLAG in COS7 cells, and that of 11R-DEP$_{598-615}$ revealed moderate effect, while other peptides showed no effect on their complex formation (FIG. 7A). Moreover, it was confirmed the specificity of 11R-DEP$_{611-628}$ to inhibition of their complex formation by confirming no effect by the scramble sequence peptide of 11R-DEP$_{611-628}$ (scramble) (FIG. 5B).

Furthermore, addition of the 11R-DEP$_{611-628}$ peptide caused significant decreases in cell viability of UM-UC-3 bladder cancer cells in a dose-dependent manner, as measured by MTT assay (FIG. 5D; upper panel; P<0.05 at 2.0 and 3.0 micro M peptides by unpaired t-test), although its scramble peptide revealed no effect. The present inventors also observed its similar effect on another bladder cancer cell line, J82, in which DEPDC1 and ZNF224 were co-upregulated (FIG. 5F). In contrast, 11R-DEP$_{611-628}$ peptide reveled no significant effect on cell viability of normal human dermal fibroblasts (NHDF) cells (FIG. 5D; lower panel), in which DEPDC1 and ZNF224 expressions were hardly detectable (FIG. 5C).

To further clarify the mechanism of growth suppression by the 11R-DEP$_{611-628}$ peptide, the present inventors performed TUNEL assay using the cancer cells treated with this peptide (FIG. 7B). The results showed that treatment of this peptide led to significant increase in TUNEL-positive cells, compared with the treatment of the scramble peptide as well as PBS as a control (lower panel; P<0.000001, unpaired t-test). In addition, it was confirmed that 11R-DEP$_{611-628}$ peptide reveled significant increase in sub-G1 population by flow cytometric analysis (FIG. 7C), implying that 11R-DEP$_{611-628}$ peptide caused apoptotic cell death of bladder cancer cells. Taken together, these data suggest that 11R-DEP$_{611-628}$ peptide could specifically inhibit a functional complex formation of DEPDC1 and ZNF224, and led to significant growth suppression, while it showed no toxic effect on normal human cells that did not express these proteins.

9. Identification of a Gene Regulated by the DEPDC1-ZNF224 Complex.

To examine the potential promoter-specific repression of A20 transcription by the DEPDC1-ZNF224 complex, in first a promoter region of A20 gene was searched by computer prediction program, WWW Promoter Scan (www-bimas.cit.nih.gov/molbio/proscan/). Then it was co-transfected into UM-UC-3 cells with the reporter plasmid containing an approximately 300-bp fragment corresponding to a promote region of A20 gene that was fused to a luciferase reporter gene as well as either of two plasmid clones designed to express DEPDC1 or ZNF224, or both clones. In the luciferase reporter assay using the A20 reporter plasmid, NHDF cells co-transfected with both DEPDC1-HA and ZNF224-FLAG constructs showed significant reduction of luciferase reporter activity, compared with those transfected with DEPDC1 alone, ZNF224 alone, or mock plasmid (FIG. 10A).

To further investigate whether the DEPDC1-ZNF224 complex could bind to the A20 promoter region, the present inventors performed chromatin immunoprecipitation (ChIP) assay using the cell lystes extracted from HEK293 cells transfected with both DEPDC1-HA and ZNF224-FLAG constructs. The 296-bp genomic fragment (position-330 to −35) of the A20 was specifically detected a DEPDC1-ZNF224-DNA complex in immunoprecipitation (IP) products with anti-HA antibody, suggesting that ZNF224 directly bound to the A20 gene promoter region, but DEPDC1 did not (FIG. 10B). Taken together, our findings strongly suggest that DEPDC1-ZNF224 complex might function as transcriptional repressor, and repress transactivation of A20 gene in bladder cancer cells.

10. Inhibition of DEPDC1-ZNF224 Mediated-Anti-Apoptosis by 11R-DEP$_{611-628}$ Peptide.

A20 was initially identified as a cytoplasmic zinc finger protein that was rapidly induced after stimulation of tumor-necrosis factor-alpha (TNF-alpha) and functioned as a negative regulator of the NF-kappa B canonical pathway (Krikos A, Laherty C D, Dixit V M. Krikos A, Laherty C D, Dixit V M. J Biol. Chem. 1992; 267:17971-6., Beyaert R, Heyninck K, Van Huffel S, Biochem Pharmacol. 2000; 60:1143-51). Therefore, the present inventors focused on the effect of A20 in the NF-kappa B signaling pathway. Western blot analysis showed that expression of A20 was elevated 6 hours after the treatment of 11R-DEP$_{611-628}$ peptide that inhibited the DEPDC1-ZNF224 complex formation (FIG. 11A; 1st panels).

A20 was indicated to inhibit the phosphorylation of I kappa B-alpha inhibitor of NF-kappa B and subsequently block its ubiquitination and proteosomal degradation (Wertz I E, O'Rourke K M, Zhou H, et al. Nature. 2004; 430:694-9, Boone D L, Turer E E, Lee E G, et al., Nat. Immunol. 2004; 5:1052-60., Heyninck K, Beyaert R. Trends Biochem Sci. 2005; 30:1-4.). Therefore, the present inventors examined effects on the I kappa B protein level by treatment of 11R-DEP$_{611-628}$ peptide and found that I kappa B-alpha protein level was elevated at 12 hours after the treatment of 11R-DEP$_{611-628}$ peptide (FIG. 11A; second panels), while its mRNA level was unchanged (FIG. 11A, third panels). Moreover, it was confirmed that 11R-DEP$_{611-628}$ peptide clearly diminished the nuclear-staining of NF-kappa B (p65) protein (FIG. 11B; left panels, white arrows) although the treatment with the scramble peptide revealed no effect (FIG. 11B, left panels, yellow arrows; right panel, P<0.01, unpaired t-test), implying inhibition of nuclear-transport of NF-kappa B (p65) protein by 11R-DEP$_{611-628}$ peptide. Taken together, these results strongly suggest that 11R-DEP$_{611-628}$ peptide inhibited the DEPDC1-ZNF224 complex formation, activated the transcription of its downstream gene A20, and resulted in apoptosis induction through inactivation of the NF-kappa B pathway.

III. Discussion

Significant advances in development of molecular targeting drugs for cancer therapy have been achieved in the last two decades. However, the proportion of patients showing good response to presently available treatments is still very limited and a subset of the patients suffer from severe adverse reactions without any benefit (Ardavanis A, et al., Br J Cancer 2005 92:645-50). Therefore, the present invention establishes an effective screening system to identify therapeutic targets and their functionally relevant partners toward the goal of developing small molecular compounds that have more specific and efficient anticancer effect with minimum risk of adverse effects than current therapies. It had been previously reported that DEPDC1 (DEP domain containing 1) is highly and specifically transactivated in bladder cancer cells. Moreover, since DEPDC1 expression is hardly detectable in any of the examined 24 normal human tissues except testis, it has potential as a drug target (Kanehira M, et al., Oncogene 2007 26:6448-55). The DEPDC1-ZNF224 complex is likely to play a critical role in bladder carcinogenesis. DEPDC1 had previously been identified through gene expression profiles searching for genes overexpressed in bladder cancer. RT-PCR analysis detected an increased DEPDC1 expression in bladder cancers. Also, its interacting protein ZNF224 was detected as having increased expression in bladder cancers.

Further, immunocytochemical analyses revealed co-localization of DEPDC1 and ZNF224, mainly in the nucleus of bladder cancer cells (FIG. 1C). In addition, over expression of DEPDC1/ZNF224 showed growth promoting effect in bladder cancer cell line (FIG. 3B upper). Furthermore, knockdown of endogenous ZNF224 by siRNAs was shown to cause decreased growth in bladder cancer cell lines as well as a DEPDC1 knockdown effect (FIG. 2). These results suggest the significant role(s) of DEPDC1 through interaction with ZNF224 in bladder carcinogenesis.

The identified ZNF224, a member of Kruppel-like zinc finger protein, contains Kruppel-associated box (KRAB) domain at the N-terminus and 19 Cys2-His2 zinc finger domains at the C-terminus (Medugno L, Costanzo P, Lupo A, et al. FEBS Lett 2003; 534:93-100., Medugno L, Florio F, De Cegli R, et al. Gene. 2005; 359:35-43).

Accumulating evidences have indicated that a KRAB zinc-finger protein family is associated with transcriptional repression of target genes and that KRAB domain functions as a mediator of a repression system (Margolin J F, Friedman J R, Meyer W K, Vissing H, Thiesen H J, Rauscher F J 3$^{rd}$. Proc Natl Acad Sci USA 1994; 91:4509-13; Friedman J R, Fredericks W J, Jensen D E, et al. Genes Dev 1996; 10:2067-78.). ZNF224 was also reported to function as a repressor protein that specifically bound to promoter regions of its specific downstream genes and repressed their transcription (Lee, T H, Lwu S, Kim J, Pelletier J. J Biol Chem 2002; 277:44826-37.; Medugno L, Costanzo P, Lupo A, et al. FEBS Lett 2003; 534:93-100.; Medugno L, Florio F, De Cegli R, et al. Gene. 2005; 359:35-43).

The present inventors here also suggested a possibility of the DEPDC1-mediated transcriptional repression through its interaction with ZNF224. The DEPDC1-ZNF224 complex was likely to repress the transcription of A20, which was known to function as a negative regulator of the NF-kappa B signaling pathway (Krikos A, Laherty C D, Dixit V M. Krikos A, Laherty C D, Dixit V M. J Biol. Chem. 1992; 267:17971-6.; Beyaert R, Heyninck K, Van Huffel S. Biochem Pharmacol. 2000; 60:1143-51). The reporter gene assay and ChIP analysis using the possible promoter segment of the A20 gene have suggested that the DEPDC1-ZNF224 complex has the transrepressing activity through their interaction with the promoter region of A20. Interestingly, A20 has been reported to play as a negative regulator in the NF-kappa B anti-apoptotic pathway (He K L, Ting A T. Mol Cell Biol 2002; 22:6034-45.; Krikos A, Laherty C D, Dixit V M. Krikos A, Laherty C D, Dixit V M. J Biol. Chem. 1992; 267:17971-6.)

NF-kappa B is known to be a transcriptional factor that induces anti-apoptotic proteins, and is constitutively activated in various human tumors including bladder cancers (Horiguchi Y, Kuroda K, Nakashima J, Murai M, Umezawa K. Expert Rev Anticancer ther. 2003; 3:793-8.; Umezawa K. Cancer Sci 2006; 97:990-5.; Yamamoto Y, Gaynor R B. J Clin Invest 2001; 107:135-42.). Moreover, it was recently reported that dysregulation of NF-kappa B signaling caused by loss of tumor suppressive function of A20 protein is involved in the pathogenesis of a subset of B-cell lymphomas, implying that A20 has the tumor-suppressive function (Compagno M, Lim W K, Grunn A, et al. Nature. 2009; 459:717-21.; Kato M, Sanada M, Kato I, et al. Nature. 2009; 459:712-6.).

These data presented here indicate that the DEPDC1-ZNF224 complex represses the transcription of the A20 gene, and leads to transport of NF-kappaB protein into the nucleus, resulting in suppression of apoptosis of bladder cancer cells (FIG. 12; upper panel). Furthermore, the present inventors designed the cell-permeable peptides carrying the DEPDC1-derived 18-amino-acid peptide (11R-DEP$_{611-628}$ peptide) that corresponded to the binding domain to ZNF224 protein and could inhibit the functional interaction of DEPDC1 with ZNF224 (FIG. 12; lower panel). Blocking their interaction by 11R-DEP$_{611-628}$ peptide clearly resulted in induction of apoptotic cell death of bladder cancer cells.

From the clinical point of view, because intraverstical instillation therapy of Bacillus Calmette-Guerin (BCG) has become a standard treatment for carcinoma in situ (CIS) of the urinary bladder, this peptide inhibitor may also be expected to utilize for the patients with bladder. In conclusion, the present inventors successfully generated a peptide inhibitor, which specifically inhibit their complex formation and led to growth-suppressive effects.

Industrial Applicability

The present invention identifies binding between DEPDC1 and ZNF224 and demonstrate the importance of this binding to developing cancer.

In particular, agents that block the binding between the peptides appear to find therapeutic utility as anti-cancer agents, particularly anti-cancer agents for the treatment of bladder cancer.

To that end, the present invention provides polypeptides that inhibit the binding of these peptides, and identify polypeptides useful in treating or preventing cancer, such as bladder cancer. The polypeptide of the present invention are preferably composed of an amino acid sequence which contains PPNRRKLQLLMRMISRMS/SEQ ID NO: 28. The polypeptides of the present invention can be administered to inhibit the proliferation of cancer cells, such as bladder cancer.

In addition, cell growth may be suppressed by small interfering RNA (siRNA) that specifically target the ZNF224 gene. Thus, the novel siRNAs discussed herein are useful targets for the development of anti-cancer pharmaceuticals.

Bladder cancer is an important cancer for which an effective treatment method remains to be provided. Therefore, the present invention is significant in that it also provides an effective method for treating and/or preventing bladder cancer.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention.

The invention claimed is:

1. A method of screening for a candidate compound for treating a cancer associated with DEPDC1 or inhibiting the binding between DEPDC1 and ZNF224, said method comprising the steps of:
   (a) contacting a DEPDC1 polypeptide or functional equivalent thereof which comprises the amino acid sequence of SEQ ID NO: 28, 54 or 55 with a ZNF224 polypeptide, in the presence of a test compound;
   (b) detecting the binding between the polypeptides; and
   (c) selecting the test compound that inhibits the binding between these polypeptides.

2. The method of claim 1, wherein the cancer is bladder cancer.

* * * * *

SEQUENCE LISTING

```
<160> NUMBER OF SEQ ID NOS: 82

<210> SEQ ID NO 1
<211> LENGTH: 20
<212> TYPE: DNA
<213> ORGANISM: Artificial
<220> FEATURE:
<223> OTHER INFORMATION: An artificially synthesized primer for PCR

<400> SEQUENCE: 1
gagcagcatg ggaagaacat                                            20

<210> SEQ ID NO 2
<211> LENGTH: 20
<212> TYPE: DNA
<213> ORGANISM: Artificial
<220> FEATURE:
<223> OTHER INFORMATION: An artificially synthesized primer for PCR

<400> SEQUENCE: 2
tgaggcctga ctaaagcaca                                            20

<210> SEQ ID NO 3
<211> LENGTH: 20
<212> TYPE: DNA
<213> ORGANISM: Artificial
<220> FEATURE:
<223> OTHER INFORMATION: An artificially synthesized primer for PCR

<400> SEQUENCE: 3
cgaccacttt gtcaagctca                                            20

<210> SEQ ID NO 4
<211> LENGTH: 23
<212> TYPE: DNA
<213> ORGANISM: Artificial
<220> FEATURE:
```

-continued

<223> OTHER INFORMATION: An artificially synthesized primer for PCR

<400> SEQUENCE: 4
ggttgagcac agggtacttt att                    23

<210> SEQ ID NO 5
<211> LENGTH: 27
<212> TYPE: DNA
<213> ORGANISM: Artificial
<220> FEATURE:
<223> OTHER INFORMATION: An artificially synthesized primer for
      construction

<400> SEQUENCE: 5
ggaaagcggc cgcatgacca cgttcaa              27

<210> SEQ ID NO 6
<211> LENGTH: 30
<212> TYPE: DNA
<213> ORGANISM: Artificial
<220> FEATURE:
<223> OTHER INFORMATION: An artificially synthesized primer for
      construction

<400> SEQUENCE: 6
gccgctcgag aggtttttct ccaacatgaa            30

<210> SEQ ID NO 7
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 7
gaagcagcac gacttcttc                       19

<210> SEQ ID NO 8
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 8
gcgcgctttg taggattcg                       19

<210> SEQ ID NO 9
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 9
ccgatttgga tgatgaaga                       19

<210> SEQ ID NO 10
<211> LENGTH: 19
<212> TYPE: DNA
<213> ORGANISM: Artificial
<220> FEATURE:
<223> OTHER INFORMATION: An artificially synthesized target sequence for
      siRNA

```
<400> SEQUENCE: 10
ccgcaggaac acatcaaga                                                        19

<210> SEQ ID NO 11
<211> LENGTH: 20
<212> TYPE: DNA
<213> ORGANISM: Artificial
<220> FEATURE:
<223> OTHER INFORMATION: An artificially synthesized primer for PCR

<400> SEQUENCE: 11
gagcagcatg ggaagaacat                                                       20

<210> SEQ ID NO 12
<211> LENGTH: 20
<212> TYPE: DNA
<213> ORGANISM: Artificial
<220> FEATURE:
<223> OTHER INFORMATION: An artificially synthesized primer for PCR

<400> SEQUENCE: 12
tgaggcctga ctaaagcaca                                                       20

<210> SEQ ID NO 13
<211> LENGTH: 20
<212> TYPE: DNA
<213> ORGANISM: Artificial
<220> FEATURE:
<223> OTHER INFORMATION: An artificially synthesized primer for PCR

<400> SEQUENCE: 13
cgaccacttt gtcaagctca                                                       20

<210> SEQ ID NO 14
<211> LENGTH: 23
<212> TYPE: DNA
<213> ORGANISM: Artificial
<220> FEATURE:
<223> OTHER INFORMATION: An artificially synthesized primer for PCR

<400> SEQUENCE: 14
ggttgagcac agggtacttt att                                                   23

<210> SEQ ID NO 15
<211> LENGTH: 20
<212> TYPE: DNA
<213> ORGANISM: Artificial
<220> FEATURE:
<223> OTHER INFORMATION: An artificially synthesized primer for PCR

<400> SEQUENCE: 15
atggtgagag cgatgaggtc                                                       20

<210> SEQ ID NO 16
<211> LENGTH: 20
<212> TYPE: DNA
<213> ORGANISM: Artificial
<220> FEATURE:
<223> OTHER INFORMATION: An artificially synthesized primer for PCR

<400> SEQUENCE: 16
aatcgggctc gttctttctt                                                       20

<210> SEQ ID NO 17
```

```
<211> LENGTH: 20
<212> TYPE: DNA
<213> ORGANISM: Artificial
<220> FEATURE:
<223> OTHER INFORMATION: An artificially synthesized primer for PCR

<400> SEQUENCE: 17
tctctctttc tggcctggag                                              20

<210> SEQ ID NO 18
<211> LENGTH: 20
<212> TYPE: DNA
<213> ORGANISM: Artificial
<220> FEATURE:
<223> OTHER INFORMATION: An artificially synthesized primer for PCR

<400> SEQUENCE: 18
aatgtcggat ggatgaaacc                                              20

<210> SEQ ID NO 19
<211> LENGTH: 30
<212> TYPE: DNA
<213> ORGANISM: Artificial
<220> FEATURE:
<223> OTHER INFORMATION: An artificially synthesized primer for reporter

<400> SEQUENCE: 19
gatcacgcgt caccgtttga cccttctatc                                   30

<210> SEQ ID NO 20
<211> LENGTH: 30
<212> TYPE: DNA
<213> ORGANISM: Artificial
<220> FEATURE:
<223> OTHER INFORMATION: An artificially synthesized primer for reporter

<400> SEQUENCE: 20
gatcctcgag cagcagtgcc gtttccaact                                   30

<210> SEQ ID NO 21
<211> LENGTH: 33
<212> TYPE: PRT
<213> ORGANISM: Artificial
<220> FEATURE:
<223> OTHER INFORMATION: An artificially synthesised dominant negative
      peptide

<400> SEQUENCE: 21

Arg Arg Arg Arg Arg Arg Arg Arg Arg Gly Gly Gly Pro Lys
1               5                   10                  15

Arg His Gly Leu His Leu Ser Gln Glu Asn Gly Glu Lys Ile Lys His
            20                  25                  30

Glu

<210> SEQ ID NO 22
<211> LENGTH: 32
<212> TYPE: PRT
<213> ORGANISM: Artificial
<220> FEATURE:
<223> OTHER INFORMATION: An artificially synthesised dominant negative
      peptide

<400> SEQUENCE: 22

Arg Arg Arg Arg Arg Arg Arg Arg Arg Arg Gly Gly Gly Asn Gly
1               5                   10                  15
```

```
Glu Lys Ile Lys His Glu Ile Ile Asn Glu Asp Gln Glu Asn Ala Ile
            20                  25                  30
```

<210> SEQ ID NO 23
<211> LENGTH: 32
<212> TYPE: PRT
<213> ORGANISM: Artificial
<220> FEATURE:
<223> OTHER INFORMATION: An artificially synthesised dominant negative
      peptide

<400> SEQUENCE: 23

```
Arg Arg Arg Arg Arg Arg Arg Arg Arg Arg Gly Gly Gly Ala Ile
1               5                   10                  15

Asp Ala Leu Gln Leu Cys Cys Leu Leu Leu Pro Pro Pro Asn Arg Arg
            20                  25                  30
```

<210> SEQ ID NO 24
<211> LENGTH: 32
<212> TYPE: PRT
<213> ORGANISM: Artificial
<220> FEATURE:
<223> OTHER INFORMATION: An artificially synthesised dominant negative
      peptide

<400> SEQUENCE: 24

```
Arg Arg Arg Arg Arg Arg Arg Arg Arg Arg Arg Gly Gly Gly Pro Pro
1               5                   10                  15

Asn Arg Arg Lys Leu Gln Leu Leu Met Arg Met Ile Ser Arg Met Ser
            20                  25                  30
```

<210> SEQ ID NO 25
<211> LENGTH: 32
<212> TYPE: PRT
<213> ORGANISM: Artificial
<220> FEATURE:
<223> OTHER INFORMATION: An artificially synthesised dominant negative
      peptide

<400> SEQUENCE: 25

```
Arg Arg Arg Arg Arg Arg Arg Arg Arg Arg Arg Gly Gly Gly Ile Ser
1               5                   10                  15

Arg Met Ser Gln Asn Val Asp Met Pro Lys Leu His Asp Ala Met Gly
            20                  25                  30
```

<210> SEQ ID NO 26
<211> LENGTH: 32
<212> TYPE: PRT
<213> ORGANISM: Artificial
<220> FEATURE:
<223> OTHER INFORMATION: An artificially synthesised dominant negative
      peptide

<400> SEQUENCE: 26

```
Arg Arg Arg Arg Arg Arg Arg Arg Arg Arg Arg Gly Gly Gly Leu His
1               5                   10                  15

Asp Ala Met Gly Thr Arg Ser Leu Met Ile His Thr Phe Ser Arg Cys
            20                  25                  30
```

<210> SEQ ID NO 27
<211> LENGTH: 32
<212> TYPE: PRT
<213> ORGANISM: Artificial
<220> FEATURE:
<223> OTHER INFORMATION: An artificially synthesised dominant negative
      peptide

```
<400> SEQUENCE: 27

Arg Arg Arg Arg Arg Arg Arg Arg Arg Gly Gly Gly Leu Arg
1               5                   10                  15

Met Ser Arg Leu Ser Pro Asn Met Ile Met Gln Arg Pro Lys Arg Leu
            20                  25                  30

<210> SEQ ID NO 28
<211> LENGTH: 18
<212> TYPE: PRT
<213> ORGANISM: Artificial
<220> FEATURE:
<223> OTHER INFORMATION: An artificially synthesised target peptide

<400> SEQUENCE: 28

Pro Pro Asn Arg Arg Lys Leu Gln Leu Leu Met Arg Met Ile Ser Arg
1               5                   10                  15

Met Ser

<210> SEQ ID NO 29
<211> LENGTH: 9
<212> TYPE: PRT
<213> ORGANISM: Artificial
<220> FEATURE:
<223> OTHER INFORMATION: An artificially synthesised Tat sequence

<400> SEQUENCE: 29

Arg Lys Lys Arg Arg Gln Arg Arg Arg
1               5

<210> SEQ ID NO 30
<211> LENGTH: 16
<212> TYPE: PRT
<213> ORGANISM: Artificial
<220> FEATURE:
<223> OTHER INFORMATION: An artificially synthesised Penetratin sequence

<400> SEQUENCE: 30

Arg Gln Ile Lys Ile Trp Phe Gln Asn Arg Arg Met Lys Trp Lys Lys
1               5                   10                  15

<210> SEQ ID NO 31
<211> LENGTH: 21
<212> TYPE: PRT
<213> ORGANISM: Artificial
<220> FEATURE:
<223> OTHER INFORMATION: An artificially synthesised Buforin II sequence

<400> SEQUENCE: 31

Thr Arg Ser Ser Arg Ala Gly Leu Gln Phe Pro Val Gly Arg Val His
1               5                   10                  15

Arg Leu Leu Arg Lys
            20

<210> SEQ ID NO 32
<211> LENGTH: 27
<212> TYPE: PRT
<213> ORGANISM: Artificial
<220> FEATURE:
<223> OTHER INFORMATION: An artificially synthesised Transportan
      sequence

<400> SEQUENCE: 32

Gly Trp Thr Leu Asn Ser Ala Gly Tyr Leu Leu Gly Lys Ile Asn Leu
1               5                   10                  15
```

Lys Ala Leu Ala Ala Leu Ala Lys Lys Ile Leu
            20                  25

<210> SEQ ID NO 33
<211> LENGTH: 18
<212> TYPE: PRT
<213> ORGANISM: Artificial
<220> FEATURE:
<223> OTHER INFORMATION: An artificially synthesised MAP sequence

<400> SEQUENCE: 33

Lys Leu Ala Leu Lys Leu Ala Leu Lys Ala Leu Lys Ala Ala Leu Lys
1               5                   10                  15

Leu Ala

<210> SEQ ID NO 34
<211> LENGTH: 16
<212> TYPE: PRT
<213> ORGANISM: Artificial
<220> FEATURE:
<223> OTHER INFORMATION: An artificially synthesised K-FGF sequence

<400> SEQUENCE: 34

Ala Ala Val Ala Leu Leu Pro Ala Val Leu Leu Ala Leu Leu Ala Pro
1               5                   10                  15

<210> SEQ ID NO 35
<211> LENGTH: 5
<212> TYPE: PRT
<213> ORGANISM: Artificial
<220> FEATURE:
<223> OTHER INFORMATION: An artificially synthesised Ku70 sequence

<400> SEQUENCE: 35

Val Pro Met Leu Lys
1               5

<210> SEQ ID NO 36
<211> LENGTH: 5
<212> TYPE: PRT
<213> ORGANISM: Artificial
<220> FEATURE:
<223> OTHER INFORMATION: An artificially synthesised Ku70-PMLKE sequence

<400> SEQUENCE: 36

Pro Met Leu Lys Glu
1               5

<210> SEQ ID NO 37
<211> LENGTH: 28
<212> TYPE: PRT
<213> ORGANISM: Artificial
<220> FEATURE:
<223> OTHER INFORMATION: An artificially synthesised Prion sequence

<400> SEQUENCE: 37

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 38
<211> LENGTH: 18
<212> TYPE: PRT
<213> ORGANISM: Artificial

```
<220> FEATURE:
<223> OTHER INFORMATION: An artificially synthesised pVEC sequence

<400> SEQUENCE: 38

Leu Leu Ile Ile Leu Arg Arg Arg Ile Arg Lys Gln Ala His Ala His
1               5                   10                  15

Ser Lys

<210> SEQ ID NO 39
<211> LENGTH: 21
<212> TYPE: PRT
<213> ORGANISM: Artificial
<220> FEATURE:
<223> OTHER INFORMATION: An artificially synthesised Pep-1 sequence

<400> SEQUENCE: 39

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 40
<211> LENGTH: 18
<212> TYPE: PRT
<213> ORGANISM: Artificial
<220> FEATURE:
<223> OTHER INFORMATION: An artificially synthesised SynB1 sequence

<400> SEQUENCE: 40

Arg Gly Gly Arg Leu Ser Tyr Ser Arg Arg Arg Phe Ser Thr Ser Thr
1               5                   10                  15

Gly Arg

<210> SEQ ID NO 41
<211> LENGTH: 15
<212> TYPE: PRT
<213> ORGANISM: Artificial
<220> FEATURE:
<223> OTHER INFORMATION: An artificially synthesised Pep-7 sequence

<400> SEQUENCE: 41

Ser Asp Leu Trp Glu Met Met Met Val Ser Leu Ala Cys Gln Tyr
1               5                   10                  15

<210> SEQ ID NO 42
<211> LENGTH: 12
<212> TYPE: PRT
<213> ORGANISM: Artificial
<220> FEATURE:
<223> OTHER INFORMATION: An artificially synthesised HN-1 sequence

<400> SEQUENCE: 42

Thr Ser Pro Leu Asn Ile His Asn Gly Gln Lys Leu
1               5                   10

<210> SEQ ID NO 43
<211> LENGTH: 11
<212> TYPE: PRT
<213> ORGANISM: Artificial
<220> FEATURE:
<223> OTHER INFORMATION: An artificially synthesised poly-arginine-11
      sequence

<400> SEQUENCE: 43

Arg Arg Arg Arg Arg Arg Arg Arg Arg Arg Arg
```

<210> SEQ ID NO 44
<211> LENGTH: 5318
<212> TYPE: DNA
<213> ORGANISM: Homo sapiens

<400> SEQUENCE: 44

```
gagactcgcc actgccgcgg ccgctgggcc tgagtgtcgc cttcgccgcc atggacgcca      60
ccgggcgctg acagacctat ggagagtcag ggtgtgcctc ccgggcctta tcgggccacc     120
aagctgtgga atgaagttac cacatctttt cgagcaggaa tgcctctaag aaaacacaga     180
caacacttta aaaatatgg caattgtttc acagcaggag aagcagtgga ttggctttat      240
gacctattaa gaaataatag caattttggt cctgaagtta caaggcaaca gactatccaa     300
ctgttgagga aatttcttaa gaatcatgta attgaagata tcaaagggag gtggggatca     360
gaaaatgttg atgataacaa ccagctcttc agatttcctg caacttcgcc acttaaaact     420
ctaccacgaa ggtatccaga attgagaaaa acaacacatag agaactttc caaagataaa      480
gatagcattt ttaaattacg aaacttatct cgtagaactc taaaaggca tggattacat       540
ttatctcagg aaaatggcga gaaaataaag catgaaataa tcaatgaaga tcaagaaaat     600
gcaattgata tagagaact aagccaggaa gatgttgaag aagtttggag atatgttatt       660
ctgatctacc tgcaaaccat tttaggtgtg ccatccctag aagaagtcat aaatccaaaa     720
caagtaattc cccaatatat aatgtacaac atggccaata caagtaaacg tggagtagtt     780
atactacaaa acaaatcaga tgacctccct cactgggtat tatctgccat gaagtgccta     840
gcaaattggc caagaagcaa tgatatgaat aatccaactt atgttggatt tgaacgagat     900
gtattcagaa caatcgcaga ttattttcta gatctccctg aacctctact tacttttgaa     960
tattacgaat tatttgtaaa cattttggtt gtttgtggct acatcacagt ttcagataga    1020
tccagtggga tacataaaat tcaagatgat ccacagtctt caaaattcct tcacttaaac    1080
aatttgaatt ccttcaaatc aactgagtgc cttcttctca gtctgcttca tagagaaaaa    1140
aacaaagaag aatcagattc tactgagaga ctacagataa gcaatccagg atttcaagaa    1200
agatgtgcta agaaaatgca gctagttaat ttaagaaaca aagagtgag tgctaatgac    1260
ataatgggag gaagttgtca taatttaata gggttaagta tatgcatga tctatcctct    1320
aacagcaaac caaggtgctg ttcttttggaa ggaattgtag atgtgccagg gaattcaagt    1380
aaagaggcat ccagtgtctt tcatcaatct tttccgaaca tagaaggaca aaataataaa    1440
ctgttttttag agtctaagcc caaacaggaa ttcctgttga tcttcattc agaggaaaat    1500
attcaaaagc cattcagtgc tggttttaag agaacctcta ctttgactgt tcaagaccaa    1560
gaggagttgt gtaatgggaa atgcaagtca aaacagcttt gtaggtctca gagtttgctt    1620
ttaagaagta gtacaagaag gaatagttat atcaatacac cagtggctga aattatcatg    1680
aaaccaaatg ttgacaagg cagcacaagt gtgcaaacag ctatggaaag tgaactcgga    1740
gagtctagtg ccacaatcaa taaaagactc tgcaaaagta caatagaact ttcagaaaat    1800
tctttacttc cagcttcttc tatgttgact ggcacacaaa gcttgctgca acctcattta    1860
gagagggttg ccatcgatgc tctacagtta tgttgtttgt cttccccccc accaaatcgt    1920
agaaagcttc aactttttaat gcgtatgatt tcccgaatga gtcaaaatgt tgatatgccc    1980
aaacttcatg atgcaatggg tacgaggtca ctgatgatac ataccttttc tcgatgtgtg    2040
ttatgctgtg ctgaagaagt ggatcttgat gagcttcttg ctggaagatt agtttctttc    2100
```

```
ttaatggatc atcatcagga aattcttcaa gtaccctctt acttacagac tgcagtggaa    2160
aaacatcttg actacttaaa aaagggacat attgaaaatc ctggagatgg actatttgct    2220
cctttgccaa cttactcata ctgtaagcag attagtgctc aggagtttga tgagcaaaaa    2280
gtttctacct ctcaagctgc aattgcagaa cttttagaaa atattattaa aaacaggagt    2340
ttacctctaa aggagaaaag aaaaaaacta aaacagtttc agaaggaata cctttgata    2400 tatcagaaaa gatttccaac cacggagagt gaagcagcac ttttggtga caaacctaca    2460 atcaagcaac caatgctgat tttaagaaaa ccaaagttcc gtagtctaag ataactaact    2520
gaattaaaaa ttatgtaata cttgtggaac tttgataaat gaagccatat ctgagaatgt    2580
agctactcaa aaggaagtct gtcattaata aggtatttct aaataaacac attatgtaag    2640
gaagtgccaa aatagttatc aatgtgagac tcttaggaaa ctaactagat ctcaattgag    2700
agcacataac aatagatgat accaaatact ttttgttttt aacacagcta ccagtaagg    2760 ctatcatgat gtgtgctaaa atttattta cttgaatttt gaaaactgag ctgtgttagg    2820
gattaaacta taattctgtt cttaaaagaa aatttatctg caaatgtgca agttctgaga    2880
tattagctaa tgaattagtt gtttggggtt acttctttgt ttctaagtat aagaatgtga    2940
agaatatttg aaaactcaat gaaataattc tcagctgcca aatgttgcac tcttttatat    3000 attcttttc cacttttgat ctatttatat atatgtatgt gttttaaaa tatgtgtata    3060 ttttatcaga tttggttttg ccttaaatat tatccccaat tgcttcagtc attcatttgt    3120
tcagtatata tattttgaat tctagttttc ataatctatt agaagatggg gatataaaag    3180
aagtataagg caatcatata ttcattcaaa agatatttat ttagcaactg ctatgtgcct    3240
ttcgttgttc cagatatgca gagacaatga taaataaaac atataatctc ttccataagg    3300
tatttatttt ttaatcaagg gagatacacc tatcagatgt ttaaaataac aacactaccc    3360
actgaaatca gggcatatag aatcattcag ctaaagagtg acttctatga tgatggaaca    3420
ggtctctaag ctagtggttt tcaaactggt acacattaga ctcacccgag gaattttaaa    3480
acagcctata tgcccagggc ctaacttaca ctaattaaat ctgaattttg gggatgttgt    3540
atagggatta gtatttttt taatctaggt gattccaata ttcagccaac tgtgagaatc    3600
aatggcctaa atgctttta taaacatttt tataagtgtc aagataatgg cacattgact    3660 ttatttttc attggaagaa aatgcctgcc aagtataaat gactctcatc ttaaaacaag    3720
gttcttcagg tttctgcttg attgacttgg tacaaacttg aagcaagttg ccttctaatt    3780
tttactccaa gattgtttca tatctattcc ttaagtgtaa agaaatatat aatgcatggt    3840
ttgtaataaa atcttaatgt ttaatgactg ttctcatttc tcaatgtaat ttcatactgt    3900
ttctctataa aatgatagta ttccatttaa cattactgat ttttattaaa aacctggaca    3960
gaaaattata aattataaat atgactttat cctggctata aaattattga accaaaatga    4020
attcttctta aggcatttga atactaaaac gtttattgtt tatagatatg taaaatgtgg    4080
attatgttgc aaattgagat taaaattatt tggggttttg taacaatata attttgcttt    4140
tgtattatag acaaatatat aaataataaa ggcaggcaac tttcatttgc actaatgtac    4200
atgcaattga gattacaaaa tacatggtac aatgctttaa taacaaactc tgccagtcag    4260
gtttgaatcc tactgtgcta ttaactagct agtaaactca gacaagttac ttaacttctc    4320
taagccccag ttttgttatc tataaaatga atattataat agtacctctt tttaggattg    4380
cgaggattaa gcaggataat gcatgtaaag tgttagcaca gtgtctcaca tagaataagc    4440
```

```
actctataaa tattttacta gaatcaccta ggattatagc actagaagag atcttagcaa    4500
aaatgtggtc ctttctgttg ctttggacag acatgaacca aaacaaaatt acggacaatt    4560
gatgagcctt attaactatc ttttcattat gagacaaagg ttctgattat gcctactggt    4620
tgaaattttt taatctagtc aagaaggaaa atttgatgag gaaggaagga atggatatct    4680
tcagaagggc ttcgcctaag ctggaacatg gatagattcc attctaacat aaagatcttt    4740
aagttcaaat atagatgagt tgactggtag atttggtggt agttgctttc tcgggatata    4800
agaagcaaaa tcaactgcta caagtaaaga ggggatgggg aaggtgttgc acatttaaag    4860
agagaaagtg tgaaaaagcc taattgtggg aatgcacagg tttcaccaga tcagatgatg    4920
tctggttatt ctgtaaatta tagttcttat cccagaaatt actgcctcca ccatccctaa    4980
tatcttctaa ttggtatcat ataatgaccc actcttctta tgttatccaa acagttatgt    5040
ggcatttagt aatggaatgt acatggaatt tcccactgac ttacctttct gtccttggga    5100
agcttaaact ctgaatcttc tcatctgtaa aatgtgaatt aaagtatcta cctaactgag    5160
ttgtgattgt agtgaaagaa aggcaatata tttaaatctt gaatttagca agcccacgct    5220
cgatttttat gtcctttcct cttgccttgt attgagttta agatctctac tgattaaaac    5280
tcttttgcta tcaaaaaaaa aaaaaaaaaa aaaaaaaa                            5318
```

<210> SEQ ID NO 45
<211> LENGTH: 811
<212> TYPE: PRT
<213> ORGANISM: Homo sapiens

<400> SEQUENCE: 45

```
Met Glu Ser Gln Gly Val Pro Pro Gly Pro Tyr Arg Ala Thr Lys Leu
1               5                   10                  15

Trp Asn Glu Val Thr Thr Ser Phe Arg Ala Gly Met Pro Leu Arg Lys
            20                  25                  30

His Arg Gln His Phe Lys Lys Tyr Gly Asn Cys Phe Thr Ala Gly Glu
        35                  40                  45

Ala Val Asp Trp Leu Tyr Asp Leu Leu Arg Asn Asn Ser Asn Phe Gly
    50                  55                  60

Pro Glu Val Thr Arg Gln Gln Thr Ile Gln Leu Leu Arg Lys Phe Leu
65                  70                  75                  80

Lys Asn His Val Ile Glu Asp Ile Lys Gly Arg Trp Gly Ser Glu Asn
                85                  90                  95

Val Asp Asp Asn Asn Gln Leu Phe Arg Phe Pro Ala Thr Ser Pro Leu
            100                 105                 110

Lys Thr Leu Pro Arg Arg Tyr Pro Glu Leu Arg Lys Asn Asn Ile Glu
        115                 120                 125

Asn Phe Ser Lys Asp Lys Asp Ser Ile Phe Lys Leu Arg Asn Leu Ser
    130                 135                 140

Arg Arg Thr Pro Lys Arg His Gly Leu His Leu Ser Gln Glu Asn Gly
145                 150                 155                 160

Glu Lys Ile Lys His Glu Ile Ile Asn Glu Asp Gln Glu Asn Ala Ile
                165                 170                 175

Asp Asn Arg Glu Leu Ser Gln Glu Asp Val Glu Glu Val Trp Arg Tyr
            180                 185                 190

Val Ile Leu Ile Tyr Leu Gln Thr Ile Leu Gly Val Pro Ser Leu Glu
        195                 200                 205

Glu Val Ile Asn Pro Lys Gln Val Ile Pro Gln Tyr Ile Met Tyr Asn
    210                 215                 220
```

```
Met Ala Asn Thr Ser Lys Arg Gly Val Val Ile Leu Gln Asn Lys Ser
225                 230                 235                 240

Asp Asp Leu Pro His Trp Val Leu Ser Ala Met Lys Cys Leu Ala Asn
                245                 250                 255

Trp Pro Arg Ser Asn Asp Met Asn Asn Pro Thr Tyr Val Gly Phe Glu
            260                 265                 270

Arg Asp Val Phe Arg Thr Ile Ala Asp Tyr Phe Leu Asp Leu Pro Glu
        275                 280                 285

Pro Leu Leu Thr Phe Glu Tyr Tyr Glu Leu Phe Val Asn Ile Leu Val
    290                 295                 300

Val Cys Gly Tyr Ile Thr Val Ser Asp Arg Ser Ser Gly Ile His Lys
305                 310                 315                 320

Ile Gln Asp Asp Pro Gln Ser Ser Lys Phe Leu His Leu Asn Asn Leu
                325                 330                 335

Asn Ser Phe Lys Ser Thr Glu Cys Leu Leu Leu Ser Leu Leu His Arg
            340                 345                 350

Glu Lys Asn Lys Glu Glu Ser Asp Ser Thr Glu Arg Leu Gln Ile Ser
        355                 360                 365

Asn Pro Gly Phe Gln Glu Arg Cys Ala Lys Lys Met Gln Leu Val Asn
    370                 375                 380

Leu Arg Asn Arg Arg Val Ser Ala Asn Asp Ile Met Gly Gly Ser Cys
385                 390                 395                 400

His Asn Leu Ile Gly Leu Ser Asn Met His Asp Leu Ser Ser Asn Ser
                405                 410                 415

Lys Pro Arg Cys Cys Ser Leu Glu Gly Ile Val Asp Val Pro Gly Asn
            420                 425                 430

Ser Ser Lys Glu Ala Ser Ser Val Phe His Gln Ser Phe Pro Asn Ile
        435                 440                 445

Glu Gly Gln Asn Asn Lys Leu Phe Leu Glu Ser Lys Pro Lys Gln Glu
    450                 455                 460

Phe Leu Leu Asn Leu His Ser Glu Glu Asn Ile Gln Lys Pro Phe Ser
465                 470                 475                 480

Ala Gly Phe Lys Arg Thr Ser Thr Leu Thr Val Gln Asp Gln Glu Glu
                485                 490                 495

Leu Cys Asn Gly Lys Cys Lys Ser Lys Gln Leu Cys Arg Ser Gln Ser
            500                 505                 510

Leu Leu Leu Arg Ser Ser Thr Arg Arg Asn Ser Tyr Ile Asn Thr Pro
        515                 520                 525

Val Ala Glu Ile Ile Met Lys Pro Asn Val Gly Gln Gly Ser Thr Ser
    530                 535                 540

Val Gln Thr Ala Met Glu Ser Glu Leu Gly Glu Ser Ser Ala Thr Ile
545                 550                 555                 560

Asn Lys Arg Leu Cys Lys Ser Thr Ile Glu Leu Ser Glu Asn Ser Leu
                565                 570                 575

Leu Pro Ala Ser Ser Met Leu Thr Gly Thr Gln Ser Leu Leu Gln Pro
            580                 585                 590

His Leu Glu Arg Val Ala Ile Asp Ala Leu Gln Leu Cys Cys Leu Leu
        595                 600                 605

Leu Pro Pro Pro Asn Arg Arg Lys Leu Gln Leu Leu Met Arg Met Ile
    610                 615                 620

Ser Arg Met Ser Gln Asn Val Asp Met Pro Lys Leu His Asp Ala Met
625                 630                 635                 640
```

Gly Thr Arg Ser Leu Met Ile His Thr Phe Ser Arg Cys Val Leu Cys
            645                 650                 655

Cys Ala Glu Glu Val Asp Leu Asp Glu Leu Leu Ala Gly Arg Leu Val
        660                 665                 670

Ser Phe Leu Met Asp His His Gln Glu Ile Leu Gln Val Pro Ser Tyr
    675                 680                 685

Leu Gln Thr Ala Val Glu Lys His Leu Asp Tyr Leu Lys Lys Gly His
690                 695                 700

Ile Glu Asn Pro Gly Asp Gly Leu Phe Ala Pro Leu Pro Thr Tyr Ser
705                 710                 715                 720

Tyr Cys Lys Gln Ile Ser Ala Gln Glu Phe Asp Glu Gln Lys Val Ser
                725                 730                 735

Thr Ser Gln Ala Ala Ile Ala Glu Leu Leu Glu Asn Ile Ile Lys Asn
            740                 745                 750

Arg Ser Leu Pro Leu Lys Glu Lys Arg Lys Lys Leu Lys Gln Phe Gln
        755                 760                 765

Lys Glu Tyr Pro Leu Ile Tyr Gln Lys Arg Phe Pro Thr Thr Glu Ser
    770                 775                 780

Glu Ala Ala Leu Phe Gly Asp Lys Pro Thr Ile Lys Gln Pro Met Leu
785                 790                 795                 800

Ile Leu Arg Lys Pro Lys Phe Arg Ser Leu Arg
                805                 810

<210> SEQ ID NO 46
<211> LENGTH: 4466
<212> TYPE: DNA
<213> ORGANISM: Homo sapiens

<400> SEQUENCE: 46
gagactcgcc actgccgcgg ccgctgggcc tgagtgtcgc cttcgccgcc atggacgcca      60
ccgggcgctg acagacctat ggagagtcag ggtgtgcctc ccgggcctta tcgggccacc     120
aagctgtgga atgaagttac acatcttttc gagcaggaa tgcctctaag aaaacacaga     180
caacacttta aaaatatgg caattgtttc acagcaggag aagcagtgga ttggctttat     240
gacctattaa gaaataatag caattttggt cctgaagtta caaggcaaca gactatccaa     300
ctgttgagga aatttcttaa gaatcatgta attgaagata tcaaagggag gtggggatca     360
gaaaatgttg atgataacaa ccagctcttc agatttcctg caacttcgcc acttaaaact     420
ctaccacgaa ggtatccaga attgagaaaa acaacatag agacttttc caaagataaa     480 gatagcattt ttaaattacg aaacttatct cgtagaactc ctaaaaggca tggattacat     540
ttatctcagg aaaatggcga gaaaataaag catgaaataa tcaatgaaga tcaagaaaat     600
gcaattgata tagagaact aagccaggaa gatgttgaag aagtttggag atatgttatt     660
ctgatctacc tgcaaaccat tttaggtgtg ccatccctag aagaagtcat aaatccaaaa     720
caagtaattc cccaatatat aatgtacaac atggccaata caagtaaacg tggagtagtt     780
atactacaaa acaaatcaga tgacctccct cactgggtat tatctgccat gaagtgccta     840
gcaaattggc caagaagcaa tgatatgaat aatccaactt atgttggatt tgaacgagat     900
gtattcagaa caatcgcaga ttattttcta gatctccctg aacctctact tactttttgaa     960 tattacgaat tatttgtaaa cattttgggc ttgctgcaac ctcatttaga gagggttgcc    1020
atcgatgctc tacagttatg ttgttttgtta cttcccccac caaatcgtag aaagcttcaa    1080
cttttaatgc gtatgatttc ccgaatgagt caaaatgttg atatgcccaa acttcatgat    1140

-continued

```
gcaatgggta cgaggtcact gatgatacat accttttctc gatgtgtgtt atgctgtgct    1200
gaagaagtgg atcttgatga gcttcttgct ggaagattag tttctttctt aatggatcat    1260
catcaggaaa ttcttcaagt accctcttac ttacagactg cagtggaaaa acatcttgac    1320
tacttaaaaa agggacatat tgaaaatcct ggagatggac tatttgctcc tttgccaact    1380
tactcatact gtaagcagat tagtgctcag gagtttgatg agcaaaaagt ttctacctct    1440
caagctgcaa ttgcagaact tttagaaaat attattaaaa acaggagttt acctctaaag    1500
gagaaaagaa aaaactaaa acagtttcag aaggaatatc ctttgatata tcagaaaaga    1560
tttccaacca cggagagtga agcagcactt tttggtgaca aacctacaat caagcaacca    1620
atgctgattt taagaaaacc aaagttccgt agtctaagat aactaactga attaaaaatt    1680
atgtaatact tgtggaactt tgataaatga agccatatct gagaatgtag ctactcaaaa    1740
ggaagtctgt cattaataag gtatttctaa ataaacacat tatgtaagga agtgccaaaa    1800
tagttatcaa tgtgagactc ttaggaaact aactagatct caattgagag cacataacaa    1860
tagatgatac caaatacttt ttgttttaa cacagctatc cagtaaggct atcatgatgt    1920
gtgctaaaat tttatttact tgaattttga aaactgagct gtgttaggga ttaaactata    1980
attctgttct taaagaaaa tttatctgca aatgtgcaag ttctgagata ttagctaatg    2040
aattagttgt ttggggttac ttcttttgttt ctaagtataa gaatgtgaag aatatttgaa    2100
aactcaatga aataattctc agctgccaaa tgttgcactc tttatatat tcttttccca    2160 cttttgatct atttatatat atgtatgtgt ttttaaaata tgtgtatatt ttatcagatt    2220
tggttttgcc ttaaatatta tccccaattg cttcagtcat tcatttgttc agtatatata    2280
ttttgaattc tagttttcat aatctattag aagatgggga tataaaagaa gtataaggca    2340
atcatatatt cattcaaaag atatttattt agcaactgct atgtgccttt cgttgttcca    2400
gatatgcaga gacaatgata aataaaacat ataatctctt ccataaggta tttatttttt    2460
aatcaaggga gatacaccta tcagatgttt aaaataacaa cactacccac tgaaatcagg    2520
gcatatagaa tcattcagct aaagagtgac ttctatgatg atggaacagg tctctaagct    2580
agtggttttc aaactggtac acattagact cacccgagga attttaaaac agcctatatg    2640
cccagggcct aacttacact aattaaatct gaattttggg gatgttgtat agggattagt    2700 attttttta atctaggtga ttccaatatt cagccaactg tgagaatcaa tggcctaaat    2760 gcttttata aacatttta taagtgtcaa gataatggca cattgacttt atttttttcat    2820 tggaagaaaa tgcctgccaa gtataaatga ctctcatctt aaaacaaggt tcttcaggtt    2880
tctgcttgat tgacttggta caaacttgaa gcaagttgcc ttctaatttt tactccaaga    2940
ttgtttcata tctattcctt aagtgtaaag aaatatataa tgcatggttt gtaataaaat    3000
cttaatgttt aatgactgtt ctcatttctc aatgtaattt catactgttt ctctataaaa    3060
tgatagtatt ccatttaaca ttactgattt ttattaaaaa cctggacaga aaattataaa    3120
ttataaatat gactttatcc tggctataaa attattgaac caaaatgaat tctttctaag    3180
gcatttgaat actaaaacgt ttattgttta tagatatgta aatgtggat tatgttgcaa    3240 attgagatta aaattatttg ggttttgta acaatataat tttgcttttg tattatagac    3300
aaatatataa ataataaagg caggcaactt tcatttgcac taatgtacat gcaattgaga    3360
ttacaaaata catggtacaa tgctttaata acaaactctg ccagtcaggt ttgaatccta    3420
ctgtgctatt aactagctag taaactcaga caagttactt aacttctcta agccccagtt    3480
ttgttatcta taaatgaat attataatag taccttcttt taggattgcg aggattaagc    3540
```

-continued

```
aggataatgc atgtaaagtg ttagcacagt gtctcacata gaataagcac tctataaata    3600
ttttactaga atcacctagg attatagcac tagaagagat cttagcaaaa atgtggtcct    3660
ttctgttgct ttggacagac atgaaccaaa acaaaattac ggacaattga tgagccttat    3720
taactatctt ttcattatga gacaaaggtt ctgattatgc ctactggttg aaatttttta    3780
atctagtcaa gaaggaaaat ttgatgagga aggaaggaat ggatatcttc agaagggctt    3840
cgcctaagct ggaacatgga tagattccat tctaacataa agatctttaa gttcaaatat    3900
agatgagttg actggtagat ttggtggtag ttgctttctc gggatataag aagcaaaatc    3960
aactgctaca agtaaagagg ggatgggaa ggtgttgcac atttaaagag agaaagtgtg    4020
aaaaagccta attgtgggaa tgcacaggtt tcaccagatc agatgatgtc tggttattct    4080
gtaaattata gttcttatcc cagaaattac tgcctccacc atccctaata tcttctaatt    4140
ggtatcatat aatgacccac tcttcttatg ttatccaaac agttatgtgg catttagtaa    4200
tggaatgtac atggaatttc ccactgactt acctttctgt ccttgggaag cttaaactct    4260
gaatcttctc atctgtaaaa tgtgaattaa agtatctacc taactgagtt gtgattgtag    4320
tgaaagaaag gcaatatatt taaatcttga atttagcaag cccacgctcg attttatgt    4380 cctttcctct tgccttgtat tgagtttaag atctctactg attaaaactc ttttgctatc    4440
aaaaaaaaaa aaaaaaaaaa aaaaaa                                         4466
```

<210> SEQ ID NO 47
<211> LENGTH: 527
<212> TYPE: PRT
<213> ORGANISM: Homo sapiens

<400> SEQUENCE: 47

```
Met Glu Ser Gln Gly Val Pro Pro Gly Pro Tyr Arg Ala Thr Lys Leu
1               5                   10                  15

Trp Asn Glu Val Thr Thr Ser Phe Arg Ala Gly Met Pro Leu Arg Lys
            20                  25                  30

His Arg Gln His Phe Lys Lys Tyr Gly Asn Cys Phe Thr Ala Gly Glu
        35                  40                  45

Ala Val Asp Trp Leu Tyr Asp Leu Leu Arg Asn Asn Ser Asn Phe Gly
    50                  55                  60

Pro Glu Val Thr Arg Gln Gln Thr Ile Gln Leu Leu Arg Lys Phe Leu
65                  70                  75                  80

Lys Asn His Val Ile Glu Asp Ile Lys Gly Arg Trp Gly Ser Glu Asn
                85                  90                  95

Val Asp Asp Asn Asn Gln Leu Phe Arg Phe Pro Ala Thr Ser Pro Leu
            100                 105                 110

Lys Thr Leu Pro Arg Arg Tyr Pro Glu Leu Arg Lys Asn Asn Ile Glu
        115                 120                 125

Asn Phe Ser Lys Asp Lys Asp Ser Ile Phe Lys Leu Arg Asn Leu Ser
    130                 135                 140

Arg Arg Thr Pro Lys Arg His Gly Leu His Leu Ser Gln Glu Asn Gly
145                 150                 155                 160

Glu Lys Ile Lys His Glu Ile Ile Asn Glu Asp Gln Glu Asn Ala Ile
                165                 170                 175

Asp Asn Arg Glu Leu Ser Gln Glu Asp Val Glu Glu Val Trp Arg Tyr
            180                 185                 190

Val Ile Leu Ile Tyr Leu Gln Thr Ile Leu Gly Val Pro Ser Leu Glu
        195                 200                 205
```

Glu Val Ile Asn Pro Lys Gln Val Ile Pro Gln Tyr Ile Met Tyr Asn
    210                 215                 220

Met Ala Asn Thr Ser Lys Arg Gly Val Ile Leu Gln Asn Lys Ser
225                 230                 235                 240

Asp Asp Leu Pro His Trp Val Leu Ser Ala Met Lys Cys Leu Ala Asn
                245                 250                 255

Trp Pro Arg Ser Asn Asp Met Asn Asn Pro Thr Tyr Val Gly Phe Glu
                260                 265                 270

Arg Asp Val Phe Arg Thr Ile Ala Asp Tyr Phe Leu Asp Leu Pro Glu
                275                 280                 285

Pro Leu Leu Thr Phe Glu Tyr Tyr Glu Leu Phe Val Asn Ile Leu Gly
    290                 295                 300

Leu Leu Gln Pro His Leu Glu Arg Val Ala Ile Asp Ala Leu Gln Leu
305                 310                 315                 320

Cys Cys Leu Leu Leu Pro Pro Asn Arg Arg Lys Leu Gln Leu Leu
                325                 330                 335

Met Arg Met Ile Ser Arg Met Ser Gln Asn Val Asp Met Pro Lys Leu
                340                 345                 350

His Asp Ala Met Gly Thr Arg Ser Leu Met Ile His Thr Phe Ser Arg
    355                 360                 365

Cys Val Leu Cys Cys Ala Glu Glu Val Asp Leu Asp Glu Leu Leu Ala
370                 375                 380

Gly Arg Leu Val Ser Phe Leu Met Asp His His Gln Glu Ile Leu Gln
385                 390                 395                 400

Val Pro Ser Tyr Leu Gln Thr Ala Val Glu Lys His Leu Asp Tyr Leu
                405                 410                 415

Lys Lys Gly His Ile Glu Asn Pro Gly Asp Gly Leu Phe Ala Pro Leu
                420                 425                 430

Pro Thr Tyr Ser Tyr Cys Lys Gln Ile Ser Ala Gln Glu Phe Asp Glu
                435                 440                 445

Gln Lys Val Ser Thr Ser Gln Ala Ala Ile Ala Glu Leu Leu Glu Asn
    450                 455                 460

Ile Ile Lys Asn Arg Ser Leu Pro Leu Lys Glu Lys Arg Lys Lys Leu
465                 470                 475                 480

Lys Gln Phe Gln Lys Glu Tyr Pro Leu Ile Tyr Gln Lys Arg Phe Pro
                485                 490                 495

Thr Thr Glu Ser Glu Ala Ala Leu Phe Gly Asp Lys Pro Thr Ile Lys
                500                 505                 510

Gln Pro Met Leu Ile Leu Arg Lys Pro Lys Phe Arg Ser Leu Arg
    515                 520                 525

<210> SEQ ID NO 48
<211> LENGTH: 2466
<212> TYPE: DNA
<213> ORGANISM: Homo sapiens

<400> SEQUENCE: 48

```
gagtccaaac attcggtgga gtcgcggaca cttccgctcg gggactgagg ttgctgcagt      60
ttttccgcga tagtttgggg cagttccgcg cgttgcaggc ccttctgaat ttcctggacc     120
tacgcattgg atcctcaaag aactgctgaa taccactaga acatacctg taaccagaga     180 cagctgatta tagctttctg cagcaaggaa gcccacgtac cagggggctgt cttggcacaa     240 ttctgctttc ccaggaactg catcactcag gactctgcaa gtttccagaa gtaagaggga     300
```

```
aaatgaccac gttcaaggag gcaatgacct tcaaggacgt ggctgtggtc ttcactgagg    360
aagagctggg gctgctggac cttgctcaga ggaagctgta tcgagatgtg atgctggaga    420
acttcaggaa cctgctctca gtgggacatc aagcattcca cagggatact ttccacttcc    480
taagggaaga aaagatttgg atgatgaaga cagcaatcca aagggaaggg aattcaggag    540
acaagatcca aactgagatg gagactgttt cagaagcagg aacacatcaa gagtggtcct    600
tccagcaaat ctgggaaaaa attgcaagtg atttaaccag gtctcaagac ttggtgataa    660
atagctctca gttctccaaa gaaggtgatt tcccctgcca gactgaggca ggactatctg    720
taattcacac aagacagaaa tcttcccagg gcaatggata taaaccatcc ttcagtgatg    780
tctcccactt tgattttcat caacaattac actcaggaga gaaatctcat acgtgtgatg    840
agtgtggaaa aacttttgt tacatctcag cccttcgtat tcatcagaga gtccacatgg    900
gagagaaatg ctataagtgt gacgtgtgtg gtaaggaatt cagtcagagt tcacatctgc    960
aaactcatca gagagtccac actggagaga accgttcaa atgtgtggaa tgtgggaaag   1020
gcttcagtcg tagatcagca cttaatgttc atcacaaatt acacacagga gagaaacctt   1080
ataattgtga ggaatgcggg aaggccttca ttcacgattc ccagcttcaa gaacatcaga   1140
gaatccatac gggggagaag ccattcaaat gtgatatatg tggtaagagc ttctgtggta   1200
gatcaagact aataggcat tccatggttc acacggcaga gaaaccattc gatgtgata   1260
cgtgtgataa gagctttcgt cagagatcag cacttaatag tcatcgcatg atccacacag   1320
gagagaaacc atacaaatgt gaggagtgtg gaaaaggctt tatttgtagg cgagatcttt   1380
atacgcatca tatggtccac acgggagaaa agccatataa ttgtaaagag tgtgggaaga   1440
gcttcagatg ggcctcgtgt cttttgaaac atcagcgagt ccacagtgga gaaaaaccat   1500
tcaaatgtga agaatgtggg aaggattttt acacaaattc acaatgctat tcccaccaga   1560
gatcccatag tggagaaaaa ccatacaaat gtgtggagtg tgggaagggc tacaaaagga   1620
ggttggatct tgacttttcac cagcgcgtcc atacaggaga gaaactgtat aattgtaagg   1680
aatgtgggaa gagctttagt cgggccccat gtcttttgaa acatgagaga ctccacagtg   1740
gagaaaaacc attccaatgt gaagagtgtg gaagagatt tactcaaaat tcacatcttc   1800
attcccatca gagagttcac actggagaaa agccatacaa atgtgagaag tgtggaaagg   1860
gctacaatag taagtttaat cttgatatgc accagaaggt ccacacagga gagagaccat   1920
acaattgtaa ggaatgtggg aagagttttg gctgggcctc gtgtcttttg aaacatcaga   1980
gactgcgcag tggggaaaaa cctttcaaat gtgaagagtg tgggaaaaga tttactcaga   2040
attcacagct tcattctcat caaagagtgc acactggaga aaagccatac aaatgtgatg   2100
agtgtgggaa gggcttcagc tggtcctcaa ctcgtctgac ccatcagaga cgccacagca   2160
gagaaacacc tctcaaatgt gagcagcatg gaagaacat tgtacagaat tcattctcta   2220
aagtgcaaga aaaagttcac agtgtagaaa agccatacaa atgtgaggac tgtgggaagg   2280
gctacaacag gcgcttgaat cttgatatgc atcagagggt ccacatggga gagaaaacat   2340
ggaagtgtag ggagtgtgat atgtgcttta gtcaggcctc aagccttcga cttcatcaga   2400
atgttcatgt tggagaaaaa ccttagtgat gtgatggtgc aataaagtct tcactcagtc   2460
ttcatg                                                             2466
```

<210> SEQ ID NO 49
<211> LENGTH: 707
<212> TYPE: PRT
<213> ORGANISM: Homo sapiens

<400> SEQUENCE: 49

```
Met Thr Thr Phe Lys Glu Ala Met Thr Phe Lys Asp Val Ala Val Val
1               5                   10                  15

Phe Thr Glu Glu Glu Leu Gly Leu Leu Asp Leu Ala Gln Arg Lys Leu
                20                  25                  30

Tyr Arg Asp Val Met Leu Glu Asn Phe Arg Asn Leu Leu Ser Val Gly
            35                  40                  45

His Gln Ala Phe His Arg Asp Thr Phe His Phe Leu Arg Glu Glu Lys
        50                  55                  60

Ile Trp Met Met Lys Thr Ala Ile Gln Arg Glu Gly Asn Ser Gly Asp
65                  70                  75                  80

Lys Ile Gln Thr Glu Met Glu Thr Val Ser Glu Ala Gly Thr His Gln
                85                  90                  95

Glu Trp Ser Phe Gln Gln Ile Trp Glu Lys Ile Ala Ser Asp Leu Thr
            100                 105                 110

Arg Ser Gln Asp Leu Val Ile Asn Ser Ser Gln Phe Ser Lys Glu Gly
        115                 120                 125

Asp Phe Pro Cys Gln Thr Glu Ala Gly Leu Ser Val Ile His Thr Arg
130                 135                 140

Gln Lys Ser Ser Gln Gly Asn Gly Tyr Lys Pro Ser Phe Ser Asp Val
145                 150                 155                 160

Ser His Phe Asp Phe His Gln Gln Leu His Ser Gly Glu Lys Ser His
                165                 170                 175

Thr Cys Asp Glu Cys Gly Lys Asn Phe Cys Tyr Ile Ser Ala Leu Arg
            180                 185                 190

Ile His Gln Arg Val His Met Gly Glu Lys Cys Tyr Lys Cys Asp Val
        195                 200                 205

Cys Gly Lys Glu Phe Ser Gln Ser Ser His Leu Gln Thr His Gln Arg
210                 215                 220

Val His Thr Gly Glu Lys Pro Phe Lys Cys Val Glu Cys Gly Lys Gly
225                 230                 235                 240

Phe Ser Arg Arg Ser Ala Leu Asn Val His His Lys Leu His Thr Gly
                245                 250                 255

Glu Lys Pro Tyr Asn Cys Glu Glu Cys Gly Lys Ala Phe Ile His Asp
            260                 265                 270

Ser Gln Leu Gln Glu His Gln Arg Ile His Thr Gly Glu Lys Pro Phe
        275                 280                 285

Lys Cys Asp Ile Cys Gly Lys Ser Phe Cys Gly Arg Ser Arg Leu Asn
290                 295                 300

Arg His Ser Met Val His Thr Ala Glu Lys Pro Phe Arg Cys Asp Thr
305                 310                 315                 320

Cys Asp Lys Ser Phe Arg Gln Arg Ser Ala Leu Asn Ser His Arg Met
                325                 330                 335

Ile His Thr Gly Glu Lys Pro Tyr Lys Cys Glu Cys Gly Lys Gly
            340                 345                 350

Phe Ile Cys Arg Arg Asp Leu Tyr Thr His Met Val His Thr Gly
        355                 360                 365

Glu Lys Pro Tyr Asn Cys Lys Glu Cys Gly Lys Ser Phe Arg Trp Ala
370                 375                 380

Ser Cys Leu Leu Lys His Gln Arg Val His Ser Gly Glu Lys Pro Phe
385                 390                 395                 400

Lys Cys Glu Glu Cys Gly Lys Gly Phe Tyr Thr Asn Ser Gln Cys Tyr
```

```
                405                 410                 415
Ser His Gln Arg Ser His Ser Gly Glu Lys Pro Tyr Lys Cys Val Glu
            420                 425                 430

Cys Gly Lys Gly Tyr Lys Arg Arg Leu Asp Leu Asp Phe His Gln Arg
        435                 440                 445

Val His Thr Gly Glu Lys Leu Tyr Asn Cys Lys Cys Gly Lys Ser
    450                 455                 460

Phe Ser Arg Ala Pro Cys Leu Leu Lys His Glu Arg Leu His Ser Gly
465                 470                 475                 480

Glu Lys Pro Phe Gln Cys Glu Glu Cys Gly Lys Arg Phe Thr Gln Asn
            485                 490                 495

Ser His Leu His Ser His Gln Arg Val His Thr Gly Glu Lys Pro Tyr
        500                 505                 510

Lys Cys Glu Lys Cys Gly Lys Gly Tyr Asn Ser Lys Phe Asn Leu Asp
    515                 520                 525

Met His Gln Lys Val His Thr Gly Glu Arg Pro Tyr Asn Cys Lys Glu
    530                 535                 540

Cys Gly Lys Ser Phe Gly Trp Ala Ser Cys Leu Leu Lys His Gln Arg
545                 550                 555                 560

Leu Arg Ser Gly Glu Lys Pro Phe Lys Cys Glu Glu Cys Gly Lys Arg
            565                 570                 575

Phe Thr Gln Asn Ser Gln Leu His Ser His Gln Arg Val His Thr Gly
        580                 585                 590

Glu Lys Pro Tyr Lys Cys Asp Glu Cys Gly Lys Gly Phe Ser Trp Ser
            595                 600                 605

Ser Thr Arg Leu Thr His Gln Arg Arg His Ser Arg Glu Thr Pro Leu
    610                 615                 620

Lys Cys Glu Gln His Gly Lys Asn Ile Val Gln Asn Ser Phe Ser Lys
625                 630                 635                 640

Val Gln Glu Lys Val His Ser Val Glu Lys Pro Tyr Lys Cys Glu Asp
            645                 650                 655

Cys Gly Lys Gly Tyr Asn Arg Arg Leu Asn Leu Asp Met His Gln Arg
            660                 665                 670

Val His Met Gly Glu Lys Thr Trp Lys Cys Arg Glu Cys Asp Met Cys
    675                 680                 685

Phe Ser Gln Ala Ser Ser Leu Arg Leu His Gln Asn Val His Val Gly
        690                 695                 700

Glu Lys Pro
705

<210> SEQ ID NO 50
<211> LENGTH: 4968
<212> TYPE: DNA
<213> ORGANISM: Homo sapiens

<400> SEQUENCE: 50
gttggaaacg gcactgctga gtgaggttga ggggtgtctc ggtatgtgcg ccttggatct      60
ggtgtaggcg aggtcacgcc tctcttcaga cagcccgagc cttcccggcc tgcgcgtttt     120
agttcggaac tgcgggacgc gccggtgggc tagggcaagg tgtgtgccct cttcctgatt     180
ctggagaaaa atgccggtcc ggaagcaaga tacccagaga gcattgcacc ttttggagga     240
atatcgttca aaactaagcc aaactgaaga cagacagctc agaagttcca tagaacgggt     300
tattaacata tttcagagca acctctttca ggctttaata gatattcaag aattttatga     360
```

```
agtgacctta ctggataatc caaaatgtat agatcgttca aagccgtctg aaccaattca    420
acctgtgaat acttgggaga tttccagcct tccaagctct actgtgactt cagagacact    480
gccaagcagc cttagcccta gtgtagagaa atacaggtat caggatgaag atacacctcc    540
tcaagagcat atttccccac aaatcacaaa tgaagtgata ggtccagaat tggttcatgt    600
ctcagagaag aacttatcag agattgagaa tgtccatgga tttgtttctc attctcatat    660
ttcaccaata aagccaacag aagctgttct tccctctcct cccactgtcc ctgtgatccc    720
tgtcctgcca gtccctgctg agaatactgt catcctaccc accataccac aggcaaatcc    780
tcccccagta ctggtcaaca cagatagctt ggaaacacca acttacgtta atggcacaga    840
tgcagattat gaatatgaag aaatcacact tgaaggggga aattcagggc ttggtttcag    900
cattgcagga ggtacggaca acccacacat tggagatgac tcaagtattt tcattaccaa    960
aattatcaca gggggagcag ccgcccaaga tggaagattg cgggtcaatg actgtatatt   1020
acgagtaaat gaagtagatg ttcgtgatgt aacacatagc aaagcagttg aagcgttgaa   1080
agaagcaggg tctattgtac gcttgtatgt aaaaagaagg aaaccagtgt cagaaaaaat   1140
aatggaaata aagctcatta aaggtcctaa aggtcttggg tttagcattg ctggaggtgt   1200
tggaaatcag catattcctg gggataatag catctatgta accaaaataa ttgaaggagg   1260
tgcagcacat aaggatggca aacttcagat tggagataaa cttttagcag tgaataacgt   1320
atgtttagaa gaagttactc atgaagaagc agtaactgcc ttaaagaaca catctgattt   1380
tgtttatttg aaagtggcaa aacccacaag tatgtatatg aatgatggct atgcaccacc   1440
tgatatcacc aactcttctt ctcagcctgt tgataaccat gttagcccat cttccttctt   1500
gggccagaca ccagcatctc cagccagata ctccccagtt tctaaagcag tacttggaga   1560
tgatgaaatt acaagggaac ctagaaaagt tgttcttcat cgtggctcaa cgggccttgg   1620
tttcaacatt gtaggaggag aagatggaga aggaatattt atttccttta tcttagccgg   1680
aggacctgct gatctaagtg gagagctcag aaaaggagat cgtattatat cggtaaacag   1740
tgttgacctc agagctgcta gtcatgagca ggcagcagct gcattgaaaa atgctggcca   1800
ggctgtcaca attgttgcac aatatcgacc tgaagaatac agtcgttttg aagctaaaat   1860
acatgattta cgggagcaga tgatgaatag tagtattagt tcagggtcag gttctcttcg   1920
aactagccag aagcgatccc tctatgtcag agccctttt gattatgaca agactaaaga   1980
cagtgggctt cccagtcagg gactgaactt caaatttgga gatatcctcc atgttattaa   2040
tgcttctgat gatgaatggt ggcaagccag gcaggttaca ccagatggtg agagcgatga   2100
ggtcggagtg attcccagta aacgcagagt tgagaagaaa gaacgagccc gattaaaaac   2160
agtgaaattc aattctaaaa cgagagataa aggggagatc cctgacgaca tgggatcaaa   2220
aggcctgaag catgtaactt ctaatgccag cgatagtgaa agtagttacc gtggtcaaga   2280
agaatacgtc ttatcttatg aaccagtgaa tcaacaagaa gttaattata ctcgaccagt   2340
gatcatattg ggacctatga agacaggat aaatgatgac ttgatctcag aatttcctga   2400
caaatttgga tcctgtgttc ctcatacaac tagaccaaaa cgagattatg aggtagatgg   2460
aagagattat catttgtga cttcaagaga gcagatggaa aaagatatcc aggaacataa   2520
attcattgaa gctggccagt ataacaatca tctatatgga acaagtgttc agtctgtacg   2580
agaagtagca gaaaagggca aacactgtat ccttgatgtg tctggaaatg ccataaagag   2640
attacagatt gcacagcttt accctatctc cattttatt aaacccaaat ccatggaaaa   2700
tatcatggaa atgaataagc gtctaacaga agaacaagcc agaaaaacat ttgagagagc   2760
```

```
catgaaactg gaacaggagt ttactgaaca tttcacagct attgtacagg gggatacgct    2820
ggaagacatt tacaaccaag tgaaacagat catagaagaa caatctggtt cttacatctg    2880
ggttccggca aaagaaaagc tatgaaaact catgtttctc tgtttctctt ttccacaatt    2940
ccattttctt tggcatctct ttgccctttc ctctggagtc tttcttgagt actgatttca    3000
tgttgaattg tatcccacac atcatggtct gcagcttctt tttcacatgt agtgtctcct    3060
tcaagttaca tcgtgtgtat tatttaatgt cactattggt tagtggccat ttttcagaac    3120
tgaagatgga atggcctgac cagctattaa gaacgtgggg agacgcagaa attgtggtaa    3180
aattccttaa tgtttaaggg aaagtaactt taagagattt ttggaaaagc tttatataca    3240
ttcttttcaa atttcagtac aaatgaaaaa gtggttttaa tcagtgattt agtagacttt    3300
gagcaactgt gcacgcttca gtttaatagc atggtttggc cagtgtatta ctctcaagtc    3360
cttttctcaa tcaacttcta tcatcaaagc aattgtttca ttatagataa ataaggacat    3420
tttttaattt aaaaattcat gtctgagttg actttcataa gggatttcat ttttttcctca   3480
acattcttaa agccttttag tatttgacgg ttctttttc ccaggacatt tgctaggaat     3540
aacaacgttt caatgttttt aatctacttg agcaacacta tcgtgtctta caaaagttgt    3600
tcatatgtaa atgatcatca catttcgtga attgaggcca tgttcaggtg ctaaggaagt    3660
tcgcctttta cacagaagat tgagaaaatt tcctagatat aaatacagat aaatcagacg    3720
ttacagtggt gacgtagtaa ccatcatggc aatggaaagg agtccaattc atagcctaaa    3780
acttcaaatg tattcttagg agtcagattt tactgaatat tttacccaca atagctgcct    3840
attttgttat aataaaatat ataaatat atatataaaa ctttctttaa actgtaacta      3900
tgggaattat tttctttaca tagttgcgca cacacacaaa catatatata tatttaaaat    3960
atattttgtt tcttttgcca cctactccta acttttttgtt tggttttttaa attaaatatt  4020
aattgaatag acttatcttc cttaatcatg tgaactgaaa atgggggcat ggtggtcatg    4080
aggaggaaac atttagggaa attagattat aagtaaaagt gtgggcatat tctcctcttt    4140
tctacaaagg ttttcaaatg gttcctgagg tttttttgttg ttgtccgtgt tgttactgtt   4200
gttcttgtca tcaggtttga ttttggtcct tgcccttttcc ttctagttct ccttttatta   4260
ataggaaggc aggcaaaagc cccatttatg tgtgtgtttt cccctcagac agctttcatc    4320
cactgctctg cactagaatt gcacaaatct tcatggtgag caattttaag aaatgttagt    4380
gaaaggtaga aattatttca caaatcagtt tctctggtcc ttcatattaa taataatatt   4440
tggcttccca ttgctctttg gagttgttta ttaaatatgt gttttttgaca acctcctcat   4500
tagtttctta aatgagtact ggtttgtaaa gaattatcaa cattatccat tccatttatg    4560
aagaagagga gaacagctaa taaactgtat tgtaaaatcc atatgttaag tgtgtcttga    4620
attttgaaag aaaaaatata ttttgcaagc taacattttc ttgaaacaat ttgaggcatc    4680
atgtaactta taaccgaatc caagagccgt taggcagcag agtgtgttac cacattgaaa    4740
tacacagtgc tgctgttaga ctaaatgtcg taggttgtta accacataga aacacactag    4800
tatgaagaaa actgttgtaa aatctcaaga gcttcagaaa ctgccttaca agaccgcagc    4860
ataagctatt ttgaagtatt taccaaatag tcacatgttg taaaatatca agtggttata    4920
aaaggatgcc atttatatat taaaatttac ataacattgt tttctctgga               4968
```

<210> SEQ ID NO 51
<211> LENGTH: 904
<212> TYPE: PRT

<213> ORGANISM: Homo sapiens

<400> SEQUENCE: 51

Met Pro Val Arg Lys Gln Asp Thr Gln Arg Ala Leu His Leu Leu Glu
1               5                   10                  15

Glu Tyr Arg Ser Lys Leu Ser Gln Thr Glu Asp Arg Gln Leu Arg Ser
            20                  25                  30

Ser Ile Glu Arg Val Ile Asn Ile Phe Gln Ser Asn Leu Phe Gln Ala
        35                  40                  45

Leu Ile Asp Ile Gln Glu Phe Tyr Glu Val Thr Leu Leu Asp Asn Pro
    50                  55                  60

Lys Cys Ile Asp Arg Ser Lys Pro Ser Glu Pro Ile Gln Pro Val Asn
65                  70                  75                  80

Thr Trp Glu Ile Ser Ser Leu Pro Ser Ser Thr Val Thr Ser Glu Thr
                85                  90                  95

Leu Pro Ser Ser Leu Ser Pro Ser Val Glu Lys Tyr Arg Tyr Gln Asp
            100                 105                 110

Glu Asp Thr Pro Pro Gln Glu His Ile Ser Pro Gln Ile Thr Asn Glu
        115                 120                 125

Val Ile Gly Pro Glu Leu Val His Val Ser Glu Lys Asn Leu Ser Glu
    130                 135                 140

Ile Glu Asn Val His Gly Phe Val Ser His Ser His Ile Ser Pro Ile
145                 150                 155                 160

Lys Pro Thr Glu Ala Val Leu Pro Ser Pro Thr Val Pro Val Ile
                165                 170                 175

Pro Val Leu Pro Val Pro Ala Glu Asn Thr Val Ile Leu Pro Thr Ile
            180                 185                 190

Pro Gln Ala Asn Pro Pro Val Leu Val Asn Thr Asp Ser Leu Glu
        195                 200                 205

Thr Pro Thr Tyr Val Asn Gly Thr Asp Ala Asp Tyr Glu Tyr Glu Glu
    210                 215                 220

Ile Thr Leu Glu Arg Gly Asn Ser Gly Leu Gly Phe Ser Ile Ala Gly
225                 230                 235                 240

Gly Thr Asp Asn Pro His Ile Gly Asp Asp Ser Ser Ile Phe Ile Thr
                245                 250                 255

Lys Ile Ile Thr Gly Gly Ala Ala Gln Asp Gly Arg Leu Arg Val
            260                 265                 270

Asn Asp Cys Ile Leu Arg Val Asn Glu Val Asp Val Arg Asp Val Thr
        275                 280                 285

His Ser Lys Ala Val Glu Ala Leu Lys Glu Ala Gly Ser Ile Val Arg
    290                 295                 300

Leu Tyr Val Lys Arg Arg Lys Pro Val Ser Glu Lys Ile Met Glu Ile
305                 310                 315                 320

Lys Leu Ile Lys Gly Pro Lys Gly Leu Gly Phe Ser Ile Ala Gly Gly
                325                 330                 335

Val Gly Asn Gln His Ile Pro Gly Asp Asn Ser Ile Tyr Val Thr Lys
            340                 345                 350

Ile Ile Glu Gly Gly Ala Ala His Lys Asp Gly Lys Leu Gln Ile Gly
        355                 360                 365

Asp Lys Leu Leu Ala Val Asn Asn Val Cys Leu Glu Glu Val Thr His
    370                 375                 380

Glu Glu Ala Val Thr Ala Leu Lys Asn Thr Ser Asp Phe Val Tyr Leu
385                 390                 395                 400

-continued

```
Lys Val Ala Lys Pro Thr Ser Met Tyr Met Asn Asp Gly Tyr Ala Pro
                405                 410                 415

Pro Asp Ile Thr Asn Ser Ser Ser Gln Pro Val Asp Asn His Val Ser
            420                 425                 430

Pro Ser Ser Phe Leu Gly Gln Thr Pro Ala Ser Pro Ala Arg Tyr Ser
        435                 440                 445

Pro Val Ser Lys Ala Val Leu Gly Asp Asp Glu Ile Thr Arg Glu Pro
    450                 455                 460

Arg Lys Val Val Leu His Arg Gly Ser Thr Gly Leu Gly Phe Asn Ile
465                 470                 475                 480

Val Gly Gly Glu Asp Gly Glu Gly Ile Phe Ile Ser Phe Ile Leu Ala
                485                 490                 495

Gly Gly Pro Ala Asp Leu Ser Gly Glu Leu Arg Lys Gly Asp Arg Ile
            500                 505                 510

Ile Ser Val Asn Ser Val Asp Leu Arg Ala Ala Ser His Glu Gln Ala
        515                 520                 525

Ala Ala Ala Leu Lys Asn Ala Gly Gln Ala Val Thr Ile Val Ala Gln
    530                 535                 540

Tyr Arg Pro Glu Glu Tyr Ser Arg Phe Glu Ala Lys Ile His Asp Leu
545                 550                 555                 560

Arg Glu Gln Met Met Asn Ser Ser Ile Ser Ser Gly Ser Gly Ser Leu
                565                 570                 575

Arg Thr Ser Gln Lys Arg Ser Leu Tyr Val Arg Ala Leu Phe Asp Tyr
            580                 585                 590

Asp Lys Thr Lys Asp Ser Gly Leu Pro Ser Gln Gly Leu Asn Phe Lys
        595                 600                 605

Phe Gly Asp Ile Leu His Val Ile Asn Ala Ser Asp Asp Glu Trp Trp
    610                 615                 620

Gln Ala Arg Gln Val Thr Pro Asp Gly Glu Ser Asp Glu Val Gly Val
625                 630                 635                 640

Ile Pro Ser Lys Arg Arg Val Glu Lys Lys Glu Arg Ala Arg Leu Lys
                645                 650                 655

Thr Val Lys Phe Asn Ser Lys Thr Arg Asp Lys Gly Glu Ile Pro Asp
            660                 665                 670

Asp Met Gly Ser Lys Gly Leu Lys His Val Thr Ser Asn Ala Ser Asp
        675                 680                 685

Ser Glu Ser Ser Tyr Arg Gly Gln Glu Glu Tyr Val Leu Ser Tyr Glu
    690                 695                 700

Pro Val Asn Gln Gln Glu Val Asn Tyr Thr Arg Pro Val Ile Ile Leu
705                 710                 715                 720

Gly Pro Met Lys Asp Arg Ile Asn Asp Asp Leu Ile Ser Glu Phe Pro
                725                 730                 735

Asp Lys Phe Gly Ser Cys Val Pro His Thr Thr Arg Pro Lys Arg Asp
            740                 745                 750

Tyr Glu Val Asp Gly Arg Asp Tyr His Phe Val Thr Ser Arg Glu Gln
        755                 760                 765

Met Glu Lys Asp Ile Gln Glu His Lys Phe Ile Glu Ala Gly Gln Tyr
    770                 775                 780

Asn Asn His Leu Tyr Gly Thr Ser Val Gln Ser Val Arg Glu Val Ala
785                 790                 795                 800

Glu Lys Gly Lys His Cys Ile Leu Asp Val Ser Gly Asn Ala Ile Lys
                805                 810                 815

Arg Leu Gln Ile Ala Gln Leu Tyr Pro Ile Ser Ile Phe Ile Lys Pro
```

|     | 820 |     |     |     | 825 |     |     |     | 830 |     |     |
| --- | --- | --- | --- | --- | --- | --- | --- | --- | --- | --- | --- |
| Lys | Ser | Met | Glu | Asn | Ile | Met | Glu | Met | Asn | Lys | Arg | Leu | Thr | Glu | Glu |
|     |     |     | 835 |     |     |     |     | 840 |     |     |     | 845 |

Gln Ala Arg Lys Thr Phe Glu Arg Ala Met Lys Leu Glu Gln Glu Phe
              850                 855                 860

Thr Glu His Phe Thr Ala Ile Val Gln Gly Asp Thr Leu Glu Asp Ile
865             870                 875                 880

Tyr Asn Gln Val Lys Gln Ile Ile Glu Glu Gln Ser Gly Ser Tyr Ile
                885             890                 895

Trp Val Pro Ala Lys Glu Lys Leu
                900

<210> SEQ ID NO 52
<211> LENGTH: 4446
<212> TYPE: DNA
<213> ORGANISM: Homo sapiens

<400> SEQUENCE: 52

```
tgccttgacc aggacttggg actttgcgaa aggatcgcgg ggcccggaga ggtgttggag      60
agcacaatgg ctgaacaagt ccttcctcag gctttgtatt tgagcaatat gcggaaagct     120
gtgaagatac gggagagaac tccagaagac atttttaaac ctactaatgg gatcattcat     180
cattttaaaa ccatgcaccg atacacactg gaaatgttca gaacttgcca gttttgtcct     240
cagtttcggg agatcatcca caaagccctc atcgacagaa catccaggc cacccctggaa    300
agccagaaga aactcaactg gtgtcgagaa gtccggaagc ttgtggcgct gaaaacgaac    360
ggtgacggca attgcctcat gcatgccact tctcagtaca tgtgggggcgt tcaggacaca    420
gacttggtac tgaggaaggc gctgttcagc acgctcaagg aaacagacac acgcaacttt    480
aaattccgct ggcaactgga gtctctcaaa tctcaggaat tgttgaaaac ggggctttgc    540
tatgatactc ggaactggaa tgatgaatgg gacaatctta tcaaaatggc ttccacagac    600
acacccatgg cccgaagtgg acttcagtac aactcactgg aagaaataca catatttgtc    660
ctttgcaaca tcctcagaag gccaatcatt gtcatttcag acaaaatgct aagaagtttg    720
gaatcaggtt ccaatttcgc ccctttgaaa gtgggtggaa tttacttgcc tctccactgg    780
cctgcccagg aatgctacag atacccatt gttctcggct atgacagcca tcattttgta    840
cccttggtga ccctgaagga cagtgggcct gaaatccgag ctgttccact tgttaacaga    900
gaccggggaa gatttgaaga cttaaaagtt cacttttga cagatcctga aaatgagatg    960
aaggagaagc tcttaaaaga gtacttaatg gtgatagaaa tccccgtcca aggctgggac   1020
catggcacaa ctcatctcat caatgccgca aagttggatg aagctaactt accaaaagaa   1080
atcaatctgg tagatgatta ctttgaactt gttcagcatg agtacaagaa atggcaggaa   1140
aacagcgagc agggaggag agaggggcac gcccagaatc ccatggaacc ttccgtgccc   1200
cagctttctc tcatgatgt aaaatgtgaa acgcccaact gccccttctt catgtctgtg   1260
aacacccagc ctttatgcca tgagtgctca gagaggcggc aaaagaatca aaacaaactc   1320
ccaaagctga actccaagcc gggccctgag gggctccctg gcatggcgct cggggcctct   1380
cggggagaag cctatgagcc cttggcgtgg aaccctgagg agtccactgg ggggcctcat   1440
tcggccccac cgacagcacc cagcccttt ctgttcagtg agaccactgc catgaagtgc   1500
aggagccccg gctgccctt cacactgaat gtgcagcaca acggattttg tgaacgttgc   1560
cacaacgccc ggcaacttca cgccagccac gccccagacc acacaaggca cttggatccc   1620
```

```
gggaagtgcc aagcctgcct ccaggatgtt accaggacat ttaatgggat ctgcagtact    1680
tgcttcaaaa ggactacagc agaggcctcc tccagcctca gcaccagcct ccctccttcc    1740
tgtcaccagc gttccaagtc agatccctcg cggctcgtcc ggagcccctc cccgcattct    1800
tgccacagag ctggaaacga cgcccctgct ggctgcctgt ctcaagctgc acggactcct    1860
ggggacagga cggggacgag caagtgcaga aaagccggct gcgtgtattt tgggactcca    1920
gaaaacaagg cttttgcac actgtgtttc atcgagtaca gagaaaacaa acattttgct    1980
gctgcctcag ggaaagtcag tcccacagcg tccaggttcc agaacaccat tccgtgcctg    2040
gggagggaat gcggcaccct tggaagcacc atgtttgaag atactgcca gaagtgtttc     2100 attgaagctc agaatcagag atttcatgag gccaaaagga cagaagagca actgagatcg    2160
agccagcgca gagatgtgcc tcgaaccaca caaagcacct caaggcccaa gtgcgcccgg    2220
gcctcctgca agaacatcct ggcctgccgc agcgaggagc tctgcatgga gtgtcagcat    2280
cccaaccaga ggatgggccc tggggcccac cggggtgagc ctgcccccga agacccccc    2340 aagcagcgtt gccgggcccc cgcctgtgat cattttggca atgccaagtg caacggctac    2400
tgcaacgaat gctttcagtt caagcagatg tatggctaac cggaaacagg tgggtcacct    2460
cctgcaagaa gtgggcctc gagctgtcag tcatcatggt gctatcctct gaaccctca     2520 gctgccactg caacagtggg cttaaggtg tctgagcagg agaggaaaga taagctcttc    2580
gtggtgccca cgatgctcag gtttggtaac ccggagtgt tcccaggtgg ccttagaaag     2640
caaagcttgt aactggcaag ggatgatgtc agattcagcc caaggttcct cctctcctac    2700
caagcaggag gccaggaact tctttggact tggaaggtgt gcggggactg gccgaggccc    2760
ctgcaccctg cgcatcagga ctgcttcatc gtcttggctg agaaagggaa aagacacaca    2820
agtcgcgtgg gttggagaag ccagagccat tccacctccc ctcccccagc atctctcaga    2880
gatgtgaagc cagatcctca tggcagcgag gccctctgca agaagctcaa ggaagctcag    2940
ggaaaatgga cgtattcaga gagtgtttgt agttcatggt ttttccctac ctgcccggtt    3000
cctttcctga ggacccggca gaaatgcaga accatccatg gactgtgatt ctgaggctgc    3060
tgagactgaa catgttcaca ttgacagaaa aacaagctgc tctttataat atgcaccttt    3120
taaaaaatta gaatatttta ctgggaagac gtgtaactct ttgggttatt actgtcttta    3180
cttctaaaga agttagcttg aactgaggag taaaagtgtg tacatatata ataccccttt    3240
acattatgta tgagggattt ttttaaatta tattgaaatg ctgccctaga agtacaatag    3300
gaaggctaaa taataataac ctgttttctg gttgttgttg gggcatgagc ttgtgtatac    3360
actgcttgca taaactcaac cagctgcctt tttaagggga gctctagtcc tttttgtgta    3420 attcactta tttattttat tacaaacttc aagattattt aagtgaagat atttcttcag    3480
ctctggggaa aatgccacag tgttctcctg agagaacatc cttgctttga gtcaggctgt    3540
gggcaagttc ctgaccacag ggagtaaatt ggcctctttg atacactttt gcttgcctcc    3600
ccaggaaaga aggaattgca tccaaggtat acatacatat tcatcgatgt ttcgtgcttc    3660
tccttatgaa actccagcta tgtaataaaa aactatactc tgtgttctgt taatgcctct    3720
gagtgtccta cctccttgga gatgagatag ggaaggagca gggatgagac tggcaatggt    3780
cacagggaaa gatgtggcct tttgtgatgg ttttattttc tgttaacact gtgtcctggg    3840
ggggctggga agtcccctgc atcccatggt accctggtat tgggacagca aaagccagta    3900
accatgagta tgaggaaatc tctttctgtt gctggcttac agtttctctg tgtgctttgt    3960
ggttgctgtc atatttgctc tagaagaaaa aaaaaaagg aggggaaatg cattttcccc    4020
```

-continued

```
agagataaag gctgccattt tgggggtctg tacttatggc ctgaaaatat ttgtgatcca    4080
taactctaca cagcctttac tcatactatt aggcacactt tccccttaga gcccccaag     4140 tttttcccag acgaatcttt ataatttctt tccaaagata ccaaataaac ttcagtgttt    4200
tcatctaatt ctcttaaagt tgatatctta atattttgtg ttgatcatta tttccattct    4260
taatgtgaaa aaaagtaatt atttatactt attataaaaa gtatttgaaa tttgcacatt    4320
taattgtccc taatagaaag ccacctattc tttgttggat ttcttcaagt tttttctaaat   4380 aaatgtaact tttcacaaga gtcaacatta aaaataaat tatttaagaa caaaaaaaa     4440 aaaaaa                                                              4446
```

<210> SEQ ID NO 53
<211> LENGTH: 790
<212> TYPE: PRT
<213> ORGANISM: Homo sapiens

<400> SEQUENCE: 53

```
Met Ala Glu Gln Val Leu Pro Gln Ala Leu Tyr Leu Ser Asn Met Arg
1               5                   10                  15

Lys Ala Val Lys Ile Arg Glu Arg Thr Pro Glu Asp Ile Phe Lys Pro
            20                  25                  30

Thr Asn Gly Ile Ile His His Phe Lys Thr Met His Arg Tyr Thr Leu
        35                  40                  45

Glu Met Phe Arg Thr Cys Gln Phe Cys Pro Gln Phe Arg Glu Ile Ile
    50                  55                  60

His Lys Ala Leu Ile Asp Arg Asn Ile Gln Ala Thr Leu Glu Ser Gln
65                  70                  75                  80

Lys Lys Leu Asn Trp Cys Arg Glu Val Arg Lys Leu Val Ala Leu Lys
                85                  90                  95

Thr Asn Gly Asp Gly Asn Cys Leu Met His Ala Thr Ser Gln Tyr Met
            100                 105                 110

Trp Gly Val Gln Asp Thr Asp Leu Val Leu Arg Lys Ala Leu Phe Ser
        115                 120                 125

Thr Leu Lys Glu Thr Asp Thr Arg Asn Phe Lys Phe Arg Trp Gln Leu
    130                 135                 140

Glu Ser Leu Lys Ser Gln Glu Phe Val Glu Thr Gly Leu Cys Tyr Asp
145                 150                 155                 160

Thr Arg Asn Trp Asn Asp Glu Trp Asp Asn Leu Ile Lys Met Ala Ser
                165                 170                 175

Thr Asp Thr Pro Met Ala Arg Ser Gly Leu Gln Tyr Asn Ser Leu Glu
            180                 185                 190

Glu Ile His Ile Phe Val Leu Cys Asn Ile Leu Arg Arg Pro Ile Ile
        195                 200                 205

Val Ile Ser Asp Lys Met Leu Arg Ser Leu Glu Ser Gly Ser Asn Phe
    210                 215                 220

Ala Pro Leu Lys Val Gly Gly Ile Tyr Leu Pro Leu His Trp Pro Ala
225                 230                 235                 240

Gln Glu Cys Tyr Arg Tyr Pro Ile Val Leu Gly Tyr Asp Ser His His
                245                 250                 255

Phe Val Pro Leu Val Thr Leu Lys Asp Ser Gly Pro Glu Ile Arg Ala
            260                 265                 270

Val Pro Leu Val Asn Arg Asp Arg Gly Arg Phe Glu Asp Leu Lys Val
        275                 280                 285
```

```
His Phe Leu Thr Asp Pro Glu Asn Glu Met Lys Glu Lys Leu Leu Lys
    290                 295                 300

Glu Tyr Leu Met Val Ile Glu Ile Pro Val Gln Gly Trp Asp His Gly
305                 310                 315                 320

Thr Thr His Leu Ile Asn Ala Ala Lys Leu Asp Glu Ala Asn Leu Pro
                325                 330                 335

Lys Glu Ile Asn Leu Val Asp Asp Tyr Phe Glu Leu Val Gln His Glu
            340                 345                 350

Tyr Lys Lys Trp Gln Glu Asn Ser Glu Gln Gly Arg Arg Glu Gly His
        355                 360                 365

Ala Gln Asn Pro Met Glu Pro Ser Val Pro Gln Leu Ser Leu Met Asp
    370                 375                 380

Val Lys Cys Glu Thr Pro Asn Cys Pro Phe Phe Met Ser Val Asn Thr
385                 390                 395                 400

Gln Pro Leu Cys His Glu Cys Ser Glu Arg Arg Gln Lys Asn Gln Asn
                405                 410                 415

Lys Leu Pro Lys Leu Asn Ser Lys Pro Gly Pro Glu Gly Leu Pro Gly
            420                 425                 430

Met Ala Leu Gly Ala Ser Arg Gly Glu Ala Tyr Glu Pro Leu Ala Trp
        435                 440                 445

Asn Pro Glu Glu Ser Thr Gly Gly Pro His Ser Ala Pro Pro Thr Ala
    450                 455                 460

Pro Ser Pro Phe Leu Phe Ser Glu Thr Thr Ala Met Lys Cys Arg Ser
465                 470                 475                 480

Pro Gly Cys Pro Phe Thr Leu Asn Val Gln His Asn Gly Phe Cys Glu
                485                 490                 495

Arg Cys His Asn Ala Arg Gln Leu His Ala Ser His Ala Pro Asp His
            500                 505                 510

Thr Arg His Leu Asp Pro Gly Lys Cys Gln Ala Cys Leu Gln Asp Val
        515                 520                 525

Thr Arg Thr Phe Asn Gly Ile Cys Ser Thr Cys Phe Lys Arg Thr Thr
    530                 535                 540

Ala Glu Ala Ser Ser Ser Leu Ser Thr Ser Leu Pro Pro Ser Cys His
545                 550                 555                 560

Gln Arg Ser Lys Ser Asp Pro Ser Arg Leu Val Arg Ser Pro Ser Pro
                565                 570                 575

His Ser Cys His Arg Ala Gly Asn Asp Ala Pro Ala Gly Cys Leu Ser
            580                 585                 590

Gln Ala Ala Arg Thr Pro Gly Asp Arg Thr Gly Thr Ser Lys Cys Arg
        595                 600                 605

Lys Ala Gly Cys Val Tyr Phe Gly Thr Pro Glu Asn Lys Gly Phe Cys
    610                 615                 620

Thr Leu Cys Phe Ile Glu Tyr Arg Glu Asn Lys His Phe Ala Ala Ala
625                 630                 635                 640

Ser Gly Lys Val Ser Pro Thr Ala Ser Arg Phe Gln Asn Thr Ile Pro
                645                 650                 655

Cys Leu Gly Arg Glu Cys Gly Thr Leu Gly Ser Thr Met Phe Glu Gly
            660                 665                 670

Tyr Cys Gln Lys Cys Phe Ile Glu Ala Gln Asn Gln Arg Phe His Glu
        675                 680                 685

Ala Lys Arg Thr Glu Glu Gln Leu Arg Ser Ser Gln Arg Arg Asp Val
    690                 695                 700

Pro Arg Thr Thr Gln Ser Thr Ser Arg Pro Lys Cys Ala Arg Ala Ser
```

```
                705                 710                 715                 720
Cys Lys Asn Ile Leu Ala Cys Arg Ser Glu Glu Leu Cys Met Glu Cys
                    725                 730                 735
Gln His Pro Asn Gln Arg Met Gly Pro Gly Ala His Arg Gly Glu Pro
                740                 745                 750
Ala Pro Glu Asp Pro Pro Lys Gln Arg Cys Arg Ala Pro Ala Cys Asp
                    755                 760                 765
His Phe Gly Asn Ala Lys Cys Asn Gly Tyr Cys Asn Glu Cys Phe Gln
                770                 775                 780
Phe Lys Gln Met Tyr Gly
785                 790

<210> SEQ ID NO 54
<211> LENGTH: 29
<212> TYPE: PRT
<213> ORGANISM: Artificial
<220> FEATURE:
<223> OTHER INFORMATION: An artificially synthesised binding region

<400> SEQUENCE: 54

Pro Lys Arg His Gly Leu His Leu Ser Gln Glu Asn Gly Glu Lys Ile
1               5                   10                  15

Lys His Glu Ile Ile Asn Glu Asp Gln Glu Asn Ala Ile
            20                  25

<210> SEQ ID NO 55
<211> LENGTH: 56
<212> TYPE: PRT
<213> ORGANISM: Artificial
<220> FEATURE:
<223> OTHER INFORMATION: An artificially synthesised binding region

<400> SEQUENCE: 55

Ala Ile Asp Ala Leu Gln Leu Cys Cys Leu Leu Leu Pro Pro Pro Asn
1               5                   10                  15

Arg Arg Lys Leu Gln Leu Leu Met Arg Met Ile Ser Arg Met Ser Gln
                20                  25                  30

Asn Val Asp Met Pro Lys Leu His Asp Ala Met Gly Thr Arg Ser Leu
            35                  40                  45

Met Ile His Thr Phe Ser Arg Cys
        50                  55

<210> SEQ ID NO 56
<211> LENGTH: 1230
<212> TYPE: DNA
<213> ORGANISM: Artificial
<220> FEATURE:
<223> OTHER INFORMATION: An artificially synthesised promoter sequence

<400> SEQUENCE: 56
caccgtttga cccttctatc ccattttctc tatgcaatgt tgctttaact gttgttcaag      60
atcccaggat gcttgatccg ggaaagcaca gaggtctgct gccaacatac caacatacct    120
ctctgtcaag ttgtccaaaa tcacaagaga aagagccctg gactagagct aggagacctg    180
agttctcggc tgctctgtta ctgattagcg tctatgtcct ggacaagtt  gcttcccttt    240 ttccggacct cggttccttg tcctagatag gttctaaagt cggtgggtcc ttacagtaag    300
ttaggattct aaggtgcaat ccaaaagtaa aaccagtggt cagtatacct ctgagtagct    360
gttaaggtta caatacgagg ttcctcggcc ttccctttgg tagccaatgg atacggcctc    420
```

```
agtcagaggc cgtcaggttt actgggaaga gccttccggt tttgaaagac aggatctccg    480
ggtttccagt tctgtcactc actcggggta actttgggca aattctctct ggacctccta    540 ataggaggt cctcgtcacc ccgaggaagt tcgaagacgt gggcagtgac ttggaaagct     600
tcccgagatt ccccttctat aacctgggtg gctcagaccg ggagcgggt cccagccggc     660 cggtaattcc gcccggaggt gcgcacgaaa caaacctgca gcgctggccg agggcggctc    720
agcttcggag ggcgcgactc cgggtgagtt cttaaaggga ccgtcagagt ttgggtaaca    780
cctgcgatgc tgaccgggcg gggacgcagg cttgagggaa atgaatgaat gaatgaatga    840
gcgaatgaat gaacaaacct tctctgccca cccttaagta taccatactc ggaattaatc    900
agttaggctt aaaaatcttg tactataacc ctcaaactct tgccaagtta accagtgtct    960
ctatttcata tgtccttctg taatgaaacc cctcccccca agcctattac taagggacga   1020
agagtaactt aacaatcagc ctggagtgga aggcaatgca gagttggcac ccctccccga   1080
actcctccct ctccctctcc caggccccgc cctccccgcc ccctgggagg tgcagttggc   1140
tcctccttaa ggcggctttt ccccggtggg gatctacccc cggggtcgcc aggcgctgtc   1200
tctgccgcgg agttggaaac ggcactgctg                                    1230
```

<210> SEQ ID NO 57
<211> LENGTH: 17
<212> TYPE: DNA
<213> ORGANISM: Artificial
<220> FEATURE:
<223> OTHER INFORMATION: An artificially synthesized target sequence for siRNA

<400> SEQUENCE: 57
gatttggatg atgaaga                                                    17

<210> SEQ ID NO 58
<211> LENGTH: 17
<212> TYPE: DNA
<213> ORGANISM: Artificial
<220> FEATURE:
<223> OTHER INFORMATION: An artificially synthesized target sequence for siRNA

<400> SEQUENCE: 58
gcaggaacac atcaaga                                                    17

<210> SEQ ID NO 59
<211> LENGTH: 22
<212> TYPE: DNA
<213> ORGANISM: Artificial
<220> FEATURE:
<223> OTHER INFORMATION: 'An artificially synthesized primer for PCR

<400> SEQUENCE: 59
gctacaagta aagagggat gg                                               22

<210> SEQ ID NO 60
<211> LENGTH: 23
<212> TYPE: DNA
<213> ORGANISM: Artificial
<220> FEATURE:
<223> OTHER INFORMATION: An artificially synthesized primer for PCR

<400> SEQUENCE: 60
ggacagaaag gtaagtcagt ggg                                             23

-continued

```
<210> SEQ ID NO 61
<211> LENGTH: 21
<212> TYPE: DNA
<213> ORGANISM: Artificial
<220> FEATURE:
<223> OTHER INFORMATION: An artificially synthesized primer for PCR

<400> SEQUENCE: 61
tatatccaca ctgcacactg c                                             21

<210> SEQ ID NO 62
<211> LENGTH: 21
<212> TYPE: DNA
<213> ORGANISM: Artificial
<220> FEATURE:
<223> OTHER INFORMATION: An artificially synthesized primer for PCR

<400> SEQUENCE: 62
ccatttacag gagggtaaca c                                             21

<210> SEQ ID NO 63
<211> LENGTH: 32
<212> TYPE: DNA
<213> ORGANISM: Artificial
<220> FEATURE:
<223> OTHER INFORMATION: An artificially synthesized primer for PCR

<400> SEQUENCE: 63
attcgcggcc gcggatggag agtcagggtg tg                                 32

<210> SEQ ID NO 64
<211> LENGTH: 31
<212> TYPE: DNA
<213> ORGANISM: Artificial
<220> FEATURE:
<223> OTHER INFORMATION: An artificially synthesized primer for PCR

<400> SEQUENCE: 64
cccgctcgag agttctacga gataagtttc g                                  31

<210> SEQ ID NO 65
<211> LENGTH: 32
<212> TYPE: DNA
<213> ORGANISM: Artificial
<220> FEATURE:
<223> OTHER INFORMATION: An artificially synthesized primer for PCR

<400> SEQUENCE: 65
attcgcggcc gcggatggag agtcagggtg tg                                 32

<210> SEQ ID NO 66
<211> LENGTH: 31
<212> TYPE: DNA
<213> ORGANISM: Artificial
<220> FEATURE:
<223> OTHER INFORMATION: An artificially synthesized primer for PCR

<400> SEQUENCE: 66
cccgctcgag tacaaataat tcgtaatatt c                                  31

<210> SEQ ID NO 67
<211> LENGTH: 34
<212> TYPE: DNA
<213> ORGANISM: Artificial
<220> FEATURE:
<223> OTHER INFORMATION: An artificially synthesized primer for PCR
```

```
<400> SEQUENCE: 67
attcgcggcc gcttgataat agagaactaa gcca                              34

<210> SEQ ID NO 68
<211> LENGTH: 31
<212> TYPE: DNA
<213> ORGANISM: Artificial
<220> FEATURE:
<223> OTHER INFORMATION: An artificially synthesized primer for PCR

<400> SEQUENCE: 68
cccgctcgag aaccctctct aaatgaggtt g                                 31

<210> SEQ ID NO 69
<211> LENGTH: 40
<212> TYPE: DNA
<213> ORGANISM: Artificial
<220> FEATURE:
<223> OTHER INFORMATION: An artificially synthesized primer for PCR

<400> SEQUENCE: 69
attcgcggcc gcaccatggt aaacattttg gttgtttgtg                        40

<210> SEQ ID NO 70
<211> LENGTH: 28
<212> TYPE: DNA
<213> ORGANISM: Artificial
<220> FEATURE:
<223> OTHER INFORMATION: An artificially synthesized primer for PCR

<400> SEQUENCE: 70
cccgctcgag tccagcaaga agctcatc                                     28

<210> SEQ ID NO 71
<211> LENGTH: 38
<212> TYPE: DNA
<213> ORGANISM: Artificial
<220> FEATURE:
<223> OTHER INFORMATION: An artificially synthesized primer for PCR

<400> SEQUENCE: 71
attcgcggcc gcaccatgca aagcttgctg caacctca                          38

<210> SEQ ID NO 72
<211> LENGTH: 28
<212> TYPE: DNA
<213> ORGANISM: Artificial
<220> FEATURE:
<223> OTHER INFORMATION: An artificially synthesized primer for PCR

<400> SEQUENCE: 72
cccgctcgag agcttgagag gtagaaac                                     28

<210> SEQ ID NO 73
<211> LENGTH: 39
<212> TYPE: DNA
<213> ORGANISM: Artificial
<220> FEATURE:
<223> OTHER INFORMATION: An artificially synthesized primer for PCR

<400> SEQUENCE: 73
attcgcggcc gcaccatgtc ttacttacag actgcagtg                         39

<210> SEQ ID NO 74
<211> LENGTH: 30
```

```
<212> TYPE: DNA
<213> ORGANISM: Artificial
<220> FEATURE:
<223> OTHER INFORMATION: An artificially synthesized primer for PCR

<400> SEQUENCE: 74
cccgctcgag tcttagacta cggaactttg                                       30

<210> SEQ ID NO 75
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 75
ccaaaguucc guagucuaa                                                   19

<210> SEQ ID NO 76
<211> LENGTH: 21
<212> TYPE: DNA
<213> ORGANISM: Artificial
<220> FEATURE:
<223> OTHER INFORMATION: An artificially synthesized primer for PCR

<400> SEQUENCE: 76
tgcacactgt gtttcatcga g                                                21

<210> SEQ ID NO 77
<211> LENGTH: 20
<212> TYPE: DNA
<213> ORGANISM: Artificial
<220> FEATURE:
<223> OTHER INFORMATION: An artificially synthesized primer for PCR

<400> SEQUENCE: 77
acgctgtggg actgactttc                                                  20

<210> SEQ ID NO 78
<211> LENGTH: 32
<212> TYPE: DNA
<213> ORGANISM: Artificial
<220> FEATURE:
<223> OTHER INFORMATION: An artificially synthesized primer for PCR

<400> SEQUENCE: 78
gatcacgcgt agcccgaccc agagagtcac gt                                    32

<210> SEQ ID NO 79
<211> LENGTH: 30
<212> TYPE: DNA
<213> ORGANISM: Artificial
<220> FEATURE:
<223> OTHER INFORMATION: An artificially synthesized primer for PCR

<400> SEQUENCE: 79
gatcctcgag ctttcgcaaa gtcccaagtc                                       30

<210> SEQ ID NO 80
<211> LENGTH: 22
<212> TYPE: DNA
<213> ORGANISM: Artificial
<220> FEATURE:
<223> OTHER INFORMATION: An artificially synthesized primer for PCR

<400> SEQUENCE: 80
```

```
agcccgaccc agagagtcac gt                                             22

<210> SEQ ID NO 81
<211> LENGTH: 20
<212> TYPE: DNA
<213> ORGANISM: Artificial
<220> FEATURE:
<223> OTHER INFORMATION: An artificially synthesized primer for PCR

<400> SEQUENCE: 81
ctttcgcaaa gtcccaagtc                                                20

<210> SEQ ID NO 82
<211> LENGTH: 296
<212> TYPE: DNA
<213> ORGANISM: Artificial
<220> FEATURE:
<223> OTHER INFORMATION: An artificially synthesised promoter sequence

<400> SEQUENCE: 82
cgcgcccctc gccccctgcg ccctctggcg gccggctgga cgcacttcgc agcccgaccc      60
agagagtcac gtgactttgg aaagtcccgt ggaaatcccc gggcctacaa cccgcataca    120
actgaaacgg ggcaaagcag actgcgcagt ctgcagtctt cgtggcgggc caagcgagct    180
tggagcccgc gggggcggag cggtgagagc ggccgccaag agagatcaca cccccagccg    240
accctgccag cgagcgagcc cgacccagg cgtccatgga gcgtcgcctc cgcccg         296
```